(12) United States Patent
Marinkovich

(10) Patent No.: US 7,875,277 B2
(45) Date of Patent: Jan. 25, 2011

(54) COMPOSITIONS AND METHODS FOR INHIBITING SQUAMOUS CELL CARCINOMA

(75) Inventor: M. Peter Marinkovich, Redwood City, CA (US)

(73) Assignees: The Dept. of Veterans Affairs Office of The General Counsel, Washington, DC (US); The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/082,906

(22) Filed: Apr. 14, 2008

(65) Prior Publication Data

US 2008/0233125 A1 Sep. 25, 2008

Related U.S. Application Data

(60) Continuation-in-part of application No. 11/943,486, filed on Nov. 20, 2007, which is a division of application No. 10/766,317, filed on Jan. 27, 2004, now Pat. No. 7,323,551.

(51) Int. Cl.
*A61K 39/395* (2006.01)

(52) U.S. Cl. .................................. 424/130.1; 530/388.8

(58) Field of Classification Search ........................ None
See application file for complete search history.

(56) References Cited

U.S. PATENT DOCUMENTS

| | | | |
|---|---|---|---|
| 4,816,567 A | 3/1989 | Cabilly et al. | |
| 5,869,045 A * | 2/1999 | Hellstrom et al. | ........ 424/130.1 |
| 6,120,991 A | 9/2000 | Carter et al. | |
| 6,294,356 B1 | 9/2001 | Jones et al. | |
| 7,256,001 B2 | 8/2007 | Katayama et al. | |
| 2002/0076736 A1 | 6/2002 | Findell et al. | |

FOREIGN PATENT DOCUMENTS

| | | |
|---|---|---|
| WO | WO9010448 A2 | 9/1990 |
| WO | WO9104753 A1 | 4/1991 |
| WO | WO9604000 A1 | 2/1996 |
| WO | WO0026342 A1 | 5/2000 |
| WO | WO0187239 A2 | 11/2001 |
| WO | 03/016907 | 2/2003 |

OTHER PUBLICATIONS

Goldfinger, J Cell Science, 1999, 112:2615-2629.*
Ahmed et al., "Chapter 39: Immunity to Viruses," Fundamental Immunology, 4th edition, W.E. Paul, ed., Lippincott-Raven Publishers, 1999, pp. 1295-1334.
Alama et al., "Antisense oligonucleotides as therapeutic agents," Pharmacol Res., 1997, 36(3):171-178.
Amano et al., "Bone morphogenetic protein 1 is an extracellular processing enzyme of the laminin 5 gamma 2 chain," J. Biol. Chem, 2000, 275(30): 22728-22735.

Berndt et al., "Oral squamous cell carcinoma invasion is associated with a laminin-5 matrix re-organization but independent of basement membrane and hemidesmosome formation. clues from an in vitro invasion model," Invasion Metastasis, 1997, 17(5):251-258.
Boado et al., "Drug delivery of antisense molecules to the brain for treatment of Alzheimer's disease and cerebral AIDS," J. Pharm. Sci., 1998, 87(11):1308-1315.
Cassidy et al., "Melanocytes adhere to and synthesize laminin-5 in vitro," Exp. Dermatol., 1999, 8(3):212-221.
Chan et al., "Laminin-6 and laminin-5 are recognized by autoantibodies in a subset of cicatricial pemphigoid," J Invest. Dermatol., 1997, 108(6):848-853.
Chen et al., "NC1 domain of type VII collagen binds to the beta3 chain of laminin 5 via a unique subdomain within the fibronectin-like repeats," J Invest. Dermatol., 1999, 112(2):177-183.
Cheng et al., "Self-assembly of laminin isoforms," J Biol. Chem., 1997, 272(50):31525-31532.
Crooke, "Advances in understanding the pharmacological properties of antisense oligonucleotides," Adv. Pharmacol., 1997, 40:1-49.
Dajee et al., "NF-kappaB blockade and oncogenic Ras trigger invasive human epidermal neoplasia," Nature, 2003, 421(6923):639-643.
Diederichsen, "Alanyl-PNA homoduplex: A-T pairing with the N7-regioisomer of adenine," Bioorg. Med. Chem. Lett., 1998, 8(2):165-168.
Fukushima et al., "Integrin alpha3beta1-mediated interaction with laminin-5 stimulates adhesion, migration and invasion of malignant glioma cells," Int. J Cancer, 1998, 76(1):63-72.
Huse et al., "Generation of a large combinatorial library of the immunoglobulin repertoire in phage lambda," Science, 1989, 246:1275-1281.
Jordan et al., "New hetero-oligomeric peptide nucleic acids with improved binding properties to complementary DNA," Bioorg. Med. Chem. Lett., 1997, 7(6):687-690.
Jordan et al., "Synthesis of new building blocks for peptide nucleic acids containing monomers with variations in the backbone," Bioorg. Med. Chem. Lett., 1997, 7(6):681-686.
Kirtschig et al., "Anti-basement membrane autoantibodies in patients with anti-epiligrin cicatricial pemphigoid bind the alpha subunit of laminin 5," J Invest. Dermatol., 1995, 105(4):543-548.
Kumar et al., "Pyrrolidine nucleic acids: DNA/PNA oligomers with 2-hydroxy/aminomethyl-4-(thymin-1-yl)pyrrolidine-N-acetic acid," Org. Lett., 2001, 3(9):1269-1272.
Lavrosky et al., "Therapeutic potential and mechanism of action of oligonucleotides and ribozymes," Biochem. Mol. Med., 1997, 62(1):11-22.
Lee et al., "Polyamide nucleic acid targeted to the primer binding site of the HIV-1 RNA genome blocks in vitro HIV-1 reverse transcription," Biochemistry, 1998, 37(3):900-910.

(Continued)

*Primary Examiner*—Misook Yu
*Assistant Examiner*—Mark Halvorson
(74) *Attorney, Agent, or Firm*—Lahive & Cockfield, LLP; Jane E. Remillard, Esq.; Jeanne M. DiGiorgio, Esq.

(57) ABSTRACT

The present invention relates to compositions and methods for detecting and inhibiting squamous cell carcinoma using agents that target the laminin 5 alpha 3 G4-G5 domain.

10 Claims, 12 Drawing Sheets
(7 of 12 Drawing Sheet(s) Filed in Color)

OTHER PUBLICATIONS

Li et al., "Laminin-10 is crucial for hair morphogenesis," EMBO J, 2003, 22(10):2400-2410.

Maddox et al., "Elevated serum levels in human pregnancy of a molecule immunochemically similar to eosinophil granule major basic protein," J Exp Med, 1983, 158(4):1211-1226.

Marcus-Sekura, "Techniques for using antisense oligodeoxyribonucleotides to study gene expression," Anal. Biochem., 1988, 172(2):289-295.

Marinkovich et al., "Basement membrane proteins kalinin and nicein are structurally and immunologically identical," Lab. Invest., 1993, 69(3):295-299.

Marinkovich et al., "LAD-1 is absent in a subset of junctional epidermolysis bullosa patients," J Invest. Dermatol., 1997, 109(3):356-359.

Marinkovich et al., "Prenatal diagnosis of Herlitz junctional epidermolysis bullosa by amniocentesis," Prenat. Diagn., 1995, 15(11):1027-1034.

Marinkovich et al., "The anchoring filament protein kalinin is synthesized and secreted as a high molecular weight precursor," J Biol. Chem., 1992, 267(25):17900-17906.

Marinkovich et al., "The dermal-epidermal junction of human skin contains a novel laminin variant," J Cell Biol., 1992, 119(3):695-703.

Marinkovich, "The molecular genetics of basement membrane diseases," Arch. Dermatol., 1993, 129 (12):1557-1565.

McGowan et al., "Laminins and human disease," Microsc. Res. Tech., 2000, 51(3):262-279.

Meneguzzi et al., "Kalinin is abnormally expressed in epithelial basement membranes of Herlitz's junctional epidermolysis bullosa patients," Exp. Dermatol., 1992, 1(5):221-229.

Miguel et al., "Establishment and characterization of cell line LSV5 that retains the altered adhesive properties of human junctional epidermolysis bullosa keratinocytes," Exp. Cell Res., 1996, 224(2):279-290.

Miller, "Progress Toward Human Gene Therapy," Blood, 1990, 76(2):271-278.

Mizushima et al., "Identification of integrin-dependent and -independent cell adhesion domains in COOH-terminal globular region of laminin-5 alpha 3 chain," Cell Growth Differ., 1997, 8(9):979-987.

Morris et al., "A new peptide vector for efficient delivery of oligonucleotides into mammalian cells," Nucleic Acids Res., 1997, 25(14):2730-2736.

Nielsen et al., "Peptide nucleic acid (PNA). A DNA mimic with a pseudopeptide backbone," Chem. Soc. Rev., 1997,26(22):73-78.

Orlandi et al., "Cloning immunoglobulin variable domains for expression by the polymerase chain reaction," Proc. Natl. Acad. Sci. USA, 1989, 86(10):3833-3837.

Ortiz-Urda et al., "Injection of genetically engineered fibroblasts corrects regenerated human epidermolysis bullosa skin tissue," J Clin. Invest., 2003, 111(2):251-255.

O'Toole et al., "Laminin-5 inhibits human keratinocyte migration," Exp. Cell Res., 1997, 233(2):330-339.

Pardridge et al., "Vector-mediated delivery of a polyamide ("peptide") nucleic acid analogue through the blood-brain barrier in vivo," Proc. Natl. Acad. Sci. USA, 1995 92(12):5592-5596.

Pyke et al., "Laminin-5 is a marker of invading cancer cells in some human carcinomas and is coexpressed with the receptor for urokinase plasminogen activator in budding cancer cells in colon adenocarcinomas," Cancer Res., 1995 ,55(18):4132-4139.

Pyke, et al., "The gamma 2 chain of kalinin/laminin 5 is preferentially expressed in invading malignant cells in human cancers," Am. J Pathol., 1994, 145(4):782-791.

Rammensee et al., "Syfpeithi: database for MHC ligands and peptide motifs," Immunogenetics, 1999, 50 (3-4):213-219.

Rossi et al., "Exploring the use of antisense, enzymatic RNA molecules (ribozymes) as therapeutic agents," Antisense Res. Dev., 1991, 1(3):285-288.

Rossi, "Therapeutic antisense and ribozymes," Br. Med. Bull., 1995, 51(1):217-225.

Russell et al., "Alpha 6 beta 4 integrin regulates keratinocyte chemotaxis through differential GTPase activation and antagonism of alpha 3 beta 1 integrin," J Cell Sci., 2003, 116(Pt 17):3543-3556.

Ryan et al., "Cloning of the LamA3 gene encoding the alpha 3 chain of the adhesive ligand epiligrin. Expression in wound repair," J Biol. Chem., 1994, 269(36):22779-22787.

Slater et al., "The latex allergen Hev b 5 transcript is widely distributed after subcutaneous injection in BALB/c mice of its DNA vaccine," J Allergy Clin. Immunol., 1998, 102(3):469-475.

Stoltzfus et al., "Laminin-5 gamma2 chain expression facilitates detection of invasive squamous cell carcinoma of the uterine cervix," Int. J Gynecol. Pathol., 2004, 23(3):215-222.

Uckert et al., "Retrovirus-mediated gene transfer in cancer therapy," Pharmacol. Ther., 1994, 63(3): 323-347.

Van Hest et al., "Efficient introduction of alkene functionality into proteins in vivo," FEBS Lett., 1998, 428:(1-2):68-70.

Veitch et al., "Mammalian tolloid metalloproteinase, and not matrix metalloprotease 2 or membrane type 1 metalloprotease, processes laminin-5 in keratinocytes and skin," J Biol. Chem., 2003, 278(18): 15661-15668.

Verhoeyen et al., "Reshaping human antibodies: grafting an antilysozyme activity," Science, 1988, 239 (4847):1534-1536.

Weinberg, "How cancer arises: an explosion of research in uncovering the long-hidden molecular underpinnings of cancer and suggesting new therapies," Scientific American, 1996, 275(3):62-70.

Winter et al., "Man-made antibodies," Nature, 1991, 349(6307):293-299.

* cited by examiner

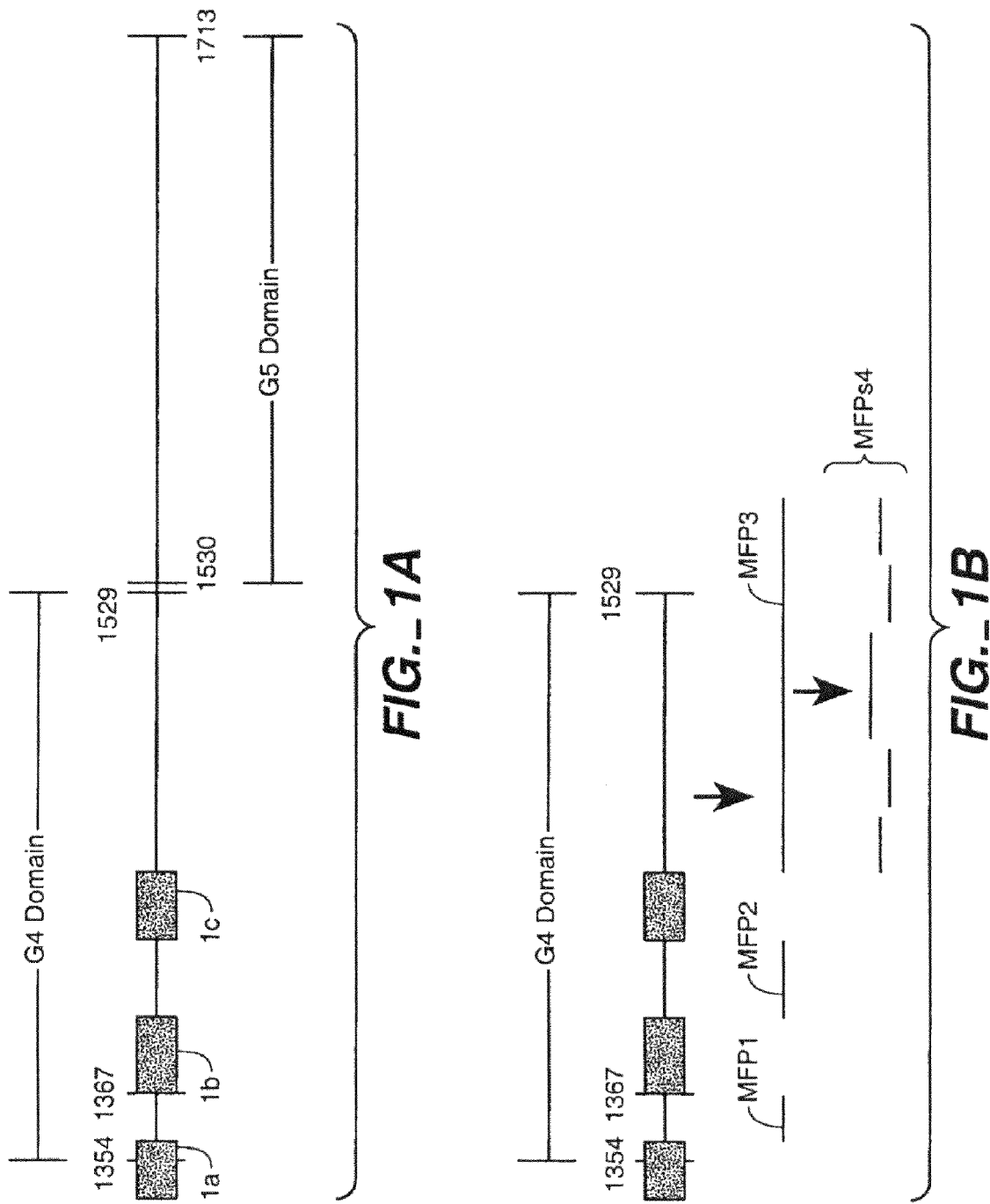

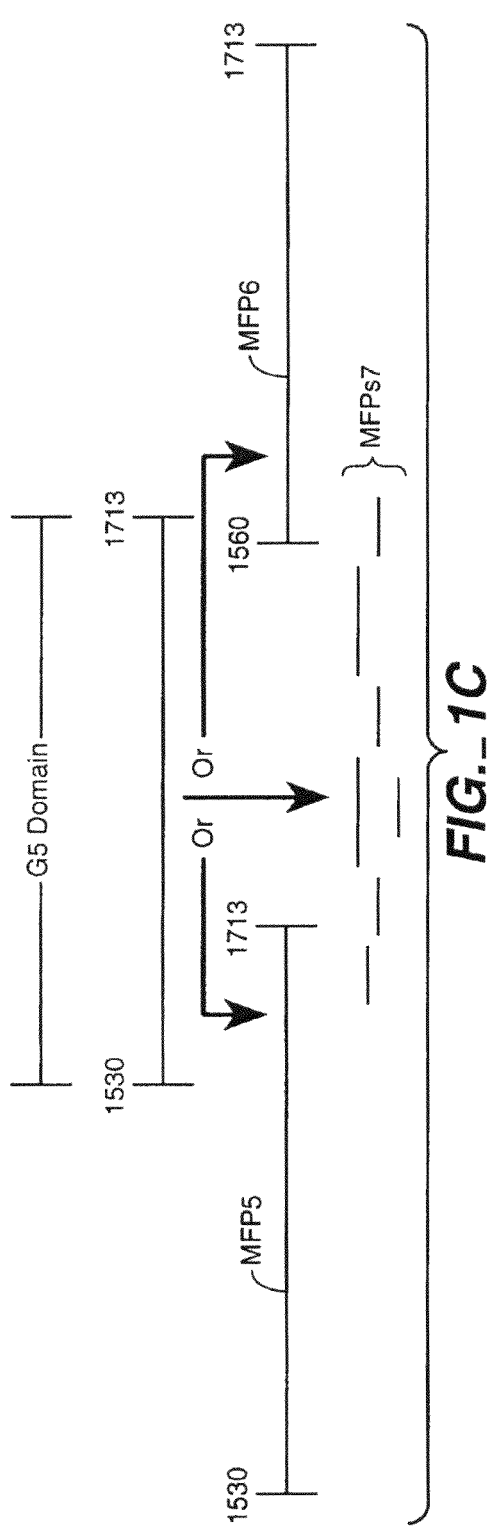
FIG._1C
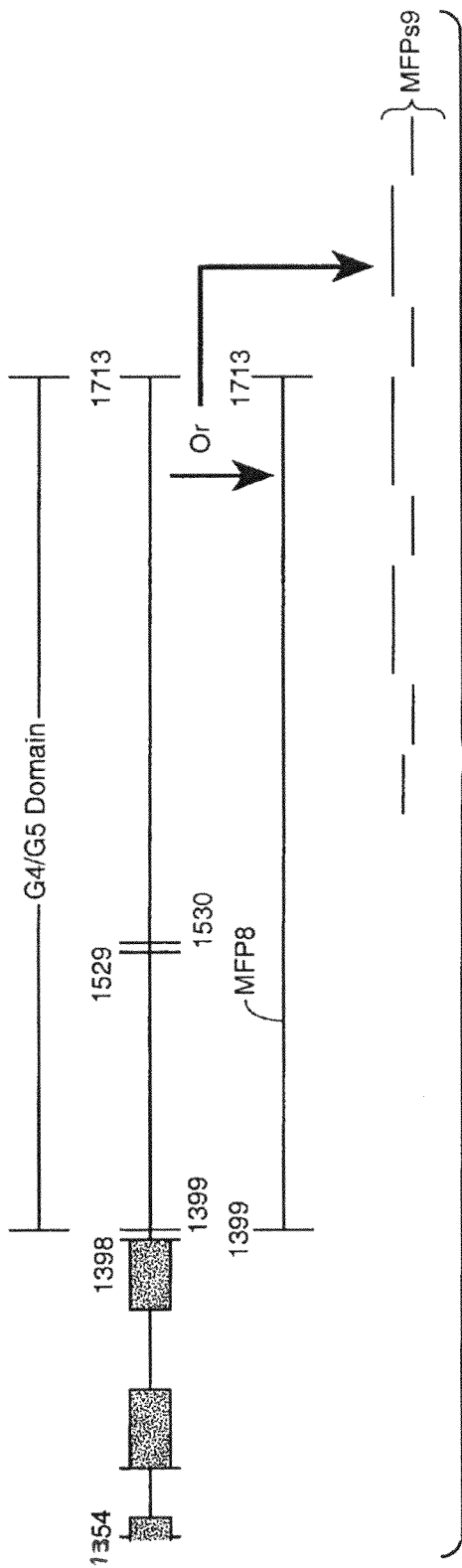
FIG._1D

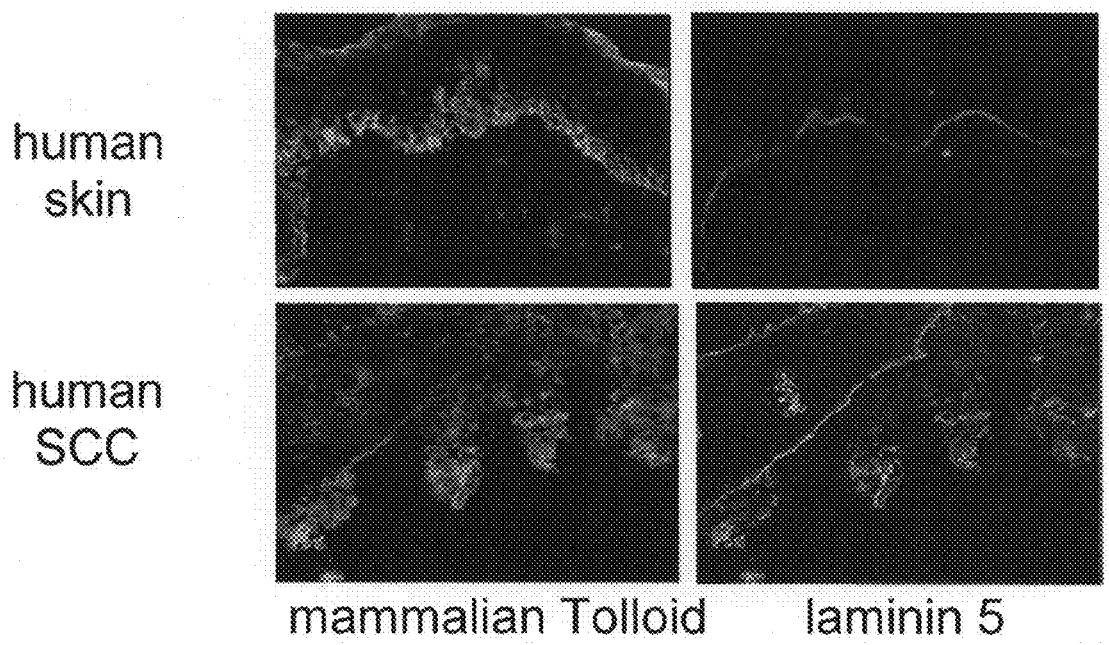
FIG._2

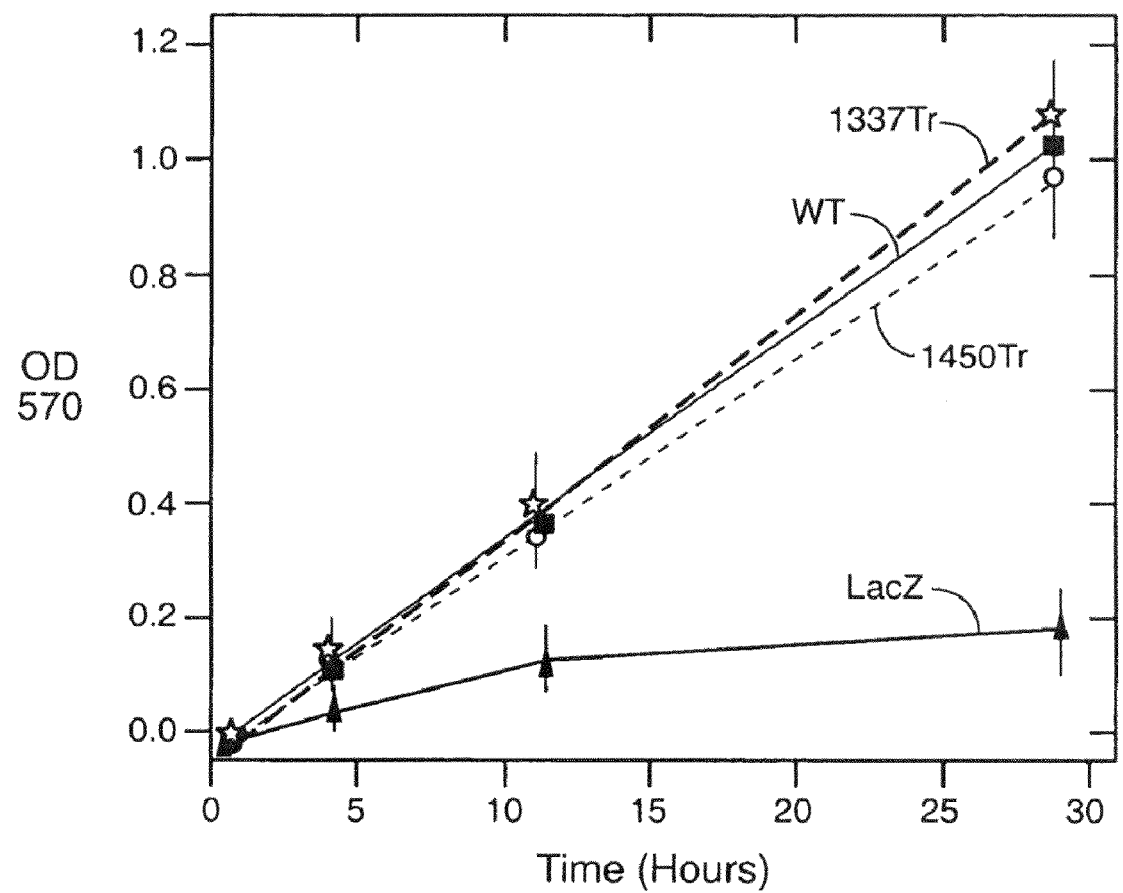
FIG._3

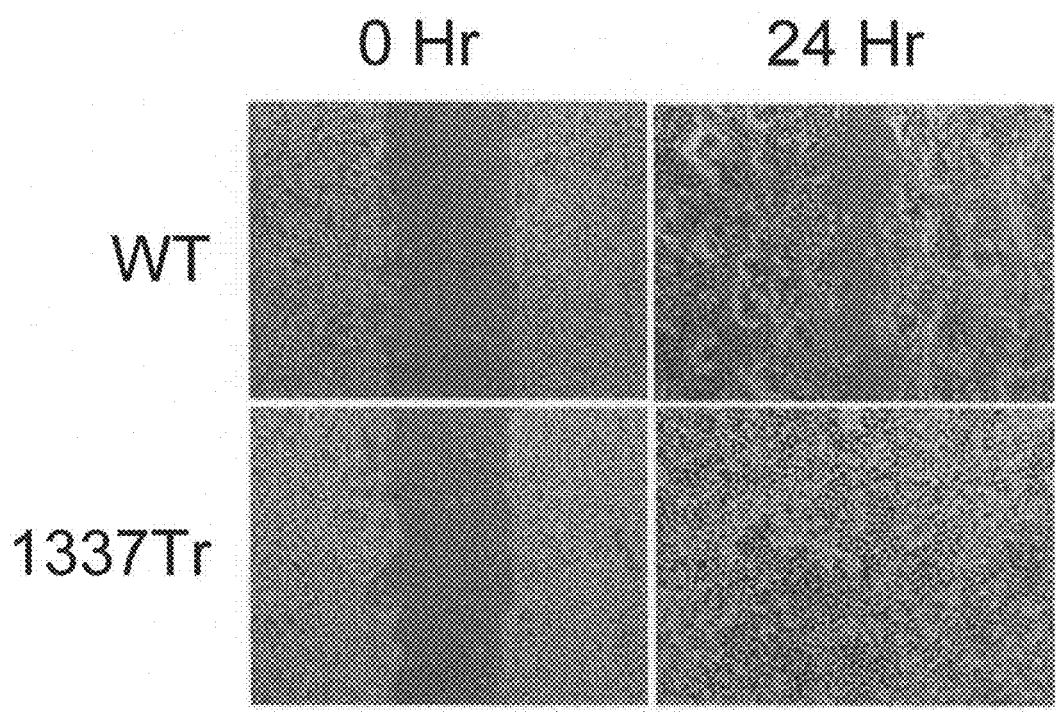
FIG._4

FIG._5

COMPOSITIONS AND METHODS FOR INHIBITING SQUAMOUS CELL CARCINOMA

FEDERALLY-SPONSORED RESEARCH OR DEVELOPMENT

This invention was made with Government support under contract AR047223 awarded by the National Institutes of Health. The Government has certain rights in this invention.

The present invention relates to compositions and methods for detecting and inhibiting squamous cell carcinoma using agents that target the laminin 5 alpha 3 G4-G5 domain.

INTRODUCTION

Squamous cell carcinoma (SCC) is common form of cancer and is the second most common form of skin cancer in the United States. SCCs are highly invasive and metastatic. SCCs are associated with a comparatively high risk of recurrence, resulting in significant mortality. SCC can be diagnosed by biopsy. However, SCCs are typically not as distinct as basal cell carcinomas or melanomas, making detection and diagnosis difficult. Current methods of treatment, i.e. surgery, radiotherapy, and chemotherapy, require continued monitoring due to the metastatic nature of the disease. The development of alternative methods of detection and treatment is therefore desirable.

The compositions and methods described herein are directed towards identifying agents that can detect and inhibit proteins associated with SCC tumorigenesis. Of particular interest, are agents that interact with the laminin-5 alpha 3 chain G4 and/or G5 domains.

SUMMARY

Provided herein are compositions and methods useful for detecting and treating squamous cell carcinoma (SCC). The compositions generally comprise antibodies capable of binding a migration facilitating protein (MFP) of a laminin 5 alpha 3 chain G4 and/or G5 domain or subdomain. MFPs typically comprise 8, 9, 10 or more amino acids present in the laminin 5 alpha 3 G4 and/or 5 domains that do not comprise a recognized cleavage site for bone morphogenetic protein-1 (BMP-1) and BMP-1 related proteins. For example, MFPs can be generated comprising: (1) the G5 subdomain; (2) the G4 subdomain lying between amino acid 1358 and amino acid 1366; (3) the G4 subdomain lying between amino acid 1375 and amino acid 1390; (4) the G4 subdomain lying between amino acid 1399 and 1530; and, (5) the G4-5 subdomain lying between amino acid 1399 and amino acid 1713. As will be appreciated by a person of skill in the art, MFPs encoding other subdomains within the laminin 5 alpha 3 G4 and/or 5 domains can also be generated and used in the methods of the present invention. The compositions can include additional components, such as, detectable labels and a pharmaceutically acceptable carrier.

The methods generally involve administering a therapeutically effective amount of a composition comprising one or more antibodies capable of inhibiting SCC tumorigenesis to a patient diagnosed with SCC. Treatment of a patient diagnosed with SCC with the compositions described herein can be combined with other medical means for treating SCC, such as surgery, radiotherapy, and chemotherapy. The SCC can be selected from the group consisting of skin cancer, lung cancer, head cancer, gastric cancer, colorectal cancer, throat cancer, cancer of the urinary tract, cancer of the reproductive tract, esophageal cancer, and bronchiogenic carcinoma.

Also provided are methods that utilize the MFPs described above. In some embodiments, a method is provided for detecting the binding activity of a candidate agent in a sample that comprises the steps of: (a) contacting the sample with an MFP under conditions effective to permit binding between the MFP and the candidate agent (if present); and, (b) detecting the binding of the candidate agent.

A number of different assays can be used to detect binding of the candidate agent. For example, in some embodiments, the candidate agent is labeled and binding determined directly. In other embodiments, the binding of the candidate agent is determined through the use of competitive binding assays in which the competitor is a binding moiety known to bind the MFP, i.e., an antibody. Displacement of the competitor by the candidate agent is an indication that the candidate agent is capable of binding the MFP.

Also provided herein are methods for screening for candidate agents that inhibit SCC tumorigenesis. In some embodiments, a method is provided for screening for candidate agents that inhibit SCC tumor development comprising the steps of: a) subcutaneously injecting nude mice with a suspension comprising: i) Ras/IKB transformed epithelial cells; ii) a migration facilitating protein (MFP) of a laminin G4 and/or G5 domain or subdomain; iii) one or more candidate agents; and b) determining the presence or absence of a tumor.

In some embodiments, a method is provided to evaluate the effect of a candidate SCC drug comprising administering the drug to a patient diagnosed with SCC and removing a cell sample from the patient. A number of different assays can be used to evaluate the effect of the candidate drug. For example, the expression profile of the cell sample can be determined and compared with an expression profile of a healthy individual. In some embodiments, the cell sample can be analyzed for the presence or absence of an MFP associated with SCC development before and after treatment with a candidate drug. In yet other embodiments, the size of the tumor before and after treatment with a candidate drug can be analyzed to determine if the drug is effective in inhibiting the invasion of nearby normal cells.

Also provided herein is a method for diagnosing SCC comprising removing a cell sample from an individual and analyzing the cell with one or more MFPs determined to be involved in SCC proliferation and/or metastasis.

These and other features of the compositions and methods described herein will become more apparent from the detailed description below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Aspects of the invention, can be more fully understood with respect to the following drawings. In the drawings, similar elements are referenced with like numbers.

FIG. 1A provides a cartoon illustrating the G4 (1) and G5 (2) domains of the alpha 3 chain of laminin 5, including the cleavage recognition sites (1a, 1b, 1c) for bone morphogenetic protein-1 (BMP-1); FIG. 1B illustrates exemplary embodiments of migration facilitating proteins (MFPs) that can be generated from the G4 domain; FIG. 1C illustrates exemplary embodiments of migration facilitating proteins (MFPs) that can be generated from the G5 domain; FIG. 1D illustrates exemplary embodiments of migration facilitating proteins (MFPs) that can be generated comprising amino acids present in both the G4 and G5 domains.

FIG. 2 depicts normal human skin epithelia cells and SCC epithelial derived tumor cells.

FIG. 3 illustrates the results from a migration assay comparing wild-type cells, and keratinocytes transformed with truncated versions of the laminin-5 alpha 3 chain.

FIG. 4 illustrates a scratch assay in which cells lacking the G4 and G5 domain (i.e. 1337TR) migrate more efficiently than cells expressing wild-type laminin-5 alpha 3 chain.

FIG. 5 illustrates a mouse model of human SCC. The left panel depicts tumor formation in nude mice transformed with RAS/IKB keratinocytes transformed with wild-type laminin-5 alpha 3 chain. The middle and right panels illustrate that SCC tumors are not formed in nude mice transformed with RAS/IKB laminin-5 negative keratinocytes (right panel) or with a laminin-5 construct lacking the G4 and G5 domains (middle panel).

DETAILED DESCRIPTION

Figure 6:
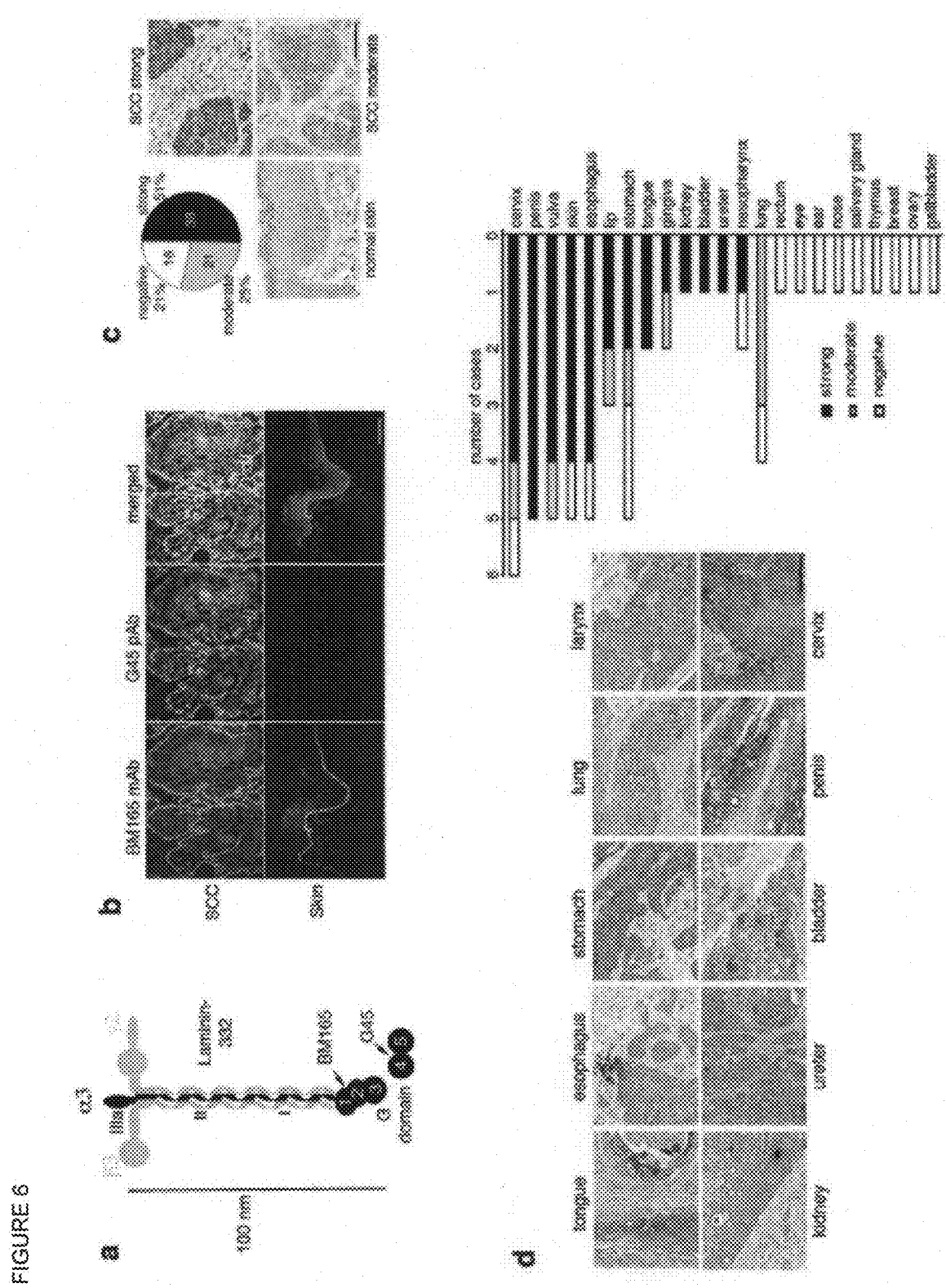
FIGS. 6A-6D. Laminin-332 G45 is present in human SCC tumors but absent in normal skin. (a) Schematic diagram of laminin-332's α3, β3 and γ2 chains, highlighting α3 chain domain structure (black), proteolytic cleavage and epitopes for BM165 mAb and G45 pAb. (b) Immunofluorescence microscopic analysis of frozen sections of human SCC (upper panels) and neonatal skin (lower panels) using BM165 mAb (green) and G45 pAb (red). Merged images with nuclear Hoechst staining (blue) are shown in the panels to the right. Images are representative of four frozen SCC and skin samples tested. Scale bar=50 μm. (c) Results of analysis of 75 cases of paraffin embedded human cutaneous SCC using G45 pAb by immunohistochemical analysis. Upper left diagram shows number and percentage of samples which showed negative, moderate or strong expression. Bottom and right panels show representative examples of moderate/strong expression, as well as negative skin control. Scale bar=50 μm. (d) Left: Representative samples of 56 cases of paraffin embedded human extra-cutaneous SCC from various tissues using G45 pAb by immunohistochemical analysis showing moderate to strong expression. Scale bar=50 μm. Right: results of extra-cutaneous SCC tissue survey, showing tissues of origin, and intensity of staining for G45 pAb antibody.

It is to be understood that both the foregoing general description and the following detailed description are exemplary and explanatory only and are not restrictive of the inventions described herein. In this application, the use of the singular includes the plural unless specifically state otherwise. Also, the use of "or" means "and/or" unless state otherwise. Similarly, "comprise," "comprises," "comprising," "include," "includes" and "including" are not intended to be limiting. Unless defined otherwise, all technical and scientific terms used herein have the same meanings as commonly understood by one of ordinary skill in the art to which the invention belongs.

DEFINITIONS

As used herein, the following terms and phrases are intended to have the following meanings:

"Antibody" has its standard meaning and is intended to refer to intact molecules as to fragments thereof, such as Fab, F(ab')2, and Fv fragments, that are capable of binding an epitope.

"Cancer" has its standard meaning and is intended to refer to any malignant tumor of potentially unlimited growth that expands locally by proliferation and systemically by metastasis.

"Neoplasm" has its standard meaning and is intended to refer to the abnormal growth of a tissue, such as a tumor.

"Nucleobase" means those naturally occurring and those synthetic nitrogenous, aromatic moieties commonly found in the nucleic acid arts. Examples of nucleobases include purines and pyrimidines, genetically encoding nucleobases, analogs of genetically encoding nucleobases, and purely synthetic nucleobases. Specific examples of genetically encoding nucleobases include adenine, cytosine, guanine, thymine, and uracil. Specific examples of analogs of genetically encoding nucleobases and synthetic nucleobases include 5-methylcytosine, pseudoisocytosine, 2-thiouracil and 2-thiothymine, 2-aminopurine, N9-(2-amino-6-chloropurine-), N9-(2,6-diaminopurine), hypoxanthine, N9-(7-deaza-guanine), N9-(7-deaza-8-aza-guanine) and N8-(7-deaza-8-aza-adenine). 5-propynyl-uracil, 2-thio-5-propynyl-uracil. Other non-limiting examples of suitable nucleobases include those nucleobases illustrated in FIGS. 2(A) and 2(B) of U.S. Pat. No. 6,357,163, incorporated herein by reference in its entirety.

"Nucleoside" refers to a nucleobase linked to a pentose sugar. Pentose sugars include ribose, 2'-deoxyribose, 3'-deoxyribose, and 2',3'-dideoxyribose.

"Nucleoside analog" refers to a nucleobase linked to a sugar, other than a pentose sugar. For example, a nucleobase linked to hexose.

"Nucleotide" refers to compound comprising a nucleobase, a pentose sugar and a phosphate. Thus, as used herein a nucleotide refers to a phosphate ester of a nucleoside, e.g., a triphosphate.

"Nucleobase Polymer or Oligomer" refers to two or more nucleobases that are connected by linkages that permit the resultant nucleobase polymer or oligomer to hybridize to a polynucleotide having at least a partially complementary nucleobase sequence. Nucleobase polymers or oligomers include, but are not limited to, poly- and oligonucleotides (e.g., DNA and RNA polymers and oligomers), poly- and oligonucleotide analogs and poly- and oligonucleotide mimics, such as polyamide nucleic acids or peptide nucleic acids. Polyamide nucleic acids and peptide nucleic acids are two different phrases used in the literature to describe the same molecule, abbreviated herein as PNA. Nucleobase polymers or oligomers can vary in size from a few nucleobases, for example, from 2 to 40 nucleobases, to several hundred nucleobases, to several thousand nucleobases, or more.

"Polynucleotides or Oligonucleotides" refer to nucleobase polymers or oligomers in which the nucleobases are linked by sugar phosphate linkages (sugar-phosphate backbone).

Exemplary poly- and oligonucleotides include polymers of 2'-deoxyribonucleotides (DNA) and polymers of ribonucleotides (RNA). A polynucleotide may be composed entirely of ribonucleotides, entirely of 2'-deoxyribonucleotides or combinations thereof.

"Polynucleotide or Oligonucleotide Analog" refers to nucleobase polymers or oligomers in which the nucleobases are linked by a phosphate backbone comprising one or more sugar analogs or phosphate analogs. Typical oligonucleotide or polynucleotide analogs include, but are not limited to, sugar alkylphosphonates, sugar phosphoramidites, sugar alkyl- or substituted alkylphosphotriesters, sugar phosphorothioates, sugar phosphorodithioates, sugar phosphates and sugar phosphate analogs in which the sugar is other than 2'-deoxyribose or ribose, nucleobase polymers having positively charged sugar-guanidyl interlinkages such as those described in U.S. Pat. No. 6,013,785 and U.S. Pat. No. 5,696,253 (see also, Dagani 1995, Chem. & Eng. News 4-5:1153; Dempey et al., 1995, J. Am. Chem. Soc. 117:6140-6141). Such positively charged analogues in which the sugar is 2'-deoxyribose are referred to as "DNGs," whereas those in which the sugar is ribose are referred to as "RNGs." Specifically included within the definition of poly- and oligonucleotide analogs are locked nucleic acids (LNAs; see, e.g. Elayadi et al., 2002, Biochemistry 41:9973-9981; Koshkin et al., 1998, J. Am. Chem. Soc. 120:13252-3; Koshkin et al., 1998, Tetrahedron Letters, 39:4381-4384; Jumar et al., 1998, Bioorganic & Medicinal Chemistry Letters 8:2219-2222; Singh and Wengel, 1998, Chem. Commun., 12:1247-1248; WO 00/56746; WO 02/28875; and, WO 01/48190; all of which are incorporated herein by reference in their entireties).

"Polynucleotide or oligonucleotide mimic" refers to nucleobase polymers or oligomers in which the nucleobases are connected by a linkage other than a sugar-phosphate linkage or a sugar-phosphate analog linkage. Mimics with a specific linkage include peptide nucleic acids (PNAs) as described in any one or more of U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470, 6,451,968, 6,441,130, 6,414,112 and 6,403,763; all of which are incorporated herein by reference. Other types of mimics are described in the following publications: Lagriffoul et al., 1994, Bioorganic & Medicinal Chemistry Letters, 4: 1081-1082; Petersen et al., 1996, Bioorganic & Medicinal Chemistry Letters, 6: 793-796; Diderichsen et al, 1996, Tett. Lett. 37: 475-478; Fujii et al., 1997, Bioorg. Med. Chem. Lett. 7: 637-627; Jordan et al., 1997, Bioorg. Med. Chem. Lett. 7: 687-690; Krotz et al., 1995, Tett. Lett. 36: 6941-6944; Lagriffoul et al, 1994, Bioorg. Med. Chem. Lett. 4: 1081-1082; Diederichsen, U., 1997, Bioorganic & Medicinal Chemistry 25 Letters, 7: 1743-1746; Lowe et al., 1997, J. Chem. Soc. Perkin Trans. 1, 1: 539-546; Lowe et al., 1997, J. Chem. Soc. Perkin Trans. 11: 547-554; Lowe et al., 1997, 1. Chem. Soc. Perkin Trans. 1 1:5 55-560; Howarth et al., 1997, 1. Org. Chem. 62: 5441-5450; Altmann, K-H et al., 1997, Bioorganic & Medicinal Chemistry Letters, 7: 1119-1122; Diederichsen, U., 1998, Bioorganic & Med. Chem. Lett., 8:165-168; Diederichsen et al., 1998, Angew. Chem. mt. Ed., 37: 302-305; Cantin et al., 1997, Tett. Lett., 38: 4211-4214; Ciapetti et al., 1997, Tetrahedron, 53: 1167-1176; Lagriffoule et al., 1997, Chem. Eur. 1. 3: 912-919; Kumar et al., 2001, Organic Letters 3(9): 1269-1272; and the Peptide-Based Nucleic Acid Mimics (PE-NAMs) of Shah et al. as disclosed in WO 96/04000. All of which are incorporated herein by reference.

The oligonucleotides may be single stranded or double stranded, as specified, or contain portions of both double stranded or single stranded sequence. As will be appreciated by those in the art, the depiction of a single strand ("Watson") also defines the sequence of the other strand ("Crick"); thus the sequences described herein also includes the complement of the sequence.

"Protein" has its standard meaning and is intended to refer to at least two covalently attached amino acids, which includes proteins, polypeptides, oligopeptides and peptides. The protein may be made up of naturally occurring amino acids and peptide bonds, or synthetic peptidomimetic structures, i.e., "analogs" such as peptoids [see Simon et al., Proc. Natl. Acad. Sci. U.S.A. 89(20:9367-71 (1992)], generally depending on the method of synthesis. Thus "amino acid", or "peptide residue", as used herein means both naturally occurring and synthetic amino acids. For example, homo-phenylalanine, citrulline, and noreleucine are considered amino acids for the purposes of the invention. "Amino acid" also includes imino acid residues such as proline and hydroxyproline. In addition, any amino acid representing a component of the variant proteins of the present invention can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R— or the S—, depending upon its composition and chemical configuration. Such derivatives generally have the property of greatly increased stability, and therefore are advantageous in the formulation of compounds which may have longer in vivo half lives, when administered by oral, intravenous, intramuscular, intraperitoneal, topical, rectal, intraocular, or other routes.

In some embodiments, the amino acids are in the (S) or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. S218: U138 Part 2 Aug. 22, 1999, both of which are expressly incorporated by reference herein.

"Squamous cell carcinoma" has its standard meaning and is intended to refer to any neoplasm or tumor of epithelial cells.

"Tumorigenesis" has its standard meaning and is intended to refer to the basic developmental processes that produce tumors. These basic properties include the ability to proliferate or invade nearby normal cells and the ability to migrate from the site where the tumor initiated, i.e. metastasis.

The invention finds use in the prevention, treatment, detection or research of squamous cell carcinomas. Carcinomas are malignancies that originate in the epithelial tissues. Epithelial cells cover the external surface of the body, line the internal cavities, and form the lining of glandular tissues. In adults, carcinomas are the most common forms of cancer.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans. Other subjects may include cattle, dogs, cats, guinea pigs, rabbits, rats, mice, horses, and the like.

Exemplary Embodiments

Provided herein are: (1) migration facilitating proteins (MFPs) derived from the laminin-5 α3 chain G4 and/or G5 domains; (2) antibodies which bind to MFPs, thereby inhibiting tumorigenesis of neoplastic epithelial cells; (3) methods for screening for agents, such as antibodies, small molecules, etc., that specifically bind one or more of the MFPs described herein; (4) methods for screening for agents that inhibit squamous cell carcinoma (SCC) tumor development using MFPs, (5) methods for diagnosing SCC; and, (6) methods for determining the efficacy of candidate agents used to treat SCC. All of these inventions rely upon MFPs, nucleic acids that encode MFPs and other molecules, such as antibodies, that bind MFPs.

Laminin-5 (formerly called kalinin, nicein, or BM6000) is a heterotrimeric extracellular matrix protein that is initially synthesized and secreted in an unprocessed form with an α3 chain of 200 kDa, a β3 chain of 140 kDA, and a γ2 chain of 155 kDA. (Marinkovich et al., 1992, J. Biol. Chem., 267: 17900-17906). Laminin-5 is a component of the basal lamina, the structure that provides tissue integrity, as well as the foundation for migration, growth and differentiation of cells. It is therefore not surprising that processes that interfere with wild type functions of laminin-5 produce diseases in humans and other mammals.

Large deposits of laminin-5 are found at the leading edges of squamous cell carcinomas (SCCs). This deposition of laminin-5 is believed to serve as a substrate for tumor invasion (see, e.g., Pyke et al., 1995, Canc. Res. 55: 4132-4139; Berndt et al., 1997, Invasion and Metastasis, 17: 251-258). Increased laminin-5 immunoreactivity is indicative of a poor prognosis in patients with squamous cell carcinoma (SCC). Laminin-5 is also preferentially expressed by invading malignant cells of many human carcinomas in additions to SCCs, colon and mammary carcinomas (Pyke, et al., 1994, Am. J. Pathol. 145(4):782-791) and malignant gliomas (Fukushima et al., 1998, Int. J. Cancer, 76: 63-72).

Processing of extracellular matrix proteins by proteases is emerging as a key mechanisms in processes such as wound healing and tumor metastasis. Several proteases have been implicated in laminin-5-processing (see, e.g., Veitch et al., 2003, J. Biol. Chem., 278: 15661-15668; and U.S. patent Pub. No. 2002/0076736). In fully formed tissues, laminin-5 is completely processed and is devoid of the G4 and G5 domains (Marinkovich et al., 1992, J. Biol. Chem., 267: 17900-17906). Without being bound by theory, it appears that specific proteolytic processing can convert laminin-5 from a pro-migratory signal required for cell migration during tumor invasion and tissue remodeling to an adhesive substrate devoid of the G4 and G5 domains.

Migration Facilitating Sequences

Accordingly, provided herein are polynucleotide and amino acid sequences associated with SCC, herein termed "migration facilitating sequences" or "MFSs". The proteins having the various amino acid sequences are referred to herein as "migration facilitating proteins" or "MFPs". Association in this context means that the amino acid and polynucleotide sequences are either differentially expressed or altered in SCCs or neoplastic epithelial cells as compared to normal epithelial tissue. "SCC" refers herein to any malignant neoplasm or tumor of epithelial cells. Specific examples of epithelial cells include squamous cells, squamous carcinoma cells, keratinocytes, mucosal epithelial cells, such as oral mucosal cells, gastrointestinal epithelial cells, corneal epithelium of the eye, and epithelial cells of the urinary and reproductive tract. Specific examples of SCC carcinomas arising from neoplastic epithelial cells include skin, lung, head, neck, oral, gastric, colorectal, throat, urinary tract, reproductive tract, esophageal, etc.

SCC is commonly sun-induced, i.e., actinically derived SCC. SCC can also result from transplant or invasive surgery, or follow other immunosuppressive situations. Chronic inflammation can lead to development of SCC at the site of inflammation, e.g., a burn or scar, Majolin's ulcer, etc. SCC can be virally induced, for example, SCC can result from human papillomavirus-induced (HPV) infection. SCC can include adenoid (acantholytic) SCC, spindle cell SCC, verrucous carcinoma (VC), keratoacanthoma (KA), nodular SCC periungual SCC, and other epithelial carcinomas.

MFSs can include both polynucleotide and amino acid sequences. In some embodiments, the MFSs are recombinant polynucleotides. By the term "recombinant polynucleotide" herein is meant polynucleotides, originally formed in vitro, in general, by the manipulation of the polynucleotide by polymerases and endonucleases, in a form not normally found in nature. Thus, an isolated polynucleotide, in a linear form, or an expression vector formed in vitro by ligating polynucleotide molecules that are not normally joined, are both considered recombinant for the purposes of this invention. It is understood that once a recombinant polynucleotide is made and reintroduced into a host cell or organism, it will replicate non-recombinantly, i.e. using the in vivo cellular machinery of the host cell rather than in vitro manipulations; however, such polynucleotides, once produced recombinantly, although subsequently replicated non-recombinantly, are still considered recombinant for the purposes of the invention.

As will be appreciated by those in the art, and more fully outlined below, MFSs comprising polynucleotides are useful in a variety of applications, including diagnostic applications, where they can be used as hybridization probes to detect MFSs in SCCs, as well as in therapeutic applications, such as the development of antisense sequences that can be used to affect the expression and activity of MFPs in SCCs.

MFSs include those that are up-regulated, (e.g., expressed at a higher level), as well as those that are down-regulated, (e.g., expressed at a lower level) in SCCs. MFSs also include sequences that have been altered (i.e. truncated sequences or sequences with a one or more mutations, such as point mutations, deletions, insertions, etc.) and show either the same expression profile or an altered profile. In some embodiments, the MFSs are from humans. However, as will be appreciated by a person of skill in the art, MFSs from other organism may be useful in animal models of disease and drug evaluation. Thus, other MFSs are provided. For example, MFSs can be obtained from vertebrates, including mammals, such as rodents (rats, mice, hamsters, guinea pigs, etc.), primates, farm animals (including sheep, goats, pigs, cows, horses, etc), as well invertebrates, such as Drosophila. MFSs from other organisms may be obtained using the techniques outlined below.

In some embodiments, MFSs are those that are altered but show either the same expression profile or an altered profile as compared to normal epithelial tissue of the same differentiation stage. "Altered MFSs" as used herein refers to sequences which are truncated, contain insertions or contain point mutations.

An MFS can be initially identified by substantial nucleic acid and/or amino acid sequence homology to the MFS's outlined herein. Such homology can be based upon the overall oligonucleotide or amino acid sequence, and is generally determined, using either homology programs or hybridization conditions. As is known in the art, a number of different programs are available for determining polynucleotide or amino acid sequence homology including sequence based alignment programs, sequence homology based alignment programs, structural alignment programs etc. Non-limiting examples of sequence-based alignment programs include Smith-Waterman searches (Smith & Waterman, Adv. Appl. Math. 2:482 (1981)), Needleman-Wunsch (Needleman & Wunsch, J. Mol. Biol. 48:443 (1970)), Double Affine Smith-Waterman, frame search, Gribskov/GCG profile search, Gribskov/GCG profile scan, profile frame search, Bucher generalized profiles, Hidden Markov models, Hframe, Double Frame, Blast, Psi-Blast, Clustal, and GeneWise. Sequence homology based alignment methods are described in Altschul et al. (Altschul et al., J. Mol. Biol. 215(3):403 (1990)). Examples of structural alignment programs include VAST from the NCBI; SSAP (Orengo and Taylor, Methods Enzymol 266(617-635 (1996)) SARF2 (Alexandrov, Protein Eng 9(9):727-732. (1996)) CE (Shindyalov and Boume, Protein Eng 11(9):739-747. (1998)); (Orengo et al., Structure 5(8):1093-108 (1997); Dali (Holm et al., Nucleic Acid Res. 26(1):316-9 (1998), Computerized implementations of some of the above described algorithms are also available (e.g., BLASTx, BLAST, GAP, BESTFIT, FASTA, and TFASTA in the Wisconsin Genetics Software Package, Genetics Computer Group, 575 Science Drive, Madison, Wis.); the Best Fit sequence program described by Devereux et al., Nucl. Acid Res. 12:387-395 (1984).

Polynucleotide homology can also be determined through hybridization studies; see for example Maniatis et al., Molecular Cloning: A Laboratory Manual, 2d Edition, 1989, and Short Protocols in Molecular Biology, ed. Ausubel, et al., both of which are hereby incorporated by reference. Generally, stringent conditions are selected, although less stringent hybridization conditions can be used. Typically, stringent conditions are selected to be about 5-10/C lower than the thermal melting point (Tm) for the specific sequence at a defined ionic strength pH. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993).

In some embodiments, MFSs are polynucleotides. Polynucleotides comprising MFSs can be generated from either a full length genomic and/or cDNA polynucleotide encoding a laminin-5 α3 chain. In some embodiments, MFSs are generated from the human α3 chain of laminin-5 (Ryan et al., 1994, J. Biol. Chem., 269: 22779-22787; Gen Bank Accession No. NM.sub.—000227). MFSs of various lengths spanning the G4 and/or G5 domains can be generated. For example, an polynucleotide spanning a subdomain of the G4 domain of the human α3 chain of laminin-5 can be generated by starting at nucleotide position 4196 and ending at nucleotide 4588. An oligonucleotide spanning the G5 domain of the human α3 chain of laminin-5 can be generated by starting at nucleotide position 4590 and ending at nucleotide 5140. An oligonucleotide spanning a subdomain of the G4 domain and the entire G5 domain of the human α3 chain of laminin-5 can be generated by starting at nucleotide position 4196 and ending at nucleotide 5140.

The exact number of nucleotides or nucleotide analogs chosen will vary depending on the sequence of the nucleotides selected and the presence of nucleotides encoding amino acids that comprise antigenic determinants. By "epitope" or "determinant" "or antigenic determinant" herein is meant a portion of a protein that can generate and/or bind an antibody or T-cell receptor in the context of MHC. For example, the presence of antigenic determinants within the G4 and G5 domains can be identified by searching databases for MHC ligands and peptide motifs (Rammensee, H., et al. (1999) Immunogenetics, 50:213-219). This information can be used to generate MFSs comprising MHC epitopes. Typically, epitopes recognized by MHC class I molecules comprise between 8 and 11 amino acids, thus, an MFS encoding an MHC class I epitope can range between 24 to 33 nucleotides. Viral peptides recognized by MHC class II molecules comprise between 10 to 20 amino acids, thus, an MFS encoding an MHC class II epitope can range between 30 to 60 nucleotides (Fundamental Immunology, 4th edition, W. E. Paul, ed., Lippincott-Raven Publishers, 1999, Chapter 39, pp 1295-1334). In other embodiments, MFSs range between 24 to 1050, or from 60 to 300 nucleotides, or from 60 to 405 nucleotides, or from 60 to 555 nucleotides, or from 60 to 600 nucleotides, or from 60 to 750 nucleotides, or from 60 to 900 nucleotides or from 60 to 1050 nucleotides. In yet other embodiments, MFSs range from 150 to 300 nucleotides, or from 150 to 405 nucleotides, or from 150 to 450 nucleotides, or from 150 to 525 nucleotides, or from 150 to 600 nucleotides, or from 150 to 750 nucleotides, or from 150 to 1050 nucleotides, or from 300 to 600 nucleotides, or from 300 to 900 nucleotides, or from 300 to 1050 nucleotides.

Migration Facilitating Proteins

In some embodiments, "migration facilitating proteins" or "MFPs" are generated from the amino acid sequence encoding the laminin-5 α3 G4 and/or G5 domains or subdomains thereof. "MFPs" are proteins that are capable of supporting migration of nearby tissue or tissue located at distal points in the body by neoplastic epithelial cells. MFPs also can be recombinant. A "recombinant MFP protein" is a protein made using recombinant techniques, i.e. through the expression of a recombinant oligonucleotide as described above. A recombinant protein is distinguished from a naturally occurring protein by at least one or more characteristics. For example, the protein may be isolated or purified away from some or all of the proteins and compounds with which it is normally associated in its wild type host, and thus may be substantially pure. Generally, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an MFP from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In some embodiments, MFPs are generated from the G4 and G5 domains of the human α3 chain of laminin-5 (see FIG. 1A). MFPs of various lengths spanning the G4 and/or G5 domains can be generated. FIG. 1B illustrates an exemplary embodiment of the generation of MFPs from the G4 domain. As illustrated in FIGS. 1B-D, a number of MFPs can be generated from the G4 and/or G5 domains comprising varying numbers of amino acids or amino acid analogs. The exact number of amino acids or amino acid analogs chosen will vary depending on the sequence of the amino acids selected, the presence of bone morphogenetic-1 cleavage sites, and the presence of amino acids comprising antigenic determinants.

As discussed above, the presence of antigenic determinants within the G4 and G5 domains can be identified by searching databases for MHC ligands and peptide motifs (Rammensee, H., et al. (1999) Immunogenetics, 50:213-219). This information can be used to identify MHC epitopes. Typically, epitopes recognized by MHC class I molecules comprise between 8 and 11 amino acids while epitopes recognized by MHC class II molecules comprise between 10 to 20 amino acids (Fundamental Immunology, 4th edition, W. E. Paul, ed., Lippincott-Raven Publishers, 1999, Chapter 39, pp 1295-1334). Thus, in some embodiments, MFPs range between 8 to 11. In other embodiments, MFPs range between 10 to 20 amino acids. In other embodiments, MFPs range from 8 to 350 amino acids. In still other embodiments, MFPs range between 20 to 100 amino acids, or from 20 to 135 amino acids, or from 20 to 185 amino acids, or from 20 to 200 amino acids, or from 20 to 250 amino acids, or from 20 to 300 amino acids or from 20 to 350 amino acids. In yet other embodiments, MFPs range from 50 to 100 amino acids, or from 50 to 135 amino acids, or from 50 to 150 amino acids, or from 50 to 175 amino acids, or from 50 to 200 amino acids, or from 50 to 250 amino acids, or from 50 to 350 amino acids, or from 100 to 200 amino acids, or from 100 to 300 amino acids, or from 100 to 350 amino acids.

The MFPs may be unprocessed or processed. As used herein "unprocessed" refers to an MFP that is still associated with the laminin-5 α3 chain. By "processed" herein is meant that the MFP is dissociated from the laminin-5 α3 chain.

FIG. 1B illustrates an exemplary embodiment of MFPs that can be generated from the G4 domain. FIG. 1B depicts 3 MFPs: MFP 1, MFP 2, And MFP 3. Known cleavage sites for bone morphogenetic protein-1 (BMP-1) are indicated by the solid boxes labeled 1a, 1b, and 1c (see U.S. patent Pub. No. 2002/0076736). As illustrated in FIG. 1B, the MFPs described herein do not comprise cleavage sites for bone morphogenetic protein-1 (BMP-1) or related BMP-1 proteins. As will be appreciated by a skilled artisan, other MFPs (MFPs 4) can be generated from the G4 domain, comprising from 8 up to 130 amino acids.

FIG. 1C illustrates an exemplary embodiment of MFPs that can be generated from the G5 domain. As illustrated in FIG. 1C, one MFP can be made, i.e. MFP 5 spanning the entire G5 domain. In other embodiments one MFP can be made, i.e. MFP 6, which spans a subdomain of the G5 domain. Alternatively, a number of MFPs, i.e. MFPs 7, can be made comprising from 8 up to 182 amino acids.

FIG. 1D illustrates an exemplary embodiment of MFPs that can be generated from the G5 and the G5 domain. As illustrated in FIG. 1D, one MFP can be made, i.e. MFP 8, spanning the G4-G5 domain. As illustrated in FIG. 1D, MFP 8 does not contain cleavage sites for BMP-1 or related BMP-1 proteins. Alternatively, a number of MFPs, i.e., MFPs 9, can be made comprising from 8 up to 315 amino acids.

Expression Systems

MFSs polynucleotides encoding MFPs can be used to make a variety of expression vectors to express MFPs which can then be used in the diagnostic, screening and therapeutic applications described below. The expression vectors may be either self-replicating extrachromosomal vectors or vectors which integrate into a host genome. Generally, these expression vectors include transcriptional and translational regulatory nucleic acid operably linked to the oligonucleotide encoding the MFP protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

An oligonucleotide is "operably linked" when it is placed into a functional relationship with another oligonucleotide sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice. The transcriptional and translational regulatory nucleic acid will generally be appropriate to the host cell used to express the MFP protein; for example, transcriptional and translational regulatory nucleic acid sequences from *Bacillus* are preferably used to express the MFP protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

MFPs are produced by culturing a host cell transformed with an expression vector containing an oligonucleotide encoding an MFP, under the appropriate conditions to induce or cause expression of the MFP. The conditions appropriate for MFP expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect, plant and animal cells, including mammalian cells. Of particular interest are primary human keratinocytes, although other cells also can be used, i.e. *Drosophila melanogaster* cells, *Saccharomyces cerevisiae* and other yeasts, *E. coli, Bacillus subtilis,* 293 cells, CHO, other human cell and cell lines.

In some embodiments, the MFPs are expressed in mammalian cells. Mammalian expression systems are also known in the art, and include retroviral systems. A preferred expression vector system is a retroviral vector system such as is generally described in Dajee et al., 2003, Nature, 421: 639-643, which is incorporated herein by reference in its entirety. Of particular use as mammalian promoters are the promoters from mammalian viral genes, since the viral genes are often highly expressed and have a broad host range. Examples include, but are not limited to, the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenlytion signals include those derived form SV40.

For example, the full length laminin-5 α3 cDNA can be ligated into a pENTR1A.™. vector (Invitrogen). The full length laminin-5 α3 cDNA can be cleaved and the PCR used to obtain a MF oligonucleotide sequence from the G4 and/or G5 domain. The resulting PCR product can be ligated into a pENTR1A™ vector and the cloning product confirmed by sequencing. The cloned product can then be transferred from the pENTR1A™ vector to a Gateway adapted LSRZ retroviral vector through lambda phage recombination. See Dajee et al., 2003, Nature, 421: 639-643.

In some embodiments, MFPs are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the MFP in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris,* and *Streptococcus lividans,* among others. The bacterial expression vectors are transformed into bacterial host cells using techniques well known in the art, such as calcium chloride treatment, electroporation, and others.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

MFS's and MFPs can be identified as described in the examples. For example, in a specific embodiment, various oligonucleotides can be generated from the G4 and G5 domain of the human laminin-5 α3 and subcloned into a retroviral vector. The resulting retroviral vectors can be transduced into cell cultures and the cells analyzed for cell scattering and cell migration (see e.g., Examples and FIGS. 5 and 6; see also Ryan, et al., 1994, J. Biol. Chem., 269: 22779-22787). Alternatively, laminin-5 negative primary human keratinocytes co-expressing Ras, a stable NF-κB repressor mutant of IκBα (i.e. IKB), and one or more MFS(s) can be retrovirally transduced and used to regenerate human skin on immune deficient mice.(i.e. nude mice). The subsequent development of neoplasms can be monitored and compared to wild type mice (see e.g., Examples, FIG. 7; and Dajee et al., 2003, Nature, 421:639-643).

In some embodiments, matrigel, which contains heparin sulfate proteoglycan, is used as a matrix for the suspension of RAS/IKB transformed keratinocytes prior to subcutaneous injection into nude mice. In other embodiments, MFPs can be suspended in matrigel prior to injection of RAS/IKB transformed keratinocytes.

In some embodiments, MFPs are purified or isolated after expression. MFPs may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the MFP may be purified using a standard anti-MFP antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the MFP protein. In some instances no purification will be necessary.

Antisense Sequences

The MFSs and MFPs can be used in a variety of different ways. In some embodiments, MFSs can be used to make antisense therapeutic agents that affect the expression and activity of MFPs. Antisense technology relies on the modulation of expression of a target protein through the specific binding of an antisense sequence to a target sequence encoding the target protein or directing its expression. (See, e.g., Agrawal, S., ed., 1996, Antisense Therapeutics, Humana Press Inc., Totawa N. J.; Alama et al. (1997) Pharmacol Res. 36(3):171-178; Crooke, S. T., 1997, Adv. Pharmacol. 40:1-49; and Lavrosky et al., 1997, Biochem. Mol. Med. 62(1):11-22.). Antisense sequences are nucleic acid sequences capable of specifically hybridizing to at least a portion of a target sequence. Antisense sequences can bind to cellular mRNA or genomic DNA, blocking translation or transcription and thus interfering with expression of a targeted protein product. Antisense sequences can be any nucleic acid material, including DNA, RNA, or any nucleic acid mimics or analogs. (See, e.g., Rossi et al., 1991, Antisense Res. Dev. 1(3):285-288; Pardridge et al., 1995, Proc. Nat. Acad. Sci. 92 (12):5592-5596; Nielsen, P. E. and G. Haaima, 1997, Chem. Soc. Rev. 96:73-78; and Lee et al., 1998, Biochemistry 37 (3):900-1010.). Delivery of antisense sequences can be accomplished in a variety of ways, such as through intracellular delivery using an expression vector. Site-specific delivery of exogenous genes is also contemplated, such as techniques in which cells are first transfected in culture and stable transfectants are subsequently delivered to the target site.

Typically, antisense oligonucleotides between 15 to 25 nucleobases or nucleobase analogs are capable of producing the desired therapeutic effect, i.e., direct disruption of translation of an MFP. In addition, chemically reactive groups, such as iron-linked ethylenediamine-tetraacet-ic acid (EDTA-Fe), can be attached to antisense oligonucleotides, causing cleavage of the RNA at the site of hybridization. These and other uses of antisense methods to inhibit the in vitro translation of genes are well known in the art (see, e.g., Marcus-Sakura (1988) Anal. Biochem. 172:289).

In some embodiments, antisense oligonucleotides are designed such that they disrupt the translation of the laminin-5 α3 chain. In other embodiments, antisense oligonucleotides are designed such that they disrupt the translation of an MFP from the G4 domain or subdomain thereof. In still other embodiments, antisense oligonucleotides are designed such that they disrupt the translation of an MFP from the G5 domain or subdomain thereof. In yet other embodiment, antisense oligonucleotides are designed such that they disrupt the translation of an MFP from the G4 and G5 domain or subdomain thereof.

Delivery of antisense agents can be achieved intracellularly through using a recombinant expression vector such as a chimeric virus or a colloidal dispersion system which, upon transcription, produces a sequence complementary to at least a portion of the cellular sequence encoding the target protein (see, e.g., Slater et al., 1998, J. Allergy Cli. Immunol. 102 (3): 469-475). Delivery of antisense sequences can also be achieved through various viral vectors, including retrovirus and adeno-associated virus vectors. (See, e.g., Miller, 1990, Blood, 76: 271; and Uckert and Walther, 1994, Pharacol. Ther., 63(3): 323-347). Suitable viral vectors include, but are not limited to, adenoviruses, herpes viruses, vaccinia, and RNA viruses such as retroviruses.

Retroviral vectors can be derivatives of murine or avian retrovirus. Retroviral vectors can be made target-specific by inserting, for example, a polynucleotide encoding a protein or proteins such that the desired ligand is expressed on the surface of the viral vector. The ligand can be a glycolipid carbohydrate or protein. Preferred targeting can also be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide. See, e.g, WO 91/04753.

Other delivery mechanisms that can be used for delivery of antisense sequences to target cells include colloidal dispersion and liposome-derived systems, artificial viral envelopes, and other systems available to one of skill in the art (see, e.g., Rossi, 1995, Br. Med. Bull. 51 (1): 217-225; Morris et al., 1997, Nucl. Acids Res. 25 (14): 2730-2736; Boado et al., 1998, J. Pharm. Sci. 87 (11): 1308-1315; and WO 90/10448). For example, delivery systems can make use of macromolecule complexes, nanocapsules, microspheres, beads, and lipid-based systems including oil-in-water emulsions, micelles, mixed micelles, and liposomes.

Antibodies

In some embodiments, the MFPs are used to generate antibodies that can be used in the screening and therapeutic applications described herein. Preferably, the MFP should comprise at least one epitope or determinant. In some embodiments, the epitope is unique; that is, antibodies generated to a unique epitope show little or no cross-reactivity.

Within the context of the present invention, antibodies are understood to include monoclonal antibodies and polyclonal antibodies, antibody fragments (e.g., Fab and F(ab')$_2$), chimeric antibodies bifunctional or bispecific antibodies and tetrameric antibody complexes. Antibodies are understood to be reactive against a selected antigen on the surface of a T cell if they bind with an appropriate affinity (association constant), e.g. greater than or equal to $10^7 M^{-1}$. Additionally, antibodies that may be used in the methods of the present invention may also be described or specified in terms of their binding affinities include those with a dissociation constant of Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-9}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, $10^{-15}$ M.

MFPs can be evaluated to determine regions of immunogenicity. As discussed above, methods of analysis and epitope selection are well-known in the art. Analysis and selection can also be accomplished, for example, by various software packages, such as LASERGENE NAVIGATOR software (DNASTAR; Madison, Wis.). The polypeptides or fragments used to induce antibodies should be antigenic, but need not necessarily be biologically active. An antigenic fragment or polypeptide is at least 5 amino acids in length, more preferably, at least 10 amino acids in length, and most preferably, at least 15 amino acids in length. It is preferable that the antibody-inducing fragment or polypeptide is identical to at least a portion of the amino acid sequence of the G4 and/or G5 domain, or subdomains thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor, and antibodies can be produced against the chimeric molecule.

Methods for the production of antibodies are well-known in the art. For example, various hosts, including goats, rabbits, rats, mice, humans, and others, may be immunized by injection with the MFP or any immunogenic fragment or peptide thereof. Depending on the host species, various adjuvants may be used to increase immunological response. Such adjuvants include, but are not limited to, Freund's adjuvant, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

Monoclonal and polycolonal antibodies can be prepared using any technique which provides for the production of antibody molecules by continuous cell lines in culture. Techniques for in vivo and in vitro production are well-known in the art (see, e.g., Pound, J. D., 1998, Immunochemical Protocols, Humana Press, Totowa N. J.; Harlow, E. and D. Lane, 1988, Antibodies, A Laboratory Manual, Cold Spring Harbor Laboratory, New York). The production of chimeric antibodies is also well-known, as is the production of single-chain antibodies (see, e.g., Morrison et al., 1984, Proc. Natl. Acad. Sci. 81: 6851-6855; Neuberger et al., 1984, Nature, 312: 604-608; Takeda et al., 1985, Nature, 314: 452-454). Antibodies with related specificity, but of distinct idiotypic composition, may be generated, for example, by chain shuffling from random combinatorial immunoglobin libraries (see, e.g., Burton, 1991, Proc. Natl. Acad. Sci. 88: 11120-11123).

Antibodies may also be produced by inducing in vivo production in the lymphocyte population or by screening immunoglobulin libraries or panels of highly specific binding reagents (see, e.g., Orlandi et al., 1989, Proc. Natl. Acad. Sci. 86: 3833-3837; Winter, G. and C. Milstein, 1991, Nature, 349: 293-299). Antibody fragments which contain specific binding sites for the target polypeptide may also be generated. Such antibody fragments include, but are not limited to, F(ab').sub.2 fragments, which can be produced by pepsin digestion of the antibody molecule, and Fab fragments, which can be generated by reducing the disulfide bridges of the F(ab').sub.2 fragments. Alternatively, Fab expression libraries may be constructed to allow rapid and easy identification of monoclonal Fab fragments with the desired specificity (see, e.g., Huse et al., 1989, Science, 254: 1275-1281).

In some embodiments, the antibodies are bispecific antibodies. Bispecific antibodies are monoclonal, preferably human or humanized, antibodies that have binding specificities for at least two different antigens. In the present case, one of the binding specificities is for a MFP, and the other one is for any other antigen, such as a cell-surface protein or receptor or receptor subunit, preferably one that is tumor specific.

In some embodiments, the antibodies to MFPs are humanized antibodies. Humanized forms of non-human (e.g., murine) antibodies are chimeric molecules of immunoglobulins, immunoglobulin chains or fragments thereof (such as Fv, Fab, Fab', F(ab')$_2$ or other antigen binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general,.the humanized antibody will comprise substantially all of at least one, and typically two, variable domains, in which all or substantially all of the CDR regions correspond to those of a non-human immunoglobulin and all or substantially all of the framework residues (FR) regions are those of a human immunoglobulin consensus sequence. The humanized antibody optimally also will comprise at least a portion of an immunoglobulin constant region (Fc), typically that of a human immunoglobulin (Jones et al., 1986, Nature, 321: 522-525; Riechmann et al., 1988, Nature, 332: 323-329; and Presta, 1992, Curr. Op. Strucf. Biol., 2: 593-596).

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (Jones et al., 1986, Nature, 321: 522-525; Riechmann et al., 1988, Nature, 332: 323-329; Verhoeyen et al., 1988, Science, 239: 1534-1536), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, 1991, J. Mol. Biol., 227: 381; Marks et al., 1991, J. Mol. Biol., 222: 581). The techniques of Cole et al. and Boemer et al. are also available for the preparation of human monoclonal antibodies (Cole et al., 1985, Monoclonal Antibodies and Cancer Therapy, Alan R. Liss, p. 77, and Boemer et al., 1991, J. Immunol., 147(1): 86-95). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., 1992, Bio/Technology, 10: 779-783; Lonberg et al., 1994, Nature, 368: 856-859; Morrison, 1994, Nature, 368: 812-13; Fishwild et al., 1996, Nature Biotechnology, 14: 845-51; Neuberger, 1996, Nature Biotechnology, 14: 826; Lonberg and Huszar, 1995, Intern. Rev. Immunol. 13 65-93.

Antibodies can be tested for anti-MFP activity using a variety of methods well-known in the art. Various techniques may be used for screening to identify antibodies having the desired specificity, including various immunoassays, such as enzyme-linked immunosorbent assays (ELISAs), including direct and ligand-capture ELISAs, radioimmunoassays (RIAs), immunoblotting, and fluorescent activated cell sorting (FACS). Numerous protocols for competitive binding or immunoradiometric assays, using either polyclonal or monoclonal antibodies with established specificities, are well known in the art (see, e.g., Harlow and Lane, supra). Such immunoassays typically involve the measurement of complex formation between the target polypeptide and a specific antibody. A two-site, monoclonal-based immunoassay utilizing monoclonal antibodies reactive to two non-interfering epitopes on the target polypeptide is preferred, but other assays, such as a competitive binding assay, may also be employed (see, e.g. Maddox et al., 1983, J Exp Med, 158: 1211).

Once made, the antibodies can be used to identify MFPs in a sample, e.g., from biopsied tissue, etc. The amount of MFPs or mRNAs encoding MRPs can be determined using methods well known in the art, including but not limited to, quantitative image analysis, and reverse transcriptase polymerase chain reaction (RT-PCR) using portions of the biopsied tissue. Quantitation of mRNA corresponding to MFPs, can be determined by a competition reaction using equal volumes of the patient sample run against a series of decreasing known concentrations, e.g., of a mimic or mutant cDNA fragment.

MFP antibodies as described herein, are capable of specifically binding to MFPs. By "specifically binding" herein is meant that the antibodies bind to the protein with a binding constant in the range of at least $10^{-4}$-$10^{-9}$ $M^{-1}$, preferably in the range of $10^{-4}$-$10^{-6}$ $M.^{-1}$, with a preferred range being $10^{7}$-$10^{-9}$ $M^{-1}$.

In some embodiments, antibodies to MFPs are capable of reducing or eliminating the biological activity or function of the MFP(s). That is, the addition of anti-MFP antibodies (i.e., polyclonal or monoclonal) to SCC or neoplastic epithelial cells expressing a MFP reduces or eliminates the MFP activity. Generally, at least a 25% decrease in activity is preferred, with at least about 50% being particularly preferred and about a 95-100% decrease being especially preferred.

In some embodiments, antibodies to MFPs are conjugated to a therapeutic moiety. For example, the therapeutic moiety can be an agent that inhibits enzymatic activity such as protease or protein kinase activity associated with SCC. In other embodiments, the therapeutic moiety can be a cytotoxic agent. Cytotoxic agents are numerous and varied and include, but are not limited to, radiochemicals, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like.

Squamous Cell Carcinomas

Squamous cells are flat cells which form the surface of an epithelium. They can be identified histologically by the fact that they look flattened and thin under a microscope. Epithelia lined by squamous cells can be classified as either simple squamous epithelium or stratified squamous epithelium.

Squamous cell carcinoma is a carcinoma that may occur in many different organs, including the skin, mouth, esophagus, lungs, and cervix. It is a malignant tumor of epithelium that shows squamous cell differentiation. Squamous cell carcinoma is usually developed in the epithelial layer of the skin and sometimes in various mucous membranes of the body. This type of cancer can be seen on the skin, lips, inside the mouth, throat or esophagus.

The most common noncutaneous tumor of the head and neck is squamous cell carcinoma of the larynx, followed by squamous cell carcinomas of the palatine tonsil, tongue, and floor of the mouth. Somewhat less common are tumors of the salivary gland, jaw, nose and paranasal sinuses, and ear. Tumors of the thyroid gland, eye, and skin are discussed elsewhere in the manual. Excluding the skin and thyroid gland, >90% of head and neck cancers are squamous cell (epidermoid) carcinomas, and 5% are melanomas, lymphomas, and sarcomas. The Epstein-Barr virus plays a role in the pathogenesis of nasopharyngeal cancer.

Oral squamous cell carcinoma affects about 30,000 Americans each year. Oral squamous cell carcinoma is the most common oral or pharyngeal cancer. The chief risk factors for oral squamous cell carcinoma are smoking and alcohol use. Squamous cell carcinoma of the tongue may also result from Plummer-Vinson syndrome, syphilis, or chronic trauma. About 40% of intraoral squamous cell carcinomas begin on the floor of the mouth or on the lateral and ventral surfaces of the tongue. About 38% of all oral squamous cell carcinomas occur on the lower lip, and about 11% begin in the palate and tonsillar area.

About 90% of vulvar cancers are squamous cell carcinomas; about 5% are melanomas. Vulvar cancer most often occurs in elderly women. It usually. manifests as a palpable lesion. Diagnosis is by biopsy. Treatment includes excision and inguinal and femoral lymph node dissection. Vulvar cancer accounts for about 3 to 4% of gynecologic cancers in the US. Average age at diagnosis is about 70, and incidence increases with age. Risk factors include vulvar intraepithelial neoplasia (VIN), human papillomavirus infection, heavy cigarette smoking, lichen sclerosus, squamous hyperplasia, squamous carcinoma of vagina or cervix, and chronic granulomatous diseases. VIN is a precursor to vulvar cancer. VIN may be multifocal. Sometimes adenocarcinoma of the vulva, breast, or Bartholin's glands also develops.

Squamous cell carcinoma of the skin is a malignant tumor of epidermal keratinocytes that invades the dermis, usually occurring in sun-exposed areas. The incidence in the US is 80,000 to 100,000 cases annually, with 2000 deaths. Local destruction may be extensive, and metastases occur in advanced stages. Diagnosis is by biopsy. Treatment depends on the tumor's characteristics and may involve curettage and electrodesiccation, surgical excision, cryosurgery, or, occasionally, radiation therapy.

The clinical appearance is highly variable, but any non-healing lesion on sun-exposed surfaces should be suspect. The tumor may begin as a red papule or plaque with a scaly or crusted surface and may become nodular, sometimes with a warty surface. In some, the bulk of the lesion may lie below the level of the surrounding skin. Eventually the tumor ulcerates and invades the underlying tissue. The percentage of squamous cell carcinomas on sun-exposed skin that metastasize is quite low. However, about ⅓ of lingual or mucosal cancers have metastasized before diagnosis.

About 80 to 85% of all cervical cancers are squamous cell carcinoma. Diagnosis is by screening cervical Papanicolaou (Pap) test and biopsy. Staging is clinical. Treatment usually includes surgical resection, radiation therapy, and, unless cancer is localized, chemotherapy; if cancer is widely metastasized, treatment is primarily chemotherapy. Cervical cancer results from cervical intraepithelial neoplasia (CIN), which appears to be caused by infection with human papillomavirus (HPV) type 16, 18, 31, 33, 35, or 39.

CIN is graded as 1 (mild cervical dysplasia), 2 (moderate dysplasia), or 3 (severe dysplasia and carcinoma in situ). CIN 3 is unlikely to regress spontaneously; if untreated, it may, over months or years, penetrate the basement membrane, becoming invasive carcinoma. Invasive cervical cancer usually spreads by direct extension into surrounding tissues or via the lymphatics to the pelvic and para-aortic lymph nodes. Hematogenous spread is possible.

In squamous cell carcinoma, distant metastases usually occur only when the cancer is advanced or recurrent. The 5-yr survival rates are 80 to 90% with stage I, 50 to 65% with stage II, 25 to 35% with stage III, and 0 to 15% with stage IV. Nearly 80% of recurrences manifest within 2 yr. Adverse prognostic factors include lymph node involvement, large tumor size and volume, deep cervical stromal invasion, parametrial invasion, vascular space invasion, and nonsquamous histology.

Diagnosis and Therapy

The MFSs and MFPs can be used in a variety of different ways. For example, the MFSs and MFPs can be used in diagnostic assays, screening assays, and in therapeutic application. In some embodiments, the MFPS and antibodies to MFPs are used as diagnostic markers for the detection of SCC. Detection of MFPs in putative SCC tissue or patients allows for a determination or diagnosis of SCC. To detect or diagnose SCC, baseline values for the expression or activity of MFPs are established in order to provide a basis for the diagnosis and/or prognosis of SCC in a patient. In some embodiments, this is accomplished by combining body fluids, tissue biopsies, or cell extracts taken from normal subjects with one or more antibody(ies) to a MFP under conditions suitable for complex formation. Such conditions are well known in the art. The amount of standard complex formation may be quantified by comparing levels of antibody-target complex in the normal sample with a dilution series of positive controls, in which a known amount of antibody is combined with known concentrations of purified MFP. Standard values obtained from normal samples may be compared with values obtained from samples from subjects suspected of having SCC. Deviation between standard and subject values establishes the presence of or predisposition to the disease state.

In other embodiments, the expression levels of genes are determined for different cellular states in the SCC phenotype; that is, the expression levels of genes in normal tissue and in SCC tissue are evaluated to provide expression profiles. An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed: does tissue from a particular patient have the gene expression profile of normal or SCC tissue.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, normal versus lymphoma tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, Nature Biotechnology, 14:1675-1680 (1996), hereby expressly incorporated by reference. Other techniques include, but are not limited to, quantitative reverse transcriptase PCR, Northern analysis and RNase protection. As outlined above, preferably the change in expression (i.e. upregulation or downregulation) is at least about 50%, more preferably at least about 100%, more preferably at least about 150%, more preferably, at least about 200%, with from 300 to at least 1000% being especially preferred.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the MF protein and standard immunoassays (ELISAs, etc.) or other techniques, including mass spectroscopy assays, 2D gel electrophoresis assays, etc. Thus, the proteins corresponding to MF genes, i.e. those identified as being important in a SCC phenotype, can be evaluated in a SCC diagnostic test.

Numerous methods known to those of ordinary skill in the art find use in diagnosing SCC; For example, in some embodiments, proteins can be obtained from a sample or a patient are separated by electrophoresis on a gel (typically a denaturing and reducing protein gel, but may be any other type of gel including isoelectric focusing gels and the like). Following separation of the proteins, MFPs can be detected by immunoblotting with antibodies raised against the MFPs. Methods of immunoblotting are well known to those of ordinary skill in the art.

In some embodiments, antibodies to the MFPs find use in in situ imaging techniques. In this method cells are contacted with from one to many antibodies to MFP(s). Following washing to remove non-specific antibody binding, the presence of the antibody or antibodies is detected. In one embodiment the antibody is detected by incubating with a secondary antibody that contains a detectable label. In another method the primary antibody to the MFP(s) contains a detectable label. In another preferred embodiment each one of multiple primary antibodies contains a distinct and detectable label. This method finds particular use in simultaneous screening for a plurality of MFPs. As will be appreciated by one of ordinary skill in the art, numerous other histological imaging techniques are useful in the invention.

In some embodiments the label is detected in a fluorometer which has the ability to detect and distinguish emissions of different wavelengths. In addition, a fluorescence activated cell sorter (FACS) can be used in the method.

In some embodiments, in situ hybridization of labeled MF nucleic acid probes to tissue arrays is done. For example, arrays of tissue samples, including SCC tissue and/or normal tissue, are made. In situ hybridization as is known in the art can then be done.

It is understood that when comparing the expression fingerprints between an individual and a standard, the skilled artisan can make a diagnosis as well as a prognosis. It is further understood that the genes which indicate the diagnosis may differ from those which indicate the prognosis.

In one embodiment, the MF proteins, antibodies, nucleic acids, and cells containing MF sequences are used in prognosis assays. In some embodiments, gene expression profiles can be generated that correlate to SCC severity, in terms of long term prognosis. Again, this may be done on either a protein or gene level, with the use of genes being preferred. In some embodiments, MF probes are attached to solid supports for the detection and quantification of MF sequences in a tissue or patient. The assays proceed as outlined for diagnosis.

The efficacy of therapeutic agents, such as antibodies and/or other candidate drugs also can be determined using the diagnostic assays described above. As will be appreciated by a person of skill in the art, assays to determine the efficacy of a therapeutic agent require the establishment of baseline values. In some embodiments, this is accomplished by combining body fluids, tissue biopsies, or cell extracts taken from a patient with SCC prior to treatment with the candidate drug with one or more antibody(ies) to a MFP under conditions suitable for complex formation. Such conditions are well known in the art. The amount of standard complex formation may be quantified by comparing levels of antibody-target complex in the normal sample with a dilution series of positive controls, in which a known amount of antibody is combined with known concentrations of purified MFP. Standard values obtained from a patient before treatment may be compared with values obtained from a patient after treatment. Deviation between standard and subject values establishes the efficacy of the drug.

Screening Assays

In some embodiments, the MF proteins, antibodies, nucleic acids, and cells containing the MF proteins are used in screening assays. For example, screens for agents that modulate the SCC phenotype can be run. This can be done by screening for modulators of gene expression or for modulators of protein activity at the individual gene or protein level or by evaluating the effect of drug candidates on a "gene expression profile". In some embodiments, the expression profiles are used in conjunction with high throughput screening techniques to allow monitoring for expression profile genes after treatment with a candidate agent (see Zlokamik, et al., 1998, Science, 279: 84-8).

"Modulation" includes both an increase and a decrease in gene expression or activity. The preferred amount of modulation will depend on the original change of the gene expression in normal versus tumor tissue, with changes of at least 10%, preferably 50%, more preferably 100-300%, and in some embodiments 300-1000% or greater. If a gene exhibits a 4 fold increase in tumor compared to normal tissue, a decrease of about four fold is desired; a 10 fold decrease in tumor compared to normal tissue gives a 10 fold increase in expression for a candidate agent is desired, etc.

As will be appreciated by those in the art, this may be done by evaluation at either the gene or the protein level; that is, the amount of gene expression may be monitored using nucleic acid probes and the quantification of gene expression levels, or, alternatively, the level of the gene product itself can be monitored, for example through the use of antibodies to the MFPd and standard immunoassays. Alternatively, binding and bioactivity assays with the protein may be done as outlined below.

In some embodiments, gene expression monitoring is done and a number of genes, i.e. an expression profile, are monitored simultaneously. If desired, multiple protein expression monitoring can be done as well. In embodiments monitoring multiple genes or proteins, the corresponding MF probes are immobilized to solid supports. It is understood that immobilization can occur by any means, including for example; by covalent attachment, by electrostatic immobilization, by attachment through a ligand/ligand interaction, by contact or by depositing on the surface. "Solid support" or "solid substrate" refers to any solid phase material upon which a MF sequence, MFP, or antibody is synthesized, attached, ligated or otherwise immobilized. A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, a gel, or a surface. Surfaces may be planar, substantially planar, or non-planar. Solid supports may be porous or non-porous, and may have swelling or non-swelling characteristics. A solid support may be configured in the form of a well, depression or other container, vessel, feature or location. A plurality of solid supports may be configured in an array at various locations, addressable for robotic delivery of reagents, or by detection means including scanning by laser illumination and confocal or deflective light gathering.

Generally, a candidate bioactive agent is added prior to analysis. The term "candidate bioactive agent" or "drug candidate" or grammatical equivalents as used herein describes any molecule, e.g., protein, oligopeptide, small organic or inorganic molecule, polysaccharide, polynucleotide, etc., to be tested for bioactive agents that are capable of directly or indirectly altering either the SCC phenotype, binding to and/or modulating the bioactivity of an MFP, or the expression of a MF sequence. In a particularly preferred embodiment, the candidate agent suppresses a SCC phenotype, for example to a normal tissue fingerprint. Generally a plurality of assay mixtures are run in parallel with different agent concentrations to obtain a differential response to the various concentrations. Typically, one of these concentrations serves as a negative control, i.e., at zero concentration or below the level of detection.

In one aspect, a candidate agent will neutralize the effect of an MFP. By "neutralize" is meant that activity of a protein is either inhibited or counter acted against so as to have substantially no effect on a cell.

Candidate agents encompass numerous chemical classes, though typically they are organic or inorganic molecules, preferably small organic compounds having a molecular weight of more than 100 and less than about 2,500 daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, proteins, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In assays for altering the expression profile of one or more MF sequences, after the candidate agent has been added and the cells allowed to incubate for some period of time, the sample containing the MF sequences to be analyzed is added to a solid support. If required, the MF sequence is prepared using known techniques. For example, the sample may be treated to lyse the cells, using known lysis buffers, electroporation, etc., with purification and/or amplification such as PCR occurring as needed, as will be appreciated by those in the art.

Generally, one of the assay components is labeled to provide a means of detecting the binding complex of interest. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the MF nucleic acids, proteins and antibodies at any position. For example, the label should be capable of producing, either directly or indirectly, a detectable signal. The detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., 1962, Nature, 144: 945; David et al., 1974, Biochemistry, 13: 1014; Pain et al., 1981, J. Immunol. Meth., 40: 219; and Nygren, 1982, J. Histochem. and Cytochem., 30: 407. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. As known in the art, unbound labeled streptavidin is removed prior to analysis.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545, 730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference.

A variety of hybridization conditions may be used in the present invention, including high, moderate and low stringency conditions as outlined above. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target. In addition, either solid phase or solution based (i.e., kinetic PCR) assays may be used.

Once the assay is run, the data is analyzed to determine the expression levels, and changes in expression levels as between states, of individual genes, or individual proteins, forming an expression profile.

In some embodiments, screening is done to alter the biological function of the expression product of an MF gene. Again, having identified the importance of a gene in a particular state, screening for agents that bind and/or modulate the biological activity of the gene product can be run as is more fully outlined below.

In some embodiments, screens are designed to first find candidate agents that can bind to MF proteins, and then these agents may be used in assays that evaluate the ability of the candidate agent to modulate the MFP activity and the SCC phenotype. As will be appreciated by those in the art, there are a number of different assays which may be run; binding assays and activity assays.

In some embodiments, binding assays are done. In general, purified or isolated MFPs are used. The methods comprise combining a MFP and a candidate bioactive agent, and determining the binding of the candidate agent to the MFP. Generally, the MFP or the candidate agent is non-diffusably bound to a solid support having isolated sample receiving areas (e.g. a microtiter plate, an array, etc.). Microtiter plates and arrays are especially convenient because a large number of assays can be carried out simultaneously, using small amounts of reagents and samples. The particular manner of binding of the composition is not crucial so long as it is compatible with the reagents, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In some embodiments, the MFP is bound to the support, and a candidate bioactive agent is added to the assay. Alternatively, the candidate agent is bound to the support and the MFP is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the MFP may be done in a number of ways. In a preferred embodiment, the candidate bioactive agent is labeled, and binding determined directly. For example, this may be done by attaching all or a portion of the MFP to a solid support, adding a labeled candidate agent (for example a fluorescent label), washing off excess reagent, and determining whether the label is present on the solid support. Various blocking and washing steps may be utilized as is known in the art.

In some embodiments, only one of the components is labeled. For example, the proteins (or proteinaceous candidate agents) may be labeled at tyrosine positions using $^{125}I$, or with fluorophores. Alternatively, more than one component may be labeled with different labels; using $^{125}I$ for the proteins, for example, and a fluorophor for the candidate agents.

In some embodiments, the binding of the candidate bioactive agent is determined through the use of competitive binding assays. In this embodiment, the competitor is a binding moiety known to bind to the MFP, such as an antibody, peptide, binding partner, ligand, etc. Under certain circumstances, there may be competitive binding as between the bioactive agent and the binding moiety, with the binding moiety displacing the bioactive agent.

In some embodiments, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40.degree. C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In some embodiments, the competitor is added first, followed by the candidate bioactive agent. Displacement of the competitor is an indication that the candidate bioactive agent is binding to the MFP and thus is capable of binding to, and potentially modulating, the activity of the MFP. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In other embodiments, the candidate bioactive agent is added first, with incubation and washing, followed by the competitor. The absence of binding by the competitor may indicate that the bioactive agent is bound to the MFP with a higher affinity. Thus, if the candidate bioactive agent is labeled, the presence of the label on the support, coupled with a lack of competitor binding, may indicate that the candidate agent is capable of binding to the MFP.

In some embodiments, the methods comprise differential screening to identity bioactive agents that are capable of modulating the activity of the MFPs. In this embodiment, the methods comprise combining a MFP and a competitor in a first sample. A second sample comprises a candidate bioactive agent, a MFP and a competitor. The binding of the competitor is determined for both samples, and a change, or difference in binding between the two samples indicates the presence of an agent capable of binding to the MFP and potentially modulating its activity. That is, if the binding of the competitor is different in the second sample relative to the first sample, the agent is capable of binding to the MFP.

In some embodiments, methods for screening for bioactive agents capable of modulating the activity of a MFP in a cell are provided. The methods comprise adding a candidate bioactive agent, as defined above, to a cell comprising MFPs. Typically, laminin-5 negative primary human keratinocytes are used. The cells can also contain recombinant nucleic acids that encode MF sequences, Ras and a stable NF-κB repressor mutant of IκBα (i.e. IKB) (see Dajee et al., 2003, Nature, 421: 630-643). Methods for culturing cells and for assaying cell scattering, adhesion and migration are described in Russell et al., 2003, J. Cell Sci., 116: 3543-3556, the entire contents of which are incorporated herein by reference.

In some embodiments, candidate agents can be introduced into immunodeficient mice that can subsequently be challenged with a MFPs and monitored for the development of tumors. For example, intraperitoneal injections of antibodies against one or more MFPS can be given to mice bearing human foreskin xenografts (see Examples; and Li et al., 2003, EMBO J., 22: 2400-2410). The mice can then be challenged with Ras/IKB transformed human keratinocytes and monitored for tumor growth and histology as described in Dajee et al., 2003, Nature, 421: 630-643.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In one aspect, the assays are evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the determinations are determined at different stages of the cell cycle process.

Pharmaceutical Compositions

Bioactive agents having pharmacological activity are identified as described above. By "pharmacological activity" herein is meant that the compounds are able to enhance or interfere with the activity of MFPs. The compounds having the desired pharmacological activity may be administered in a physiologically acceptable carrier to a patient. A "patient" includes both humans and other animals, particularly mammals, and domestic animals. Thus, the methods are applicable to both human therapy and veterinary applications.

In some embodiments, bioactive agents are antibodies that recognize MFPs and that have been demonstrated to inhibit or modulate SCC as described herein. In other embodiments, bioactive agents include antisense compositions. These agents can be delivered directly or in pharmaceutical compositions along with suitable carriers or excipients, as well known in the art. Present methods of treatment include embodiments providing for administration of an effective amount of a compound or agent that inhibits the activity or expression of a MFP to a patient in need of treatment.

An effective amount of such agents can readily be determined by routine experimentation, as can the most effective and convenient route of administration and the most appropriate formulation. Various formulations and drug delivery systems are available in the art. (See, e.g., Remington's Pharmaceutical Sciences, supra.)

Suitable routes of administration may, for example, include oral, rectal, transmucosal, transdermal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot or sustained release formulation.

The pharmaceutical compositions may be manufactured by any of the methods well-known in the art, such as by conventional mixing, dissolving, granulating, dragee-making, levigating, emulsifying, encapsulating, entrapping, or lyophilizing processes. The compositions can include one or more physiologically acceptable carriers such as excipients and auxiliaries that facilitate processing of active molecules into preparations for pharmaceutical use. Proper formulation is dependent upon the route of administration chosen.

For example, for injection, the composition may be formulated in aqueous solutions, preferably in physiologically compatible buffers such as Hanks's solution, Ringer's solution, or physiological saline buffer. For transmucosal or nasal administration, penetrants appropriate to the barrier to be permeated are used in the formulation. Such penetrants are generally known in the art. For oral administration, the agents can be formulated readily by combining the active agents with pharmaceutically acceptable carriers well known in the art. Such carriers enable the agents of the invention to be formulated as tablets, pills, dragees, capsules, liquids, gels, syrups, slurries, suspensions and the like, for oral ingestion by a subject. The agents may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agent doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the agents can be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges for use in an inhaler or insufflator may be formulated. These typically contain a powder mix of the agent and a suitable powder base such as lactose or starch.

Compositions formulated for parenteral administration by injection, e.g., by bolus injection or continuous infusion can be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations for parenteral administration include aqueous solutions of the compound or agent to be administered, including in water-soluble form.

Suspensions of the active agents may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the agents to allow for the preparation of highly concentrated solutions. Alternatively, the active ingredient may be in powder form for constitution with a suitable vehicle, e.g., sterile pyrogen-free water, before use.

As mentioned above, the compositions can also be formulated as a depot preparation. Such long acting formulations may be administered by implantation (for example, subcutaneously or intramuscularly) or by intramuscular injection. Thus, for example, the present agents may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well-known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic agents and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g. polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the agents may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the agents for a few weeks up to over 100 days. Depending on the chemical nature and the biological stability of the therapeutic reagent, additional strategies for protein stabilization may be employed.

For any composition employed herein, a therapeutically effective dose can be estimated initially using a variety of techniques well-known in the art. For example, in a cell culture assay, a dose can be formulated in animal models to achieve a circulating concentration range that includes the $IC_{50}$ as determined in cell culture. Where inhibition of MFP activity is desired, the concentration of the test agent that achieves a half-maximal inhibition of MFP activity can be determined. Dosage ranges appropriate for human subjects can be determined, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

Dosage amount and interval may be adjusted individually to provide plasma levels or tissue levels of the active moiety which are sufficient to affect the expression or activity of MFPs, as desired, i.e. minimal effective concentration (MEC). The MEC will vary for each agent but can be estimated from, for example, in vitro data, such as the concentration necessary to achieve 50-90% inhibition of MFP activity using the assays described herein. Dosages necessary to achieve the MEC will depend on individual characteristics and route of administration. Agents or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a agent of the invention formulated in a compatible pharmaceutical carrier may also be prepared, placed in an appropriate container, and labeled for treatment of an indicated condition. Suitable conditions indicated on the label may include treatment of disorders or diseases, such as squamous cell carcinoma or other cancers and conditions associated with altered expression of MFPs.

EXAMPLES

Example 1

Requirement for G4 and/or G5 Domains in SCC Tumors

Laminin-5 undergoes processing of both its γ2 and α3 chains. As the α3 chain contains the primary integrin binding site(s), we performed further studies to examine the functional effects of α3 chain processing on SCC tumor development. We created truncations at the following sites: 1) amino acid residue 1337 (1337Tr), and 2) at amino acid residue 1450 (1450Tr). Keratinocytes from a junctional epidermolysis bullosa (JEB) patient with absent laminin □3 chain expression were transduced with LZRS retroviral vectors containing full length, 1450Tr or 1337Tr cDNA (Matsui et al., 1998, J. Exp. Med., 187: 1273-83). Each of the cDNAs restored trimeric laminin-5 expression in treated JEB keratinocytes, and each cDNA produced comparable levels of secreted laminin-5, as assessed by Western blot using laminin □3 specific antibody. While JEB keratinocytes with no laminin-5 expression (LacZ) were rounded, WT, 1337Tr and 1450Tr expressing keratinocytes showed flattening and spreading. While laminin-5 negative JEB keratinocytes (LacZ) were hypoproliferative, 1337Tr, and 1450Tr showed normal levels of proliferation, comparable to that of wild type (FIG. 5).

Because laminin-5 processing is closely tied to migration, we studied the 1337Tr mutant in more detail, as truncation at this position simulated the effects of processing in vivo. We found that 1337Tr cells were capable of migration, in fact, 1337Tr cells migrated more efficiently in scratch assays compared to cells expressing wild type α3 chain (FIG. 6).

We have previously described a model of human SCC which is obtained from SQ injection of Ras/IKB over expressing human keratinocytes in nude mice (Dajee et al., 2003, Nature, 421: 639-43). Tumors formed in these mice histologically and biochemically, were extremely similar to human SCC tumors. We showed that while laminin-5 negative keratinocytes showed no tendency to form tumors after Ras/IKB transformation, retroviral transfer of laminin-5 cDNA restored both expression of laminin-5 and restored the capacity of these cells to form tumors. These results are significant in that they demonstrate that laminin-5 expression is absolutely required for SCC development.

Figure 7:
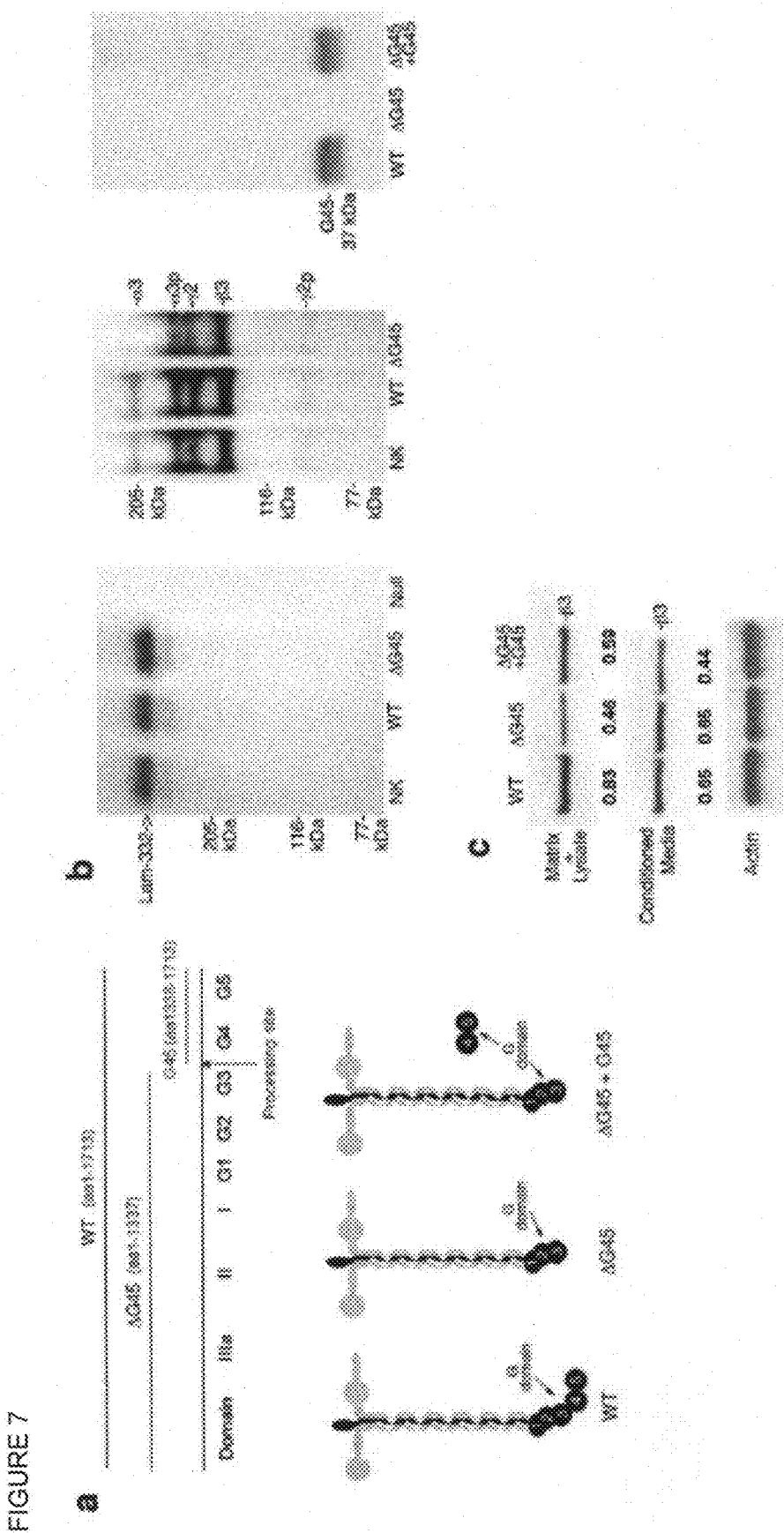
FIGS. 7A-7C. Laminin-332 G45 expression and function in human keratinocytes. (a) Schematic of the laminin α3 cDNA constructs used in this study. WT=wild type full length laminin α3 construct. ΔG45=laminin α3 chain truncated at amino acid 1337 (major processing site) (20). G45=portion of the laminin α3 chain G domain removed during processing. (b) Retroviral expression of laminin α3 cDNA constructs in JEB$^{null}$ keratinocytes Left panel, nonreduced immunoblot of conditioned keratinocyte medium using laminin-332 pAb, position of laminin-332 trimer and molecular weight markers (kD) shown to the left. NK=normal human keratinocytes. Center panel, reduced immunoblot of extracted keratinocyte matrix using laminin-332 pAb, positions of molecular weight markers (kD) are shown to the left and positions of individual laminin-332 chains are shown to the right. Right panel, nonreduced immunoblot analysis of conditioned keratinocyte medium using G45 pAb, position of G45 shown on left. (c) Quantification of cell layer (Matrix+Lysate) and conditioned media fractions from laminin α3 null keratinocytes expressing the indicated laminin α3 constructs by immunoblot using anti-laminin β3 antibody K140, or anti-actin antibody followed by densitometric analysis showed as integrated density of the ratio of laminin β3 to actin bands. Position of laminin β3 band shown on right.

As an extension of these tumor studies, we next studied the capacity of truncated laminin α3 chain to support SCC development. We Ras/IKB transformed JEB keratinocytes expressing α3 wild type (WT), 1337Tr or LacZ and injected SQ into nude mice. Through two sets of experiments with eight mice per condition, we found that the 1337Tr α3 chain expressing cells did not form any tumors and were most similar to LacZ negative controls (FIG. 7). In addition, 1450Tr cells, though one set of experiments and four mice total per condition, fail to produce SCC tumors either. Despite a lack of tumor formation, 1337Tr and 1450Tr cells at injection sites clearly showed expression and extracellular deposition of mutant laminin-5 molecules. These results are significant in that they demonstrate that the G4-5 domain of laminin-5 is essential for SCC development.

Example 2

Cloning of G4 and/or G5 MF Sequences

The laminin α3 chain is processed at residues 1337-1338, according to N-terminal sequencing studies (Tsubota et al., 2000, Biochem. Biophys. Res. Commun., 278: 614-620). As shown in preliminary results, we have produced a human laminin a 3 cDNA (1337Tr) which codes for a protein truncated at amino acid 1337, simulating the cleavage product, and have also produced 1450Tr, an α3 cDNA truncated at amino acid 1450. We propose to produce another laminin α3 cDNA (1551Tr), truncated near the beginning of the G5 domain at amino acid 1551. PCR primers will be designed to produce a product that spans from nucleotide 2771 to nucleotide 4653 of the full length wild type laminin α3 cDNA. This will include a unique BstII site on the laminin α3 cDNA, which will be on the 5' end of the PCR product, and a NotI site will be engineered into the 3' side of the PCR product. The full length laminin α3 cDNA in pENTR1A.COPYRGT. (Invitrogen) Gateway plasmid will be cleaved with BstII and NotI enzymes and the PCR product described above will be ligated into the vector with the 3' end ligating with the BstII site in the laminin α3 cDNA, and the 3' end ligating with the pENTR1A multiple cloning site. This cloning product, which will be confirmed by'sequencing, will comprise cDNA coding for the laminin α3 chain amino acids 1-1551. The laminin α3 1551Tr cDNA will then be transferred from the pENTR1A plasmid to a Gateway adapted LSRZ retroviral vector through lambda phage recombination reactions.

Three cDNA constructs coding for laminin α3 G domain will be produced. One termed G4 will code for amino acids 1338 to 1560, one termed G5 will code for amino acids 1560 to 1713, and a third termed G4-5 will code for amino acids 1338 to 1713. We will produce each by PCR of the wild type laminin α3 cDNA. In one PCR experiment, we will engineer an EcoR1 tail at either end of each of the three PCR products for cloning into the bacterial expression vector pGEX (Amersham). These constructs will be confirmed by sequencing, and then utilized to produce purified G4, G5 and G4-5 domains in a bacterial expression system.

In another PCR experiment, an NheI tail is inserted on the 5' side and a Not I tail on the 3' side of each of the G4. G5 and G4/5 PCR products. These are cloned into the mammalian expression vector pCEP which contains a BM40 signal sequence to which cDNA can be cloned to via an NheI restriction site. We have previously used the BM40 signal sequence in this vector to successfully promote secretion of collagen XVII ectodomain (Areida et al., 2001, J. Biol. Chem., 276: 1594-601). The G4, G5 and G4-5 are cloned into pCEP vector, to pick up the BM40 signal sequence, then the BM40 signal sequence and laminin α3 G domain cDNA will be removed from the vector by KpnI and NotI restriction sites and ligated into the pENTR1A Gateway vector, and by lambda phage recombination, the laminin α3 G domain cDNAs with their BM40 signal sequences will be cloned into a Gateway adapted LZRS retroviral plasmid.

Example 3

Assays for Detecting Inhibition of SCC Tumorigenesis

It is tested whether G4-5 domain performs its function in SCC before or after it becomes processed and dissociated from laminin-5 by to restoring tumor generating capabilities in Ras/IKB transformed 1337Tr keratinocytes by adding exogenous G4-5 protein or G4-5 cDNA. If Ras/IKB transformed 1337Tr keratinocytes form tumors in nude mice after receiving G4-5 protein or cDNA, it is indicated that the G4-5 domain is active in SCC tumors in a soluble form.

Matrigel, which contains heparin sulfate proteoglycan as one of its primary constituents, is the material in which we suspend our Ras/IKB tumors cells in, during subcutaneous injection into nude mice. As the laminin α3 G4-5 domain has heparin binding properties (Amano et al., 2000, J. Biol. Chem., 275: 22728-35), we will suspend the G4-5 domain at 100 μg/250 μl into Matrigel and use it as a substrate for injection of Ras/IKB transformed 1337Tr keratinocytes. Laminin α3 G4-5 domain suspended in Matrigel is used as a control. We hypothesize that laminin G4-5 domain will remain localized to the Matrigel impregnated matrix surrounding tumor cells and will be slowly released as matrix is gradually remodeled by tumor cells. Four mice injected with Ras/IKB treated 1337 cells embedded in G4-5 domain containing Matrigel are tested, using four serial biopsies at 1 week intervals by IDIF using G4-5 domain specific antibodies to assess the persistence of G4-5 domain protein in injection/tumor sites.

A second set of experiments is performed injecting Ras/IKB transformed cells embedded in Matrigel containing either laminin α3 or laminin α3 G4-5 domain. These cells are injected into nude mice and assessed over the course of 4 weeks for tumor development. Wild type Ras/IKB transformed keratinocytes are used as a positive control and 6 mice per condition will be used.

Alternatively, the laminin G4 domain cDNA is delivered by gene therapy as described below. This technique should promote long term G4-5 domain expression in 1337 Tr cells over the course of the 4 week assay.

Laminin G4-5 domain cDNA is cloned into LZRS retroviral vector. LacZ or laminin G4-5 cDNA containing retrovirus are used to infect 1337Tr keratinocytes. Cells are selected with Blasticidin, transformed with Ras/IKB and then injected into nude mice. Six mice per condition are assessed over 4 weeks for tumor growth as previously described (Dajee et al, 2003, Nature, 421: 639). Tumors are analyzed by IDIF using G4/5 or LacZ antibodies to verify secretion of retroviral cDNA products.

The effects of laminin α3 G4 and laminin α3 G5 antibodies on tumor development. Sufficient antibody is injected to maintain a circulating titer of 1:1000 as tested by dilution of mouse sera by Western blot analysis of G4-5 domain protein. Laminin α3 G4, G5 and G4-5 domains cloned into pGEX vector as outlined above is utilized to produce G4, G5 and G4-5 domain bacterial fusion proteins. Proteins are affinity purified on a GST column, and GST tags are subsequently removed by enterokinase (Invitrogen). Isolated G4 and G5 domain proteins are used to produce rabbit polyclonal antisera at Josman Labs, Napa, Calif., according to their recommended protocols.

Once high titer polyclonal antisera is obtained, additional G4, G5 and G4-5 protein are produced, affinity purified and coupled to a Sepharose CL-4B column at a concentration of 0.5 mg protein per ml of gel. G4 polyclonal antisera is affinity purified on a G4-sepharose column and G5 antisera is affinity purified on a G5 sepharose column. Affinity purified G4, G5 and G4-5 antibodies are dialyzed into PBS and filter sterilized. Initially, we the antibodies (G4, G5, G4-5) are tested by IP injection of immunodeficient mice bearing human foreskin xenografts by a technique utilized previously (Li et al., 2003, EMBO J., 22:2400-2410). Titers of circulating antibodies in treated mice are assessed at 3 day intervals using sera obtained from tail vein bleeds. The amount of antibody injected and the injection intervals is adjusted to maintain a titer sufficient to detect laminin G4-5 protein by Western blot at a 1:1000 serum dilution. We will clinically assess foreskin grafts and mouse skin over the course of three weeks of injections to determine whether epidermal separation is noted, and mice will be examined by autopsy to detect any epithelial sloughing of mucosa or internal organs.

Once the proper antibody dose and injection intervals are obtained, antibody inhibition of Ras/IKB wild type keratinocyte derived tumors is performed. In these studies, nude mice are administered periodic G4, G5 or G4-5 antibody injections to maintain a constant circulating antibody titer as described above. Once antibody titers are initiated, then mice receive SC injections of Ras/IKB transformed human keratinocytes. Three groups of 6 mice each are studied, using affinity purified laminin α3 G4 antibody, laminin α3 G5 antibody or mouse IgG. G domain antibody conditions are analyzed for tumor growth and tumor histology as previously described (Dajee et al., 2003; Nature, 421:639-43).

Example 4

Targeting a Tumor Specific Laminin Domain

Laminin-332 is critical for squamous cell carcinoma (SCC) tumorigenesis, but targeting it for cancer therapy was unachievable due to laminin-332's key role in promoting tissue integrity. Here, we show that a portion of laminin-332 termed G45, which is proteolytically removed and absent in normal tissues, is prominently expressed in most human SCC tumors and plays an important role in human SCC tumorigenesis. Primary human keratinocytes lacking G45 (ΔG45) showed alterations of basal receptor organization impaired matrix deposition, and increased migration. After SCC transformation, the absence of G45 domain in ΔG45 cells was associated with deficient ERK and phosphotidylinositol 3-kinase (PI3-K) pathway activation, impaired invasion, deficient metalloproteinase activity and absent tumorgenicity in vivo. Expression of G45 or activated PI3-K subunit in ΔG45 cells reversed these abnormalities. G45 antibody treatment induced SCC tumor apoptosis, decreased SCC tumor proliferation and markedly impaired human SCC tumorigenesis in vivo without affecting normal tissue adhesion. These results demonstrate a remarkable selectivity of expression and function for laminin-332 G45 in human SCC tumorigenesis and demonstrate its use as a specific target for anti-cancer therapy.

Squamous cell carcinoma (SCC) is a prevalent, invasive neoplasm arising in many tissues; causing significant morbidity and mortality. SCC is the most common cancer capable of metastasis and is second in frequency only to basal cell carcinoma. The incidence of SCC appears to be rising, and is more frequently affecting younger individuals. SCC tumors can show a high risk of recurrence, and those derived from mucosal sites often invade neighboring tissues and can also metastasize to the lymph nodes, lung and other distant sites. Chemotherapy for SCC has not been shown to significantly affect long term survival and most patients with advanced disease die despite currently available therapies. Results from the use of epidermal growth factor receptor inhibitory agents in clinical trials of advanced head and neck SCC in combination with conventional chemotherapy have been only modestly encouraging. All of these factors have led to the search for new and more specific agents in the treatment of SCC.

Laminins are a family of trimeric extracellular glycoproteins associated with the basement membrane zone (BMZ). Laminins interact with cell surface receptors and other BMZ components to provide cells with an interface to communicate with their surrounding extracellular environment. Laminin-332, a large molecule consisting of α3, β3, and γ2 chains, shows widespread expression in many epithelial tissues as well as in the tumor microenvironment of many carcinomas. Laminin-332 is required for tumorigenesis in a well characterized in vivo model of human SCC. In addition, laminin-332 expression in SCC tumors arising from a number of tissues correlates both with tumor invasiveness and patient prognosis. Soluble and insoluble laminin-332, furthermore, have been observed to induce the phosphoinositol-3-kinase (PI3-K) and mitogen-activated protein kinase (MAPK) pathways, which are known to mediate carcinogenesis.

Due to its critical role in SCC tumorigenesis, laminin-332 would represent an excellent candidate as an anti-tumor target, were it not for laminin-332's equally critical role in maintaining epithelial-mesenchymal cohesion across a broad range of normal tissues. For example, in the inherited disorder Herlitz's junctional epidermolysis bullosa (JEB), absence of laminin-332 expression due to laminin-332 gene mutations leads to widespread blistering and erosions and usually death during infancy. Therefore, any anti-cancer strategy targeting laminin-332 would need to address how to selectively disrupt laminin-332's pro-tumorigenic function without affecting its pro-cohesive function in normal tissues.

Towards this end, we focused on the α3 chain of laminin-332, which undergoes proteolytic cleavage shortly after secretion. This proteolytic event, which takes place in the large C-terminal globular (G) domain near the junction of the third and fourth EGF-like repeats termed G3 and G4 (FIG.

6a), converts the laminin α3 chain from a 200 kDa precursor to a 165 kDa processed product. The 37 kDa precursor region of the laminin α3 chain containing two EGF-like repeats G4 and G5 (G45), is removed during processing and as a result, is absent in normal mature tissues. Any postnatal expression of unprocessed laminin α3 chain/G45 is only detectable transiently at healing wound edges.

There are many parallels between the process of wound healing, and tumorigenesis, including active synthesis of BMZ components, proliferation and cell migration. Because of these parallels, and because of the absence of unprocessed laminin α3 in normal mature tissues, we focused on the role of the laminin α3 G45 in human SCC. In this study, we demonstrate that while G45 is undetectable in normal mature tissues, it shows widespread expression in human SCC tumors, where it plays an important role in SCC tumorigenesis. Further we show that laminin α3 G45 can be selectively targeted in vivo by antibodies to inhibit human SCC tumorigenesis without disrupting normal tissues.

Materials And Methods

Cell lines. Primary human keratinocytes isolated from normal skin and a patient with junctional dystrophic epidermolysis bullosa lacking laminin-332 expression due to LAMA3 mutations were cultured in a 1:1 mix of defined keratinocyte serum free medium (SFM; Gibco, Carlsbad, Calif.) and Medium 154 (Cascade Biologics) at 37° C. in a humidified 5% $CO_2$ incubator. Modified human 293 PHOENIX cells (gift from Dr. G. Nolan, Stanford, Calif.) were cultured in DMEM supplemented with 10% fetal calf serum, 100 IU/ml penicillin and 100 µg/ml streptomycin at 37° C. in a humidified 10% $CO_2$ incubator.

Complementary DNA constructs. Human laminin α3 chain (GenBank NM227.2) is physiologically processed at residues 1337-1338, according to N-terminal sequencing studies. As there are no known mutations in laminin 332 alpha3 G45 domain in JEB patients, three cDNAs encoding HuLAMA3 were produced, one comprising the 200 kDa full-length α3 wild-type chain (WT), coding for residues 1-1713. The second comprised the 165 kDa α3 chain truncated at the physiologic processing site comprising residues 1-1337 (ΔG45), and the third comprised the 37 kDa cleaved G45 (G45), residues 1338-1713. These were generated by PCR, verified by direct sequence analysis and cloned into the retroviral vector backbone LZRS containing the encephalomyocarditis virus (EMCV)-IRES and blasticidin-resistance sequences and a GATEWAY® (Invitrogen, Carlsbad, Calif.) destination site, (pLZRS-GATEWAY). The BM40 signal sequence was incorporated upstream and in-frame of the mutant HuLAMA3 for directing expression. Retroviral expression vectors encoding either activated Ha-Ras, IκBα, or activated PI3-K p110-CAAX have been previously characterized. Amphotropic retroviral supernatant production and retroviral keratinocyte transduction were performed as described.

Statistical analysis. Student's t-test was employed to ascertain significant difference between data sets using Microsoft Excel. P-values are listed in figure legends.

WT and ΔG45 c DNA forward primer: 5'-AAAAAAGCTAGCATGG GTTGGCTTATA-3' (SEQ ID NO:25) α3WT cDNA reverse primer: 5'-CCCCCCGGGC-CCGCGGCCGCTTACAGGTCCTC-CTCGCTAATCAATTTTT GCTCCTGGTCAGGACAAC-CATTCAGACTGAC-3' (SEQ ID NO:26) ΔG45 reverse primer 5'-AAAAAACCAGGTTTAACAAGACCAA-GACTTTTCGTAT CAACCTGCTGTTGCTGGCCACAC-CAGTGGCCTCCCCTAGGAGC-3' (SEQ ID NO:27) G45 forward primer: 5'-TTATGCTAGCGGACACACCAGT-3' (SEQ ID NO:28) G45 reverse primer: 5'-TATTCTCGAGT-TACTGGTCAGGAC-3' (SEQ ID NO:29).

Antibodies. Anti-laminin α3 chain mouse mAb BM165 and G45 rabbit pAb, anti-laminin-332 rabbit pAb and laminin β3 chain mouse mAb K140 were previously characterized. We commercially obtained anti-p-ERK and p-Akt (Ser473) (Cell Signaling), anti α6 integrin mAb G0H3 (Chemicon), Ki67 mAb (LabVision) paxillin mAb (BD Biosciences Pharmingen) phalloidin pAb (Invitrogen) and β-actin mAb (Sigma).

Protein analysis. Laminin-332 deposition among WT, ΔG45, and ΔG45+G45 cells were studied over a 24 hr period. Proteins from whole cell lysates, conditioned media and matrix deposition were extracted and quantified by immunoblot as previously described. K140, n anti-laminin β3 mAb, was used for laminin deposition comparisons, which controlled for cell density by normalizing laminin β3 to actin bands. For measurement of AKT phosphorylation, near-confluent cells were extracted in RIPA buffer with protease and phosphatase inhibitors. Ratio of phospho-AKT to total AKT was calculated through densitometry. For ERK phosphorylation, Ras-IκBα (or Ras-IκBα+PI3-K) transformed cells were growth factor starved for 24 h then stimulated with 10 ng/ml EGF for 2 min before lysis in RIPA buffer for immunoblot analysis. Densitometric analysis was shown as phosphorylated with ERK1/2 normalized to untreated WT controls. NIH ImageJ software was used for densitometric analysis.

Immunofluorescence microscopy. Confocal analysis of cell adhesion proteins was performed exactly as previously described. Assaying ERK activation of keratinocytes after pulsing with 10 ng/mL EGF for two minutes has been described previously. Briefly, representative images from $JEB^{null}$ keratinocytes expressing the indicated laminin α3 constructs were visualized by immunofluorescence microscopy using phospho-ERK antibody. Nuclear localization of phospho-ERK was quantified as % phospho-ERK staining nuclei over total nuclei. Imaging was carried out with a Zeiss LSM 510 confocal laser scanning microscope.

Immunohistochemistry. For immunoperoxidase staining, 5 µm paraffin sections of SCC tissue microarrays from skin (SK802) and multiple organs (BC00019) obtained from US Biomax Inc, Rockville, Md., were deparaffinized, rehydrated and antigen unmasked by boiling in 50 mM Tris-HCl, pH 9.5 for 15 min. Sections were then incubated with G45 rabbit pAb followed by biotin-conjugated secondary and DAB detection (LabVision). Tissues were counterstained with hematoxylin. G45 staining was graded by 2 independent blinded observers according to the percentage of number of tumor cells positive with staining; >75% (Strong), 25%-75% (Moderate) and <25% (Negative). For immunofluorescence, 5 µm cryosections were incubated with antibodies listed above and Hoescht-counterstained. Images were taken using a Zeiss Axiovert-100 microscope.

Cell adhesion, migration and invasion assays. G45 adhesion studies were carried out by coating purified LG4/5 fragment (10 µg/ml overnight at 4° C. Ras/IκBα transformed normal primary human keratinocytes were detached in PBS containing 10 mM EDTA and rinsed in serum-free medium. After washing with PBS and saturation of the wells with 1% BSA, the cell adhesion assays were performed in serum-free medium, as described in Shaw et al. (1997) Cell 91:949-60. Adhesion was determined after fixation with 1% glutaraldehyde in PBS and staining with 0.1% crystal violet, by absorbance at 570 nm using a MR5000 ELISA reader. A blank value corresponding to BSA-coated wells was subtracted. Adhesion inhibition with G4/5 antibody (20 µg/ml) or heparin (10 µg/ml, Sigma), took place 60 minutes prior to as well as during the cell adhesion experiment. Cell detachment assays were carried out as described (Utani et al. (2003) J Biol Chem278:34483-90). Briefly, $2 \times 10^4$ cells/cm$^2$ were incubated for 24 h at 50% confluence. Detached cells were quantified at increasing time intervals after incubation in a 1:70 dilution of trypsin/EDTA in PBS (BioWhittaker). Each adhesion/detachment experiment was performed in triplicate.

Cell monolayer scratch assays=were performed by plating $10^6$ cells into 60 mm tissue culture plates and incubating cells in SFM for 24 hr. Media was changed to SFM without additives for 16 hr. Fresh mitomycin-C (Sigma) was added at 10 µg/ml and cells incubated 3 hr. on ice. Cells were washed twice with SFMANA and scratched with a 1 mm cell scraper. Plates were washed three times with SFMINA and marked areas photographed using a Zeiss Axiovert 25 microscope (50× magnification). Migration was quantified by calculating percent change in the area between migrating cell sheets using NIH image software and >3 repeats per data point.

The in vitro invasion assays) were performed as previously described, briefly assays were performed in triplicate using chambers containing a polycarbonate membrane with eight micron pores, coated with Matrigel (Becton Dickinson). After 24 hours, invasive cells in the bottom chamber were lysed and quantified using CyQuant GR dye. Invasion index was quantified relative to percent invasion by JEB$^{null}$ keratinocytes.

Zymography. 1 million keratinocytes were starved for 24 h and incubated in SFM media. Conditioned media were recovered and concentrated 80×. Samples were dissolved in non-reducing sample buffer (6% glycerol, 1% SDS, and 0.004% bromophenol blue), incubated in 37° C. water bath for 10 min, and loaded on a 10% gelatin gel for detection of MMP2 and MMP9 and 12% casein gel for detection of MMP1 (Invitrogen). The gel was run in Tris/glycine buffer for 2 h and then incubated in 2.5% Triton X-100 solution for 15 min twice to remove SDS. To detect MMP activity, the gel was incubated in reaction buffer containing 50 M Tris-HCl (pH 7.4), 0.2 M NaCl, 5 mM CaCl$_2$, and 1 µM ZnCl$_2$ overnight at 37° C. Protease activity was detected as translucent area in a Coomassie blue-stained gel. The scanned results of gels were calculated using NIH ImageJ software.

Tumorigenicity assay. Tumorigenicity assay was performed as previously described. Briefly, keratinocytes were incubated with LZRS-IRES-Blasticidin/H-Ras or LZRS-IRES-Blasticidin/IκBαM retroviral titer. Gene transfer was verified by immunoblotting of cell lysates.

One million Ras/IκBαM transformed cells suspended in 200 µl Matrigel (Beckton-Dickenson), were injected subcutaneously to the dorsal flank of 6 week nude mice, 5 mice were used per each condition. Tumors were measured on a weekly basis and analyzed at the end of four weeks. All animal studies were conducted in accordance with protocols approved by the Stanford Animal Use Committee. In some experiments, affinity purified G45 pAb, affinity purified mAb K140, or control rabbit IgG (Sigma) were injected intraperitoneally on a weekly basis, at a dose of 500 µg per mouse per week, which has been previously demonstrated to maintain high circulating antibody levels. Apoptotic tumor cells were detected using Roche's In Situ Cell Detection Kit. Proliferating SCC cells were detected with Ki67 and DAPI immunofluorescent staining. Proliferation and apoptosis were quantified as the ratio of staining of nuclear Ki67 and TUNEL, respectively, to total nuclear staining. NIH Image software was used to quantify the subset of apoptotic or proliferating tumor cells in five representative low-power fields on each tumor.

Results

Widespread accumulation of laminin-332 G45 in human SCC tumors. In an effort to determine whether unprocessed laminin α3 G45 domain accumulated in human SCC tumors, we examined frozen sections of four normal skin and four cutaneous SCC specimens obtained by Moh's surgery, using immunofluorescence microscopy. Using an antibody specific to the G45 domain and an antibody (BM165) which recognized the processed laminin-332 trimer (FIG. 6a), we found that G45, while consistently undetectable in normal skin, was abundantly present, and showed colocalization with mAb BM165 in human cutaneous SCC tumors from each of the four patient samples tested (FIG. 6b). In a more extensive survey of 75 cutaneous (FIG. 1c) and 56 extracutaneous (FIG. 6d) paraffin embedded SCC tumors, over 75% showed moderate to strong G45 expression. All G45 positive tumors also stained positively with total laminin-332 pAb. All but one of the G45 negative tumors were also negative for total laminin-332 expression. Thus G45 domain accumulation correlated well with total laminin-332 expression in SCC tumors.

Laminin-332 G45 domain facilitates the organization and function of matrix receptor complexes. To investigate laminin-332 G45 in SCC, we produced three laminin-332 α3 chain constructs (FIG. 7a), a full length wild type chain (WT), a mutant lacking G45 (ΔG45) and G45 (G45) itself. These constructs were stably expressed in laminin-332 null keratinocytes derived from a patient with junctional epidermolysis bullosa (JEB$^{null}$) with underlying LAMA3 gene mutations. As will be shown below, G45 separately expressed from the rest of the laminin332 molecule (ΔG45+G45) performed many of the same functions, albeit less efficiently (detailed below), as G45 synthesized as part of the laminin-332 molecule (WT). JEB$^{null}$ keratinocytes expressing G45 without the ΔG45 construct, like untransduced JEB$^{null}$ keratinocytes, did not adhere to culture surfaces and were not further analyzed further in vitro.

ΔG45 JEB$^{null}$ cells synthesized, assembled and secreted trimeric laminin-332 as shown by non-reduced immunoblot analysis (FIG. 7b, left panel) and the ΔG45 chain was of equivalent apparent molecular weight compared to processed WT α3 chain (α3p) as shown by reduced immunoblot (FIG. 7b, center panel). The G45 construct was expressed in ΔG45 cells at levels similar to WT cells as clearly seen in conditioned cell medium (FIG. 7b, right panel), as well as cell lysate. We compared laminin-332 in these cells isolated from culture medium, or extracted from culture matrix as previously described, using actin from cell lysates as a control. Normally keratinocytes deposit more laminin-332 into their matrix than they secrete into their media, but ΔG45 cells secreted more laminin-332 into medium than matrix (FIG. 7c), consistent with previous observations. G45 synthesis in ΔG45 cells led to the majority of laminin-332 being deposited into matrix, indicating that G45 promoted laminin-332 deposition.

Figure 8:
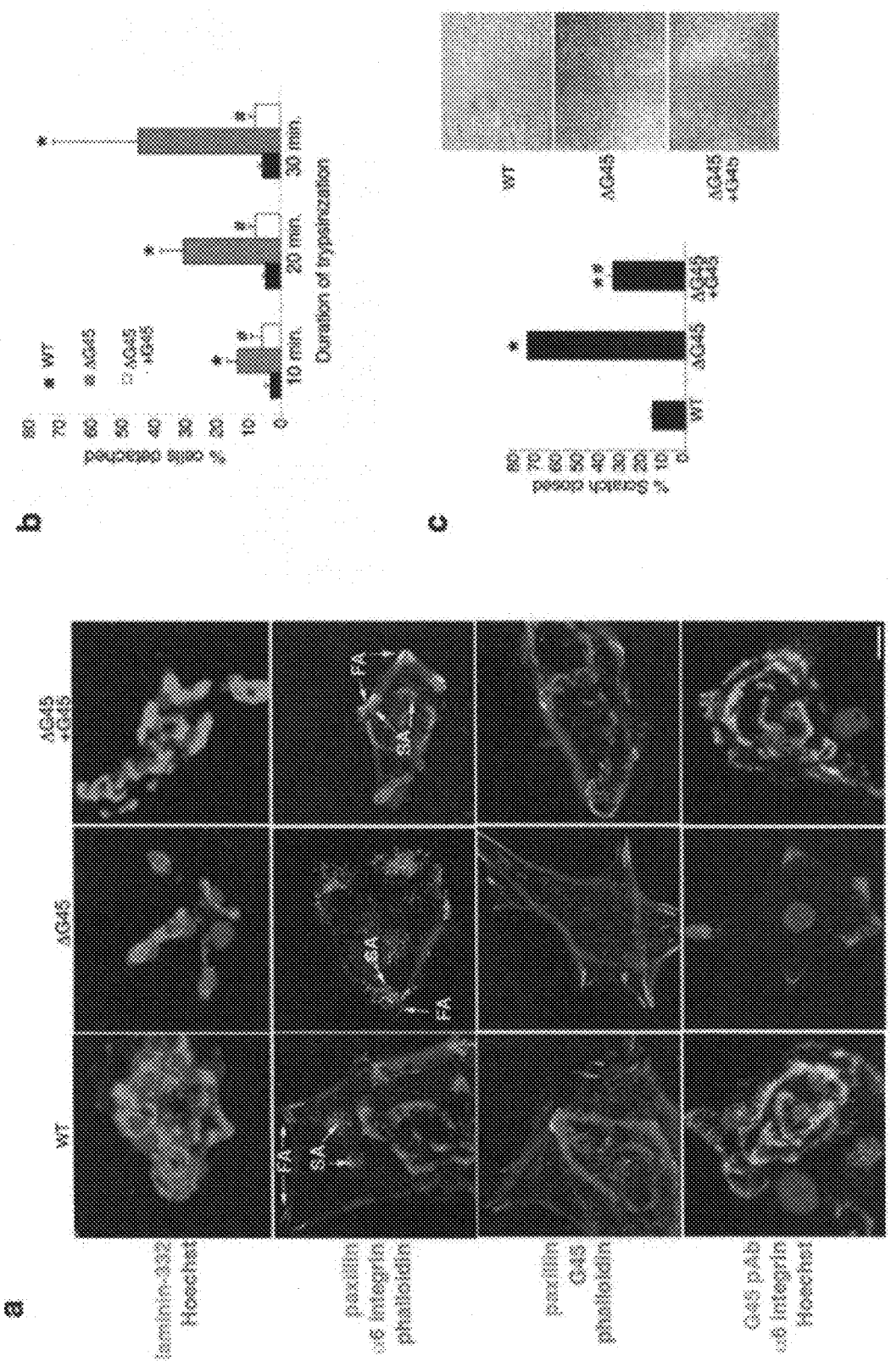
FIGS. 8A-8C. Laminin-332 G45 influences matrix receptor organization and function. (a) Effects of G45 on keratinocyte matrix deposition and adhesion complex formation. Keratinocytes expressing the indicated α3 chain constructs were analyzed by triple-label confocal microscopy. Color of secondary antibodies and staining are designated by the color of the text listing the primary antibody. FA, focal adhesion; SA, stable adhesion. Scale bar=10 μm. (b) G45 promotes resistance to trypsin dissociation. Established keratinocyte cultures expressing the indicated laminin α3 constructs were subjected to dilute trypsin at the indicated intervals and % of cells dissociated was quantified. Data represents the results of triplicate experiments, error bars=+/− SD, *=p-value<0.05 compared to WT cells, #=p-value<0.05 compared to ΔG45 cells (c) G45 modulates keratinocyte migration during in vitro wound healing assay. Confluent monolayers of keratinocytes expressing indicated laminin constructs were tested for their ability to migrate into 1 mm scratches over the course of 24 hours and % closure of scratch was quantified as shown. Data represents the results of triplicate experiments, error bars=+/− SD, *=p-value<0.05 compared to WT cells, #=p-value<0.01 compared to ΔG45 cells.

This was further examined by confocal microscopy (FIG. 8a). Analysis of laminin-332 antibody staining confirmed that the absence of G45 in ΔG45 cells correlated with a reduction in deposited laminin-332 which was again improved with the expression of G45 in ΔG45 cells (FIG. 8a top panel). Additional effects of G45 on basally located cell receptor complexes were also noted. WT cells showed characteristic peripheral focal adhesions (FA), containing paxillin and central stable adhesions (SA) containing α6β4 integrin (FIG. 8a second panel). However SAs in ΔG45 cells were abnormally peripheral, adjacent to FAs (FIG. 8a third panel). G45 expression in ΔG45 cells restored some SAs to their normal central location. G45 co-localized with α6β4 integrin in SAs in WT and ΔG45 cells (FIG. 8a, bottom panel), suggesting interaction of G45 with SAs. In accordance with the analysis of SA formation, ΔG45 cells showed increased sensitivity to trypsin-induced detachment (FIG. 8b), which was corrected with G45 expression, suggesting that G45 induced laminin-332 deposition and SA formation led to increased stable cell adhesion. Previous studies have shown an inverse relationship between the rate of keratinocyte migration and laminin-332 deposition. In accordance with this, ΔG45 keratinocytes, with decreased laminin-332 deposition, migrated faster into scratches placed in confluent monolayers than WT cells with normal laminin-332 deposition (FIG. 8c). Expression of G45 construct in ΔG45 cells partially reversed these effects. We next determined whether these adhesion and migration abnormalities and these changes in extracellular matrix deposition and organization correlated with changes in tumorigenic potential.

Figure 9:
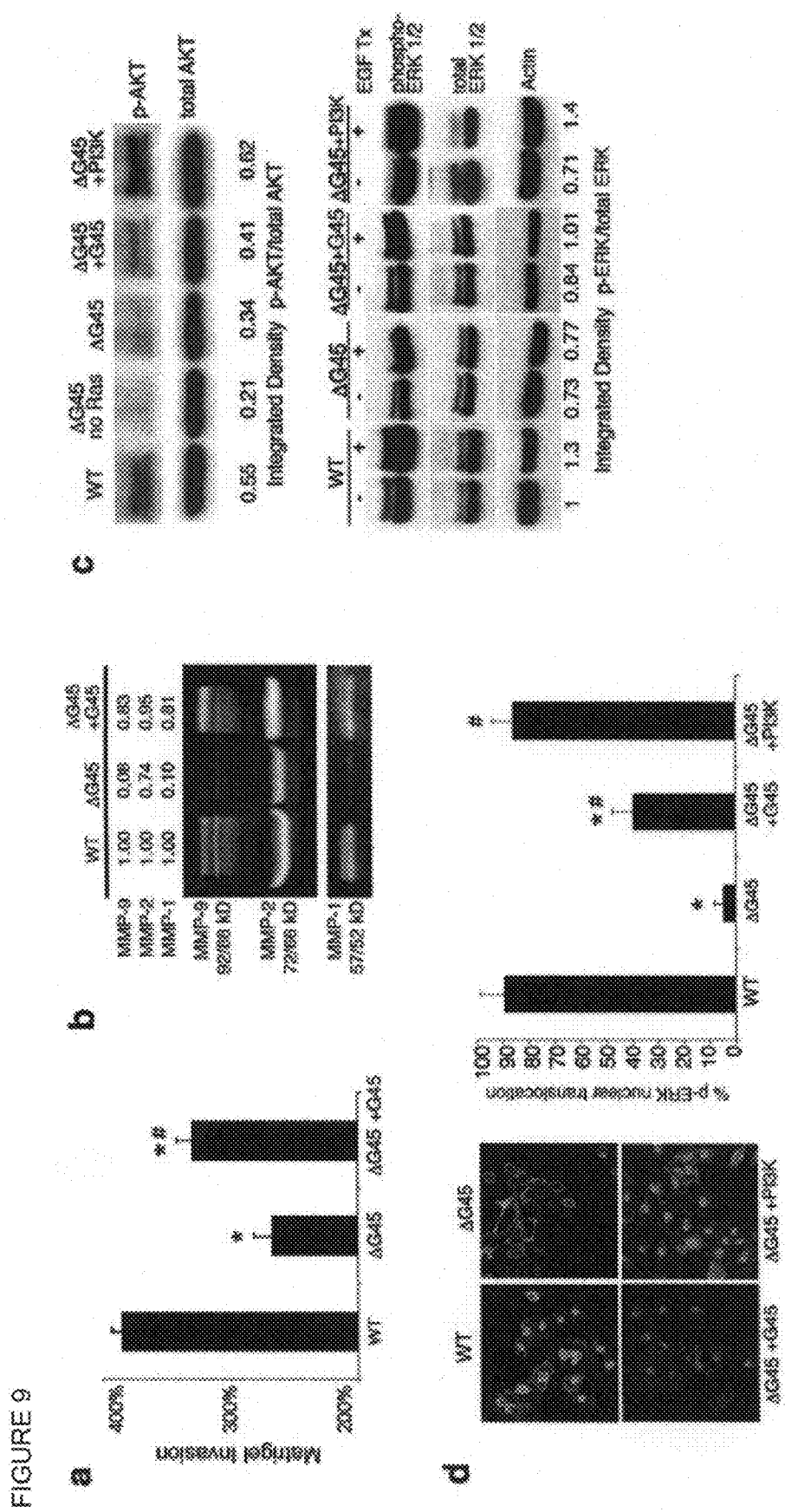
FIGS. 9A-9D. Laminin-332 G45 drives human SCC tumorigenesis and invasion by increasing activation of MMPs, ERK and PI3-K pathways, promoting proliferation and inhibiting apoptosis. Ras-IκBα transformed JEB$^{null}$ keratinocytes expressing the laminin constructs indicated in FIG. 2, (and in some instances activated p110 PI3-K subunit) were analyzed under the following conditions: (a) Keratinocytes expressing G45 showed increased cellular Matrigel invasion. Data represents triplicate independent experiments +/− SD and are quantified as a percentage of basal invasion by JEB$^{null}$ cells alone, *=p-value<0.05 compared to WT cells, #=p-value<0.05 compared to ΔG45 cells (b) G45 expression promotes MMP activity. Conditioned medium was analyzed by gel zymography, and intensity of digestion of bands by indicated metalloproteinases was quantified by densitometry as shown above the zymogram (c) G45 expression promotes PI3-K pathway and ERK activation. Top: cell lysates were analyzed by immunoblot using phospho-AKT (p-AKT) and total AKT antibodies. Ratio of phospho-AKT to total AKT staining was quantified using densitometry. All cell studied were Ras/IKBα transformed except where indicated (no Ras). Bottom: lysates from growth factor starved cells were analyzed by immunoblot before or after EGF treatment, using antibodies to phospho-ERK, total ERK and actin. Densitometric analysis is shown at the bottom as phosphorylated ERK1/2 normalized to untreated WT controls and total ERK1/2 expression. (d) G45 promotes phospho-ERK nuclear translocation. Left: Representative images from JEB$^{null}$ keratinocytes expressing, the indicated laminin α3 constructs were visualized by immunofluorescence microscopy using phospho-ERK antibody. Graph on right shows quantification of the effects of G45 on phospho-ERK nuclear translocation. Data represents triplicate independent experiments +/− SD and are quantified as a percentage of phopho-ERK staining nuclei over total nuclei, *=p-value<0.001 compared to WT cells, #=p-value<0.01 compared to ΔG45 cells.

Laminin-332 G45 promotes tumor invasion and metalloproteinase activity. SCC tumorigenesis was examined by retroviral transduction of primary human keratinocytes with oncogenic Ras and the NF-κB inhibitor IκBα, which produces transformed cells that generate human epidermal tumors indistinguishable from human SCC upon transfer to immunodeficient mice. Following Ras/IκBα transformation, ΔG45 cells showed impaired invasion into Matrigel, compared to WT cells which was partially corrected through G45 retroviral transduction (FIG. 9a). Carcinoma invasion has been linked to metalloproteinase activity and ΔG45 cells showed a striking deficiency of MMP-9 and MMP-1, which have been associated with SCC invasion (FIG. 9b). Metalloproteinase deficiencies in ΔG45 cells were reversed through expression of G45, although not to the levels of WT cells. This deficient MMP expression explains why, despite their increased migration in the untransformed state, transformed ΔG45 cells invaded Matrigel more poorly than transformed WT cells.

Activation of Phosphoinositol-3-kinase (PI3-K) and ERK pathways by laminin-332 G45. PI3-K pathway activation is critical for SCC invasion and ΔG45 cells showed decreased AKT phosphorylation suggesting that G45 was essential in promoting PI3-K pathway activation (FIG. 9c). G45 expressed as part of the laminin-332 molecule was more efficient at promoting AKT phosphorylation compared to G45 expressed separate from laminin-332 (≠G45+G45). We also found an impairment of ERK activation in transformed ΔG45 cells which was restored partially through overexpression of G45, but fully through overexpression of activated PI3-K p110 catalytic subunit (FIG. 9c). In addition, ΔG45 cells showed defective nuclear translocation of activated ERK, which was corrected partially through G45 expression but fully through activated p110 expression (FIG. 9d).

Figure 10:
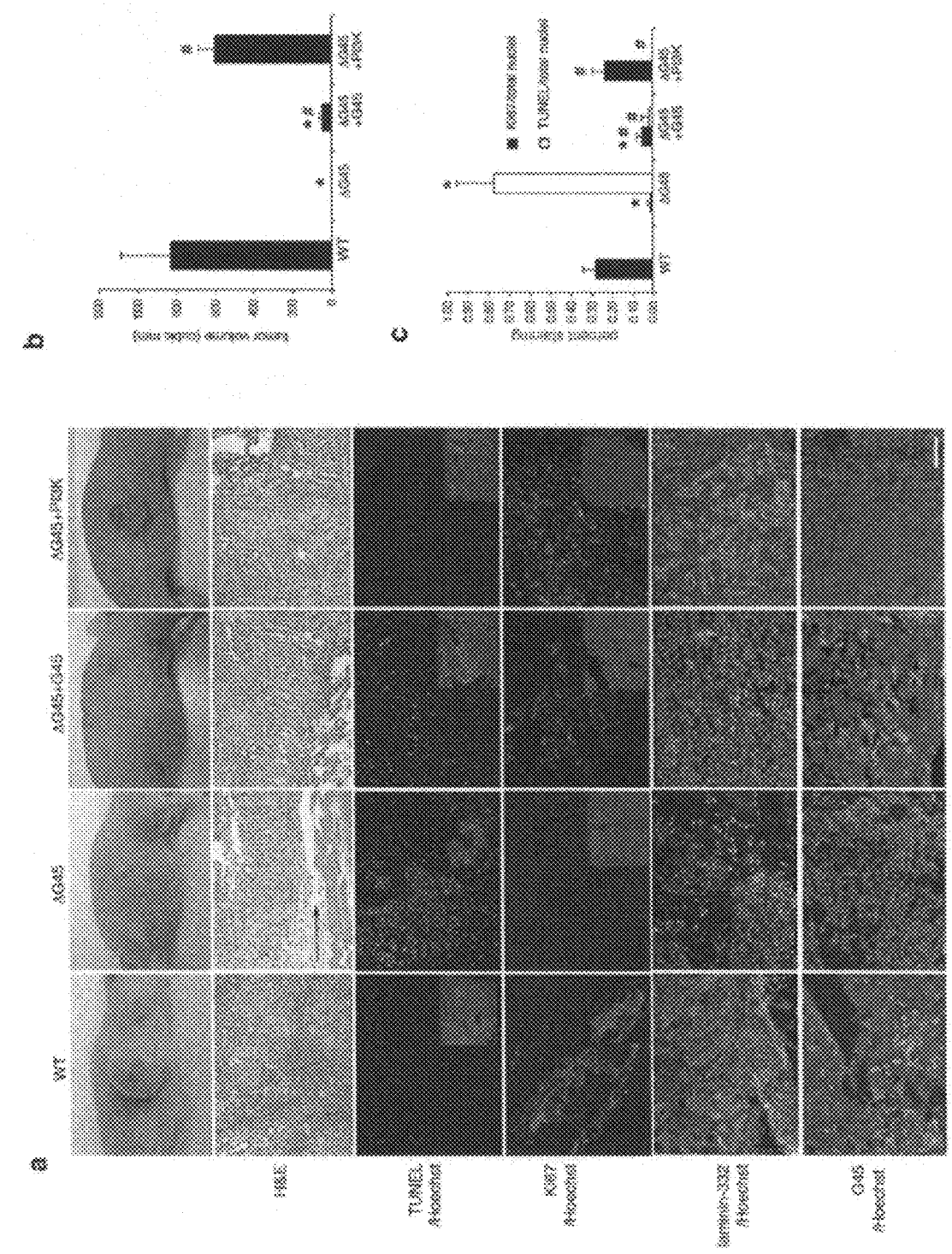
FIGS. 10A-10C. G45 promotes human SCC tumorigenesis in vivo. (a) Representative photos in the top panel show a lack of tumor growth in cells lacking G45 expression(ΔG45, top panel), but a partial restoration when G45 was separately expressed (ΔG45+G45), and a near-complete restoration of tumorigenesis when activated p110 (ΔG45+PI3K) Histologic invasion of underlying muscle (second panel) was absent in tumors lacking G45 expression (arrow). Apoptosis was greatly increased in tumors lacking G45 (third panel) as shown by TUNEL assay of frozen tumor sections, inset: Hoechst nuclear stain. Proliferation was greatly reduced in tumors lacking G45 (fourth panel) shown by Ki67 antibody analysis of frozen tumor sections, inset: Hoechst nuclear stain. Laminin-332 deposition (fifth panel) was greatly reduced in the absence of G45 subunit, but was partially rescued by expression of G45 and fully rescued by activated p110 (PI3-K) expression as shown by immunofluorescence microscopy of frozen tumor sections using laminin-332 polyclonal antibody. G45 construct produced levels of G45 expression in tumor sections equivalent to WT construct as assessed by immunofluorescence microscopy of frozen tumor sections using G45 pAb (bottom panel). Scale bar=100 µm. (b) G45 promotes human SCC tumorigenesis. Tumor growth was measured 4 weeks after subcutaneous transfer of indicated cells to immunodeficient mice. Error bars, +/− SD. *=p-value<0.05 compared to WT cells, #=p-value<0.05 compared to ΔG45 cells. (c) G45 promotes proliferation and protection from apoptosis. TUNEL assay and Ki67 staining as assessed by immunofluorescence microscopy of frozen tumor sections was quantified as a percentage of staining of total nuclei. Error bars, +/− SD. *=p-value<0.05 compared to WT cells, #=p-value<0.05 compared to ΔG45 cells.

Laminin-332 G45 is required for in vivo Ras driven SCC tumorigenesis. We next examined G45 in human SCC tumorigenesis in vivo. After transfer to immunodeficient mice, transformed ΔG45 cells showed strikingly impaired tumorigenesis (FIG. 10a, top row). This was slightly improved when G45 was expressed in ΔG45 cells and tumor growth was more fully restored in ΔG45 cells through activated p110 expression. Transformed JEB$^{null}$ cells overxpressing G45 alone produced no detectable tumors 4 weeks after injection, similar to what has been previously demonstrated for transformed JEB-$^{null}$ cells alone. While invasion into underlying muscle was consistently noted in tumors expressing wild type laminin α3 chain (WT), ΔG45 tumors showed a conspicuous invasive defect (FIG. 10a, second row). However, invasion into muscle was noted in ΔG45 cells tumors after expression of G45 or activated p110 subunit. Widespread apoptosis was present in ΔG45 tumors (FIG. 10a, third row, FIG. 10b). G45 expression diminished and p110 expression completely inhibited apoptosis in ΔG45 tumors. ΔG45 tumors showed deficient proliferation which was modestly increased with G45 domain expression, and fully restored to wild type levels with p110 expression (FIG. 10a, fourth row, FIG. 10c). Expression of G45 promoted laminin-332 deposition in the tumors, as did activated p110 subunit expression (FIG. 10a, fifth row), suggesting a possible link between G45 function, PI3-K pathway activation and laminin-332 deposition during SCC tumorigenesis.

Figure 11:
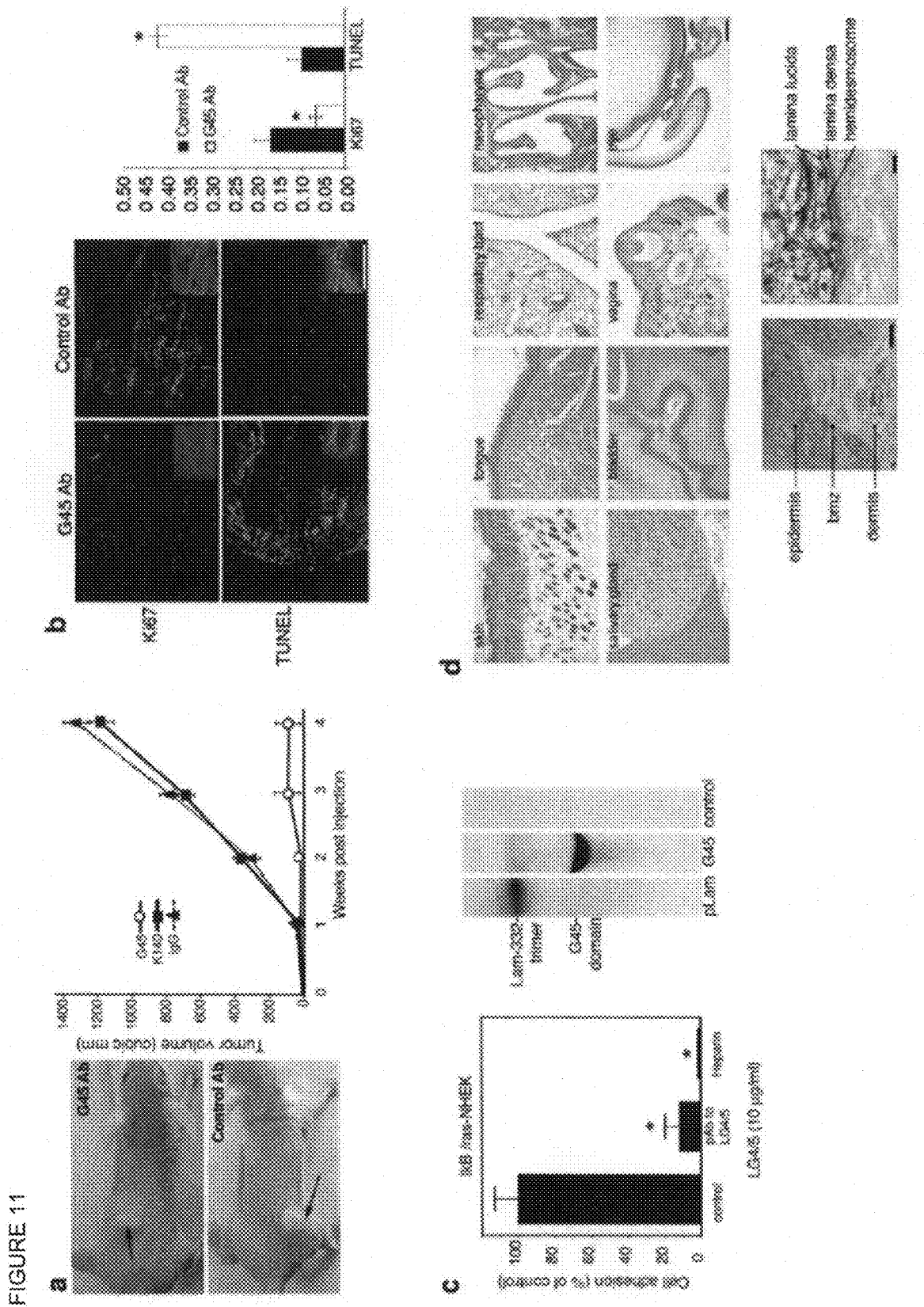
FIGS. 11A-11D. Laminin α3 G45 pAb inhibited human SCC tumorigenesis without disrupting normal epithelial adhesion. (a) G45 pAb blocked human tumorigenesis. Left: representative photos of Ras/IκBα-transformed SCC tumors in immunodeficient mice after 4 weeks of treatment with G45 pAb or control IgG. Right: quantification of tumor growth during weekly tumor volume measurements in-mice treated with G45 pAb, laminin β3 mAb K140 or control IgG. (b) Following 4 weeks of G45 pAb antibody injection, proliferation was reduced in tumors as shown by analysis of frozen tumor sections using immunofluorescence microscopy and Ki67 antibody. Left: proliferation was significantly reduced and apoptosis was greatly increased with G45 pAb treatment, as shown by Ki67 staining and TUNEL assay of frozen tumor sections; insets: Hoechst nuclear stain. Scale bar=100 µm. Right: quantification expressed as number of cells with Ki67 or TUNEL staining, respectively, as a percentage of total nuclei. All error bars=+/− SD, *=p-value<0.05 compared to control Ab (c) Left: Ras/IKBα transformed normal human epidermal keratinocytes (NHEK) were plated on dishes coated with recombinant laminin α3 G45 domain in the presence of 20 µg/ml control or affinity purified G45 IgG or heparin for one hour, then attached cells were analyzed by colorimetery and quantified as percentage of control. Right: laminin α3 G45 pAb reacted with native mouse laminin-332 as shown by nonreduced immunoblot of conditioned mouse keratinocyte medium using laminin-332 pAb (pLam), G45 pAb (G45) or nonimmune rabbit IgG (control). *=p-value<0.01 compared to control (d) Upper photos: Representative micrographs of G45 antibody treated mouse tissues known to express laminin-332 show no evidence of epithelial detachment or other histologic defects scale bar=200 µm. Lower photos: transmission electron microscopy of antibody treated mouse skin revealed no vesiculation or disruption of BMZ ultrastructure in representative samples. Left bar=5 µm, right bar=100 nm.

Laminin-332 G45 antibody disrupted SCC tumorigenesis in vivo without affecting normal tissue integrity. Over the course of 4 weeks of treatment, G45 antibodies dramatically inhibited in vivo human SCC tumorigenesis (FIG. 11a). G45 antibody treated tumors produced both inhibition of proliferation and pronounced apoptosis compared to control antibody treated tumors (FIG. 11b) similar to the G45 genetic deletion experiments described above. Affinity purified G45 antibody was shown to specifically inhibit transformed keratinocyte adhesion to recombinant G45 protein (FIG. 11c). Interestingly heparin also disrupted this interaction suggesting that the heparan binding-properties of G45 were involved in its cellular interactions. Given its inhibitory effects on SCC tumor growth, we recognized the potential of the G45 antibody as an anti-cancer agent, and looked for possible toxic side effects of the antibodies in a survey of normal tissues. Interestingly, although the G45 polyclonal antibody specifically recognized native murine laminin-332, as shown by nonreduced immunoblot analysis of conditioned mouse keratinocyte culture medium (FIG. 11c), we found no blistering, epithelial-mesenchymal separation or other morphologic abnormalities observed in laminin-332 expressing tissues of mice treated with G45 antibodies, even after four weeks of antibody injections (FIG. 11d). Transmission electron microscopy of mouse skin after four weeks of antibody treatment showed no vesiculation or BMZ abnormalities (FIG. 11d).

This study clearly indicates, through genetic and antibody mediated inhibition, a key role for laminin-332 G45 in SCC tumorigenesis. One of the striking aspects of this study was the stark contrast between undetectable G45 in normal mature tissues and prevalent accumulation of G45 in a wide array of squamous cell carcinomas. Over 75% of both cutaneous and non-cutaneous SCCs expressed laminin-332 and G45. Laminin-332 G45 was present in nearly 100% of human SCC tumors positive for total laminin-332 expression. Laminin-332 expression correlates with carcinoma invasiveness and a poor prognosis in SCC patients. As G45 persistence also correlates closely with laminin-332 expression in SCC tumors but is absent in normal tissues, G45, through additional clinical correlative studies, is an extremely useful marker to identify invasive SCC tumors.

Even though laminin-332 G45 is undetectable in mature tissues, it is transiently detectable at the leading edges of wounds. SCC invasion shares similarities with wound healing as both are processes of epithelial proliferation and extension which require the active synthesis and deposition of new BMZ components. These two processes differ in significant ways, however. In wounds, laminin-332 G45 becomes undetectable after closure, when synthesis of new BMZ components subsides and full processing and BMZ assembly is completed. With SCC tumor invasion, the synthesis of BMZ components is not regulated by a closure event such as in wound healing, and thus the synthesis of BMZ components continues, without allowing for processing and maturation of the BMZ to occur to completion. This may account for the poor ultrastructural BMZ organization in invasive carcinomas, compared to normal tissues.

Why G45 accumulates at SCCs and at the leading edges of healing wounds may simply be a reflection of higher levels of total laminin-332 expression. The enzymes which process laminin α3 chain include plasmin and the C-proteinase family of enzymes, especially mammalian tolloid and bone morphogenic protein 1. There may be other mechanisms which control the rate of laminin α3 G45 processing, such as the tissue plasminogen proteolytic cascade. In addition, a group of enhancer proteins which modulate C-proteinase activity has also been described, and while one, termed PCPE-1 has not been shown to influence laminin-332 processing, other members of this family, including PCPE-2 remain to be evaluated. As the G45 appears to have potent pro-tumorigenic effects, factors which influence its proteolytic removal may have important bearing on SCC tumor progression.

Major pro-tumorigenic effects of G45 include its ability to enhance laminin-332 deposition in SCC tumors. Laminin332 G45 domain has heparin binding properties, and may have the ability to bind with extracellular heparan sulfate proteoglycan BMZ components such as perlecan or dystroglycan. However, even in the absence of G45, laminin-332 deposition was shown to be restored to near wild type levels in SCC tumors through activation of the PI3-K pathway. This suggests that rather than acting by anchoring, G45 likely promotes laminin-332 deposition by a signaling mechanism perhaps induced through interaction with another cell surface receptor. As we showed our tumor cell interactions with G45 could be blocked with heparin, a candidate which deserves further study is syndecan-1, a transmembrane heparan sulfate proteoglycan receptor which is expressed in epidermal cells and can directly bind the laminin α3 G45 domain. The G45 domain appears to provide unique pro-tumorigenic functions, including laminin deposition and proliferative stimulation which are not provided by the laminin β3 chain short arm.

While G45 is not known to directly bind α6β4 integrin, a number of observations suggest that G45 and α6β4 integrin functions in promoting tumorigenesis may be related. First we noted that G45 and α6β4 integrin localized together in basal keratinocyte receptor complexes termed SAs. While α6β4 integrin is well known to play a key role in the formation of these complexes, here we also noted a role for G45 in SA formation. Specifically the absence of G45 disrupted the localization of SA complexes, changing them from central to peripheral localization. In addition to co-localizing to and playing a role in the formation of SAs, α6β4 integrin and G45 also showed interesting parallels of relevance to SCC tumorigenesis. G45 was noted for its promotion of cellular invasion and its activation of PI3-K and ERK signaling pathways, leading to protection from apoptosis and increased proliferation. It is also well known that α6β4 integrin, like G45, promotes carcinoma invasion and PI3-K pathway activation and nuclear ERK translocation which leads to increased proliferation. Furthermore α6β4 integrin was shown to perform these functions in a laminin dependent manner though its substrate domain. Deletion of this substrate domain led to phosphorylated ERK which accumulated in the cytoplasm, similar to ΔG45 cells in our study. Thus it is likely that α6β4 integrin and signaling from its substrate domain is involved in the function of the laminin α3 G45 domain. It should also be noted that in our studies, G45 promoted pro-tumorigenic functions best when it was expressed as part of the laminin α3 chain, suggesting G45 may need to be associated with the rest of the laminin-332 trimer for optimal function. It is possible that the close proximity of the G45 domain to the α6β4 integrin (G1-3) binding site on the unprocessed laminin α3 chain (FIG. 6a) plays a role in this process.

G45 domain clearly modulates the expression of MMP-9 and MMP-1, two metalloproteinases known to play important roles in carcinoma invasion. Our observation extends earlier findings of the G45 domain's role in upregulating MMP-1) and MMP-9 in keratinocytes to squamous carcinoma cells. These results are consistent with other studies showing the role of extracellular matrix molecules changing MMP expression and activities. Overexpression of PI3-K has been previously shown to promote MMP-9 expression in carcinoma cells and G45's ability to promote activation of the PI3-K pathway may be related to its function in promoting MMP-9 activity in human SCC.

G45 is not required for maintenance of normal tissue cohesion, as no epithelial-mesenchymal disruption was seen in normal tissues repeatedly treated with G45 inhibitory antibodies. Overall, its striking pro-tumorigenic activity, its prevalent accumulation in human SCC tumors and its absence and lack of function in normal developed tissues collectively make G45 an attractive anti-cancer target.

While the foregoing has presented specific embodiments, it is to be understood that these embodiments have been presented by way of example only. It is expected that others will perceive and practice variations which, though differing from the foregoing, do not depart form the spirit and scope of the inventions as described and claimed herein. All patent applications, patents, and literature references cited in this specification are hereby incorporated by reference in their entirety. In case of conflict or inconsistency, the present description, including definitions, will control.

What is claimed is:

1. A method of treating squamous cell carcinoma (SCC) in a patient comprising administering a therapeutically effective amount of one or more antibodies in a pharmaceutically acceptable carrier, wherein one or more of said antibodies is capable of specifically binding laminin 5 alpha 3 chain G4 and/or G5 domain or subdomain, and inhibiting SCC tumorigenesis.

2. A method according to claim 1, wherein said antibody binds to a polypeptide comprising the amino acid sequence of SEQ ID NO:13.

3. A method according to claim 1, wherein said antibody binds to a polypeptide comprising the amino acid sequence of SEQ ID NO:15.

4. A method according to claim 1, wherein said antibody binds to a polypeptide comprising the amino acid sequence of SEQ ID NO:17.

5. A method according to claim 1, wherein said antibody binds to a binds to a polypeptide comprising the amino acid sequence of SEQ ID NO:19.

6. A method according to claim 1, wherein said antibody binds to a polypeptide comprising the amino acid sequence of SEQ ID NO:21.

7. A method according to claim 1, wherein said antibody binds to a polypeptide comprising the amino acid sequence of SEQ ID NO:23.

8. A method according to claim 1, wherein said antibody is a polyclonal antibody.

9. A method according to claim 1, wherein said antibody is a monoclonal antibody.

10. A method according to claim 1, wherein said SCC is selected from the group consisting of skin cancer, lung cancer, head cancer, gastric cancer, colorectal, throat cancer, cancer of the urinary tract, cancer of the reproductive tract, esophageal cancer, and bronchiogenic carcinoma.

\* \* \* \* \*

SEQUENCE LISTING

<160> NUMBER OF SEQ ID NOS: 29

<210> SEQ ID NO 1
<211> LENGTH: 5433
<212> TYPE: DNA
<213> ORGANISM: Homo sapiens

<400> SEQUENCE: 1

```
atgggatggc tgtggatctt tggggcagcc ctggggcagt gtctgggcta cagttcacag      60
cagcaaaggg tgccatttct tcagcctccc ggtcaaagtc aactgcaagc gagttatgtg     120
gagtttagac ccagccaggg ttgtagccct ggatactatc gggatcataa aggcttgtat     180
```

```
accggacggt gtgttccctg caattgcaac ggacattcaa atcaatgcca ggatggctca    240
ggcatatgtg ttaactgtca gcacaacacc gcgggagagc actgtgaacg ctgccaggag    300
ggctactatg gcaacgccgt ccacggatcc tgcagggcct gcccatgtcc tcacactaac    360
agctttgcca ctggctgtgt ggtgaatggg ggagacgtgc ggtgctcctg caaagctggg    420
tacacaggaa cacagtgtga aggtgtgcca ccgggatatt tcgggaatcc ccagaaattc    480
ggaggtagct gccaaccatg cagttgtaac agcaatggcc agctgggcag ctgtcatccc    540
ctgactggag actgcataaa ccaagaaccc aaagatagca gccctgcaga agaatgtgat    600
gattgcgaca gctgtgtgat gaccctcctg aacgacctgg ccaccatggg cgagcagctc    660
cgcctggtca gtctcagct gcagggcctg agtgccagcg cagggcttct ggagcagatg    720
aggcacatgg agacccaggc caaggacctg aggaatcagt tgctcaacta ccgttctgcc    780
atttcaaatc atggatcaaa atagaaggc ctggaaagag aactgactga tttgaatcaa    840
gaatttgaga ctttgcaaga aaaggctcaa gtaaattcca gaaaagcaca acattaaac     900
aacaatgtta tcgggcaac acaaagcgca aaagaactgg atgtgaagat taaaaatgtc     960
atccggaatg tgcacattct tttaaagcag atctctggga cagatggaga gggaaacaac   1020
gtgccttcag gtgacttttc cagagagtgg gctgaagccc agcgcatgat gagggaactg   1080
cggaacagga actttggaaa gcacctcaga gaagcagaag ctgataaaag ggagtcgcag   1140
ctcttgctga accggataag gacctggcag aaaacccacc aggggagaa caatgggctt   1200
gctaacagta tccgggattc tttaaatgaa tacgaagcca aactcagtga ccttcgtgct   1260
cggctgcagg aggcagctgc ccaagccaag caggcaaatg cttgaacca agaaaacgag    1320
agagctttgg gagccattca gagacaagtg aaagaaataa attccctgca gagtgatttc   1380
accaagtatc taaccactgc agactcatct ttgttgcaaa ccaacattgc gctgcagctg   1440
atggagaaaa gccagaagga atatgaaaaa ttagctgcca gtttaaatga agcaagacaa   1500
gaactaagtg acaaagtaag agaactttcc agatctgctg gcaaaacatc ccttgtggag   1560
gaggcagaaa agcacgcgcg gtccttacaa gagctggcaa agcagctgga agagatcaag   1620
agaaacgcca gcggggatga gctggtgcgc tgtgctgtgg atgccgccac cgcctacgag   1680
aacatcctca tgccatcaa agcggccgag acgcagccaa acagggctgc cagtgcatct   1740
gaatctgccc tccagacagt gataaaggaa gatctgccaa gaaaagctaa aaccctgagt   1800
tccaacagtg ataaactgtt aaatgaagcc aagatgacac aaaagaagct aaagcaagaa   1860
gtcagtccag ctctcaacaa cctacagcaa accctgaata ttgtgacagt tcagaaagaa   1920
gtgatagaca ccaatctcac aactctccga atggtcttc atgggataca gagaggtgat   1980
attgatgcta tgatcagtag tgcaaagagc atggtcagaa aggccaacga catcacagat   2040
gaggttctgg atgggctcaa ccccatccag acagatgtgg aaagaattaa ggacaccctat  2100
gggaggacac agaacgaaga cttcaaaaag gctctgactg atgcagataa ctcggtgaat   2160
aagttaacca caaaactacc tgatctttgg cgcaagattg aaagtatcaa ccaacagctg   2220
ttgcccttgg gaaacatctc tgacaacatg gacagaatac gagaactaat tcagcaggcc   2280
agagatgctg ccagtaaggt tgctgtcccc atgaggttca atggtaaatc tggagtcgaa   2340
gtccgactgc caaatgacct ggaagatttg aaaggatata catctctgtc cttgtttctc   2400
caaaggccca actcaagaga aaatgggggt actgagaata tgtttgtgat gtaccttgga   2460
aataaagatg cctcccggga ctacatcggc atggcagttg tggatggcca gctcacctgt   2520
```

-continued

```
gtctacaacc tgggggaccg tgaggctgaa ctccaagtgg accagatctt gaccaagagt    2580
gagactaagg aggcagttat ggatcgggtg aaatttcaga gaatttatca gtttgcaagg    2640
cttaattaca ccaaaggagc cacatccagt aaaccagaaa cacccggagt ctatgacatg    2700
gatggtagaa atagcaatac actccttaat ttggatcctg aaaatgttgt attttatgtt    2760
ggaggttacc cacctgattt taaacttccc agtcgactaa gtttccctcc atacaaaggt    2820
tgtattgaat tagatgacct caatgaaaat gttctgagct tgtacaactt caaaaaaaca    2880
ttcaatctca acacaactga agtggagcct tgtagaagga ggaaggaaga gtcagacaaa    2940
aattattttg aaggtacggg ctatgctcga gttccaactc aaccacatgc tcccatccca    3000
acctttggac agacaattca gaccaccgtg gatagaggct tgctgttctt tgcagaaaac    3060
ggggatcgct tcatatctct aaatatagaa gatggcaagc tcatggtgag atacaaactg    3120
aattcagagc taccaaaaga gagaggagtt ggagacgcca taaacaacgg cagagaccat    3180
tcgattcaga tcaaaattgg aaaactccaa aagcgtatgt ggataaatgt ggacgttcaa    3240
aacactataa ttgatggtga agtatttgat ttcagcacat attatctggg aggaattcca    3300
attgcaatca gggaaagatt taacatttct acgcctgctt tccgaggctg catgaaaaat    3360
ttgaagaaaa ccagtggtgt cgttagattg aatgatactg tgggagtaac caaaaagtgc    3420
tcggaagact ggaagcttgt gcgatctgcc tcattctcca gaggaggaca attgagtttc    3480
actgatttgg gcttaccacc tactgaccac ctccaggcct catttggatt tcagacctt    3540 caacccagtg gcatattatt agatcatcag acatggacaa ggaacctgca ggtcactctg    3600
gaagatggtt acattgaatt gagcaccagc gatagcggcg cccaatttt taaatctcca    3660 cagacgtata tggatggttt actgcattat gtatctgtaa taagcgacaa ctctggacta    3720
cggcttctca tcgatgacca gcttctgaga aatagcaaaa ggctaaaaca catttcaagt    3780
tcccggcagt ctctgcgtct gggcgggagc aattttgagg gttgtattag caatgttttt    3840
gtccagaggt tatcactgag tcctgaagtc ctagatttga ccagtaactc tctcaagaga    3900
gatgtgtccc tgggaggctg cagttttaaac aaaccaccctt ttctaatgtt gcttaaaggt    3960
tctaccaggt ttaacaagac caagactttt cgtatcaacc agctgttgca ggacacacca    4020
gtggcctccc caaggagcgt gaaggtgtgg caagatgctt gctcaccact tcccaagacc    4080
caggccaatc atggagccct ccagtttggg gacattccca ccagccactt gctattcaag    4140
cttcctcagg agctgctgaa acccaggtca cagtttgctg tggacatgca gacaacatcc    4200
tccagaggac tggtgtttca cacgggcact aagaactcct ttatggctct ttatcttca    4260 aaaggacgtc tggtctttgc actggggaca gatgggaaaa aattgaggat caaaagcaag    4320
gagaaatgca atgatgggaa atggcacacg gtggtgttg gccatgatgg ggaaaagggg    4380
cgcttggttg tggatggact gagggcccgg gagggaagtt tgcctggaaa ctccaccatc    4440 agcatcgag cgccagttta cctgggatca cctccatcag ggaaaccaaa gagcctcccc    4500
acaaacagct ttgtgggatg cctgaagaac tttcagctgg attcaaaacc cttgtatacc    4560
ccttcttcaa gcttcgggt gtcttcctgc ttgggtggtc ctttggagaa aggcatttat    4620
ttctctgaag aaggaggtca tgtcgtcttg gctcactctg tattgttggg gccagaattt    4680
aagcttgttt tcagcatccg cccaagaagt ctcactggga tcctaataca catcggaagt    4740
cagcccggga agcacttatg tgtttacctg gaggcaggaa aggtcacggc ctctatggac    4800
agtggggcag gtgggacctc aacgtcggtc acaccaaagc agtctctgtg tgatggacag    4860
tggcactcgg tggcagtcac cataaaacaa cacatcctgc acctggaact ggacacagac    4920
```

-continued

```
agtagctaca cagctggaca gatcccttc ccacctgcca gcactcaaga gccactacac    4980
cttggaggtg ctccagccaa tttgacgaca ctgaggatcc ctgtgtggaa atcattcttt    5040
ggctgtctga ggaatattca tgtcaatcac atccctgtcc ctgtcactga agccttggaa    5100 gtccagggc ctgtcagtct gaatggttgt cctgaccagt aacccaagcc tatttcacag    5160
caaggaaatt caccttcaaa agcactgatt acccaatgca cctccctccc cagctcgaga    5220
tcattcttca attaggacac aaaccagaca ggtttaatag cgaatctaat tttgaattct    5280
gaccatggat acccatcact ttggcattca gtgctacatg tgtattttat ataaaaatcc    5340
catttcttga agataaaaaa attgttattc aaattgttat gcacagaatg ttttggtaa    5400 tattaatttc cactaaaaaa ttaaatgtct ttt                                5433

<210> SEQ ID NO 2
<211> LENGTH: 1713
<212> TYPE: PRT
<213> ORGANISM: Homo sapiens

<400> SEQUENCE: 2

Met Gly Trp Leu Trp Ile Phe Gly Ala Ala Leu Gly Gln Cys Leu Gly
  1               5                  10                  15

Tyr Ser Ser Gln Gln Gln Arg Val Pro Phe Leu Gln Pro Pro Gly Gln
             20                  25                  30

Ser Gln Leu Gln Ala Ser Tyr Val Glu Phe Arg Pro Ser Gln Gly Cys
         35                  40                  45

Ser Pro Gly Tyr Tyr Arg Asp His Lys Gly Leu Tyr Thr Gly Arg Cys
     50                  55                  60

Val Pro Cys Asn Cys Asn Gly His Ser Asn Gln Cys Gln Asp Gly Ser
 65                  70                  75                  80

Gly Ile Cys Val Asn Cys Gln His Asn Thr Ala Gly Glu His Cys Glu
                 85                  90                  95

Arg Cys Gln Glu Gly Tyr Tyr Gly Asn Ala Val His Gly Ser Cys Arg
            100                 105                 110

Ala Cys Pro Cys Pro His Thr Asn Ser Phe Ala Thr Gly Cys Val Val
        115                 120                 125

Asn Gly Gly Asp Val Arg Cys Ser Cys Lys Ala Gly Tyr Thr Gly Thr
    130                 135                 140

Gln Cys Glu Arg Cys Ala Pro Gly Tyr Phe Gly Asn Pro Gln Lys Phe
145                 150                 155                 160

Gly Gly Ser Cys Gln Pro Cys Ser Cys Asn Ser Asn Gly Gln Leu Gly
                165                 170                 175

Ser Cys His Pro Leu Thr Gly Asp Cys Ile Asn Gln Glu Pro Lys Asp
            180                 185                 190

Ser Ser Pro Ala Glu Glu Cys Asp Asp Cys Asp Ser Cys Val Met Thr
        195                 200                 205

Leu Leu Asn Asp Leu Ala Thr Met Gly Glu Gln Leu Arg Leu Val Lys
    210                 215                 220

Ser Gln Leu Gln Gly Leu Ser Ala Ser Ala Gly Leu Leu Glu Gln Met
225                 230                 235                 240

Arg His Met Glu Thr Gln Ala Lys Asp Leu Arg Asn Gln Leu Leu Asn
                245                 250                 255

Tyr Arg Ser Ala Ile Ser Asn His Gly Ser Lys Ile Glu Gly Leu Glu
            260                 265                 270

Arg Glu Leu Thr Asp Leu Asn Gln Glu Phe Glu Thr Leu Gln Glu Lys
```

-continued

```
                275                 280                 285
Ala Gln Val Asn Ser Arg Lys Ala Gln Thr Leu Asn Asn Val Asn
            290                 295                 300
Arg Ala Thr Gln Ser Ala Lys Glu Leu Asp Val Lys Ile Lys Asn Val
305                 310                 315                 320
Ile Arg Asn Val His Ile Leu Lys Gln Ile Ser Gly Thr Asp Gly
                325                 330                 335
Glu Gly Asn Asn Val Pro Ser Gly Asp Phe Ser Arg Glu Trp Ala Glu
                340                 345                 350
Ala Gln Arg Met Met Arg Glu Leu Arg Asn Arg Asn Phe Gly Lys His
                355                 360                 365
Leu Arg Glu Ala Glu Ala Asp Lys Arg Glu Ser Gln Leu Leu Leu Asn
    370                 375                 380
Arg Ile Arg Thr Trp Gln Lys Thr His Gln Gly Glu Asn Asn Gly Leu
385                 390                 395                 400
Ala Asn Ser Ile Arg Asp Ser Leu Asn Glu Tyr Glu Ala Lys Leu Ser
                405                 410                 415
Asp Leu Arg Ala Arg Leu Gln Glu Ala Ala Gln Ala Lys Gln Ala
                420                 425                 430
Asn Gly Leu Asn Gln Glu Asn Glu Arg Ala Leu Gly Ala Ile Gln Arg
                435                 440                 445
Gln Val Lys Glu Ile Asn Ser Leu Gln Ser Asp Phe Thr Lys Tyr Leu
    450                 455                 460
Thr Thr Ala Asp Ser Ser Leu Leu Gln Thr Asn Ile Ala Leu Gln Leu
465                 470                 475                 480
Met Glu Lys Ser Gln Lys Glu Tyr Glu Lys Leu Ala Ala Ser Leu Asn
                485                 490                 495
Glu Ala Arg Gln Glu Leu Ser Asp Lys Val Arg Glu Leu Ser Arg Ser
            500                 505                 510
Ala Gly Lys Thr Ser Leu Val Glu Ala Glu Lys His Ala Arg Ser
            515                 520                 525
Leu Gln Glu Leu Ala Lys Gln Leu Glu Glu Ile Lys Arg Asn Ala Ser
    530                 535                 540
Gly Asp Glu Leu Val Arg Cys Ala Val Asp Ala Ala Thr Ala Tyr Glu
545                 550                 555                 560
Asn Ile Leu Asn Ala Ile Lys Ala Ala Glu Asp Ala Ala Asn Arg Ala
                565                 570                 575
Ala Ser Ala Ser Glu Ser Ala Leu Gln Thr Val Ile Lys Glu Asp Leu
            580                 585                 590
Pro Arg Lys Ala Lys Thr Leu Ser Ser Asn Ser Asp Lys Leu Leu Asn
            595                 600                 605
Glu Ala Lys Met Thr Gln Lys Lys Leu Lys Gln Glu Val Ser Pro Ala
    610                 615                 620
Leu Asn Asn Leu Gln Gln Thr Leu Asn Ile Val Thr Val Gln Lys Glu
625                 630                 635                 640
Val Ile Asp Thr Asn Leu Thr Thr Leu Arg Asp Gly Leu His Gly Ile
                645                 650                 655
Gln Arg Gly Asp Ile Asp Ala Met Ile Ser Ser Ala Lys Ser Met Val
            660                 665                 670
Arg Lys Ala Asn Asp Ile Thr Asp Glu Val Leu Asp Gly Leu Asn Pro
    675                 680                 685
Ile Gln Thr Asp Val Glu Arg Ile Lys Asp Thr Tyr Gly Arg Thr Gln
    690                 695                 700
```

```
Asn Glu Asp Phe Lys Lys Ala Leu Thr Asp Ala Asp Asn Ser Val Asn
705                 710                 715                 720

Lys Leu Thr Asn Lys Leu Pro Asp Leu Trp Arg Lys Ile Glu Ser Ile
            725                 730                 735

Asn Gln Gln Leu Leu Pro Leu Gly Asn Ile Ser Asp Asn Met Asp Arg
                740                 745                 750

Ile Arg Glu Leu Ile Gln Gln Ala Arg Asp Ala Ala Ser Lys Val Ala
            755                 760                 765

Val Pro Met Arg Phe Asn Gly Lys Ser Gly Val Glu Val Arg Leu Pro
770                 775                 780

Asn Asp Leu Glu Asp Leu Lys Gly Tyr Thr Ser Leu Ser Leu Phe Leu
785                 790                 795                 800

Gln Arg Pro Asn Ser Arg Glu Asn Gly Gly Thr Glu Asn Met Phe Val
                805                 810                 815

Met Tyr Leu Gly Asn Lys Asp Ala Ser Arg Asp Tyr Ile Gly Met Ala
                820                 825                 830

Val Val Asp Gly Gln Leu Thr Cys Val Tyr Asn Leu Gly Asp Arg Glu
            835                 840                 845

Ala Glu Leu Gln Val Asp Gln Ile Leu Thr Lys Ser Glu Thr Lys Glu
850                 855                 860

Ala Val Met Asp Arg Val Lys Phe Gln Arg Ile Tyr Gln Phe Ala Arg
865                 870                 875                 880

Leu Asn Tyr Thr Lys Gly Ala Thr Ser Ser Lys Pro Glu Thr Pro Gly
            885                 890                 895

Val Tyr Asp Met Asp Gly Arg Asn Ser Asn Thr Leu Leu Asn Leu Asp
            900                 905                 910

Pro Glu Asn Val Val Phe Tyr Val Gly Gly Tyr Pro Pro Asp Phe Lys
            915                 920                 925

Leu Pro Ser Arg Leu Ser Phe Pro Pro Tyr Lys Gly Cys Ile Glu Leu
            930                 935                 940

Asp Asp Leu Asn Glu Asn Val Leu Ser Leu Tyr Asn Phe Lys Lys Thr
945                 950                 955                 960

Phe Asn Leu Asn Thr Thr Glu Val Glu Pro Cys Arg Arg Lys Glu
                965                 970                 975

Glu Ser Asp Lys Asn Tyr Phe Glu Gly Thr Gly Tyr Ala Arg Val Pro
            980                 985                 990

Thr Gln Pro His Ala Pro Ile Pro Thr Phe Gly Gln Thr Ile Gln Thr
            995                 1000                1005

Thr Val Asp Arg Gly Leu Leu Phe Phe Ala Glu Asn Gly Asp Arg Phe
    1010                1015                1020

Ile Ser Leu Asn Ile Glu Asp Gly Lys Leu Met Val Arg Tyr Lys Leu
1025                1030                1035                1040

Asn Ser Glu Leu Pro Lys Glu Arg Gly Val Gly Asp Ala Ile Asn Asn
                1045                1050                1055

Gly Arg Asp His Ser Ile Gln Ile Lys Ile Gly Lys Leu Gln Lys Arg
            1060                1065                1070

Met Trp Ile Asn Val Asp Val Gln Asn Thr Ile Ile Asp Gly Glu Val
            1075                1080                1085

Phe Asp Phe Ser Thr Tyr Tyr Leu Gly Gly Ile Pro Ile Ala Ile Arg
            1090                1095                1100

Glu Arg Phe Asn Ile Ser Thr Pro Ala Phe Arg Gly Cys Met Lys Asn
1105                1110                1115                1120
```

-continued

```
Leu Lys Lys Thr Ser Gly Val Val Arg Leu Asn Asp Thr Val Gly Val
            1125                1130                1135

Thr Lys Lys Cys Ser Glu Asp Trp Lys Leu Val Arg Ser Ala Ser Phe
            1140                1145                1150

Ser Arg Gly Gly Gln Leu Ser Phe Thr Asp Leu Gly Leu Pro Pro Thr
            1155                1160                1165

Asp His Leu Gln Ala Ser Phe Gly Phe Gln Thr Phe Gln Pro Ser Gly
            1170                1175                1180

Ile Leu Leu Asp His Gln Thr Trp Thr Arg Asn Leu Gln Val Thr Leu
1185                1190                1195                1200

Glu Asp Gly Tyr Ile Glu Leu Ser Thr Ser Asp Ser Gly Gly Pro Ile
            1205                1210                1215

Phe Lys Ser Pro Gln Thr Tyr Met Asp Gly Leu Leu His Tyr Val Ser
            1220                1225                1230

Val Ile Ser Asp Asn Ser Gly Leu Arg Leu Leu Ile Asp Asp Gln Leu
            1235                1240                1245

Leu Arg Asn Ser Lys Arg Leu Lys His Ile Ser Ser Ser Arg Gln Ser
            1250                1255                1260

Leu Arg Leu Gly Gly Ser Asn Phe Glu Gly Cys Ile Ser Asn Val Phe
1265                1270                1275                1280

Val Gln Arg Leu Ser Leu Ser Pro Glu Val Leu Asp Leu Thr Ser Asn
            1285                1290                1295

Ser Leu Lys Arg Asp Val Ser Leu Gly Gly Cys Ser Leu Asn Lys Pro
            1300                1305                1310

Pro Phe Leu Met Leu Lys Gly Ser Thr Arg Phe Asn Lys Thr Lys
            1315                1320                1325

Thr Phe Arg Ile Asn Gln Leu Leu Gln Asp Thr Pro Val Ala Ser Pro
            1330                1335                1340

Arg Ser Val Lys Val Trp Gln Asp Ala Cys Ser Pro Leu Pro Lys Thr
1345                1350                1355                1360

Gln Ala Asn His Gly Ala Leu Gln Phe Gly Asp Ile Pro Thr Ser His
            1365                1370                1375

Leu Leu Phe Lys Leu Pro Gln Glu Leu Leu Lys Pro Arg Ser Gln Phe
            1380                1385                1390

Ala Val Asp Met Gln Thr Thr Ser Ser Arg Gly Leu Val Phe His Thr
            1395                1400                1405

Gly Thr Lys Asn Ser Phe Met Ala Leu Tyr Leu Ser Lys Gly Arg Leu
            1410                1415                1420

Val Phe Ala Leu Gly Thr Asp Gly Lys Lys Leu Arg Ile Lys Ser Lys
1425                1430                1435                1440

Glu Lys Cys Asn Asp Gly Lys Trp His Thr Val Val Phe Gly His Asp
            1445                1450                1455

Gly Glu Lys Gly Arg Leu Val Val Asp Gly Leu Arg Ala Arg Glu Gly
            1460                1465                1470

Ser Leu Pro Gly Asn Ser Thr Ile Ser Ile Arg Ala Pro Val Tyr Leu
            1475                1480                1485

Gly Ser Pro Pro Ser Gly Lys Pro Lys Ser Leu Pro Thr Asn Ser Phe
            1490                1495                1500

Val Gly Cys Leu Lys Asn Phe Gln Leu Asp Ser Lys Pro Leu Tyr Thr
1505                1510                1515                1520

Pro Ser Ser Ser Phe Gly Val Ser Ser Cys Leu Gly Gly Pro Leu Glu
            1525                1530                1535

Lys Gly Ile Tyr Phe Ser Glu Glu Gly Gly His Val Val Leu Ala His
```

-continued

```
                1540                1545                1550
Ser Val Leu Leu Gly Pro Glu Phe Lys Leu Val Phe Ser Ile Arg Pro
        1555                1560                1565
Arg Ser Leu Thr Gly Ile Leu Ile His Ile Gly Ser Gln Pro Gly Lys
        1570                1575                1580
His Leu Cys Val Tyr Leu Glu Ala Gly Lys Val Thr Ala Ser Met Asp
1585                1590                1595                1600
Ser Gly Ala Gly Gly Thr Ser Thr Ser Val Thr Pro Lys Gln Ser Leu
            1605                1610                1615
Cys Asp Gly Gln Trp His Ser Val Ala Val Thr Ile Lys Gln His Ile
        1620                1625                1630
Leu His Leu Glu Leu Asp Thr Asp Ser Ser Tyr Thr Ala Gly Gln Ile
        1635                1640                1645
Pro Phe Pro Pro Ala Ser Thr Gln Glu Pro Leu His Leu Gly Gly Ala
        1650                1655                1660
Pro Ala Asn Leu Thr Thr Leu Arg Ile Pro Val Trp Lys Ser Phe Phe
1665                1670                1675                1680
Gly Cys Leu Arg Asn Ile His Val Asn His Ile Pro Val Pro Val Thr
            1685                1690                1695
Glu Ala Leu Glu Val Gln Gly Pro Val Ser Leu Asn Gly Cys Pro Asp
            1700                1705                1710
Gln

<210> SEQ ID NO 3
<211> LENGTH: 10511
<212> TYPE: DNA
<213> ORGANISM: Homo sapiens

<400> SEQUENCE: 3
gcaggtccgg gaggcgcagg cggagagcgg cggtgccccc gagcccctct gcggacggct      60
caggcgggag gaccccgcgc ggctggatgg cggcggccgc gcggcctcgg ggtcgggcac     120
tggggccagt actgccgccg acgccgctgc tcctgctggt actgcgggtg ctgccagcct     180
gcggggcgac cgctcgggat cccggggccg cggccgggct cagccttcac ccgacttact     240
tcaacctggc cgaggcggcg aggatttggg ccaccgccac ctgcggggag aggggacccg     300
gcgaggggag gccccagccc gagctctact gcaagttggt cggggccccc accgcccag     360
gcagcggcca caccatccag ggccagttct gtgactattg caattctgaa gaccccagga     420
aagcacatcc tgtcaccaat gccatcgatg gatctgaacg ttggtggcaa agccctcccc     480
tgtcctcagg cacacagtac aacagagtca acctcaccct ggatctgggg cagctcttcc     540
atgtggccta tattttaatc aaatttgcaa attctcctcg ccctgatctt tgggtcttgg     600
aaagatctgt agactttgga agcacctact caccatggca atattttgct cattctaaag     660
tagactgttt aaaagaattt gggcgggagg caaatatggc tgtcacccgg gatgatgatg     720
tactttgtgt tactgaatat tcccgtattg taccttttgga aaatggtgag gttgtggtgt     780
ccttgataaa cggtcgtcca ggtgcaaaaa attttacttt ctctcacacc ctgagggagt     840
ttaccaaggc aacaaacatc cgcttgcgtt ttcttagaac caatacgctt cttggacacc     900
tcatctccaa agcccagcga gatccaactg tcactcggcg gtattattac agcataaagg     960
acatcagcat tggtgggcag tgtgtttgca atggccatgc tgaagtgtgc aatataaaca    1020
atcctgaaaa actgtttcgg tgtgaatgcc agcaccacac ctgtggggag acgtgtgatc    1080
gctgctgcac agggtacaat cagaggcgct ggcggcccgc cgcttgggag cagagccacg    1140
```

-continued

```
agtgtgaagc atgcaactgc cacggccatg ccagcaactg ttactatgat ccagatgttg    1200
agcggcagca ggcaagcttg aatacccagg gcatctatgc tggtggaggg gtctgcatta    1260
actgtcagca caacacagct ggagtaaact gtgaacagtg tgctaagggc tattaccgcc    1320
cttatggggt tccagtggat gccctgatg gctgcatccc ctgcagctgt gaccctgagc     1380
atgcggatgg ctgtgaacag ggttcaggcc gctgtcactg caagccaaat ttccacggag    1440
acaactgtga gaagtgtgca attggatact acaatttccc attttgcttg agaattccca    1500
tttttcctgt ttctacacca agttcagaag atccagtagc tggagatata aagggtgtg    1560 actgtaatct ggaaggtgtt ctccctgaaa tatgtgatgc ccacggacgg tgcctgtgcc    1620
gccctggggt tgagggccct cgatgtgata cctgccgctc tggtttctac tcattcccta    1680
tttgccaagc tgctggtgt tcagcccttg atcctacca gatgccctgc agctcagtga     1740
ctggacagtg tgaatgtcgg ccaggagtta caggacagcg tgtgacagg tgtctctcag     1800 gagcttatga tttcccccac tgccaaggtt ccagcagtgc ttgtgaccca gctggtacca    1860
tcaactccaa tttggggtat tgccaatgca agcttcatgt tgaaggtcct acttgtagcc    1920
gctgcaaact gttatattgg aatctggaca agaaaaccc cagtggatgt tcagaatgca    1980
agtgccataa ggcgggaaca gtgagtgaa ctggagagtg taggcaggga gatggtgact    2040
gtcactgcaa gtcccatgtg ggtggcgatt cctgcgacac ctgtgaagat ggatattttg    2100
ctttggaaaa gagcaattac tttgggtgtc aagggtgtca gtgtgacatt ggtgggcat    2160 tgtcctccat gtgcagtggg ccctcgggag tgtgccagtg ccgagagcat gtcgtgggaa    2220
aggtgtgcca gcggcctgaa acaactact atttcccaga tttgcatcat atgaagtatg     2280
agattgaaga cggcagcaca cctaatggga gagaccttcg atttggattt gatccgctgg    2340
catttcctga gtttagctgg agaggatatg cccaaatgac ctcagtacag aatgatgtaa    2400
gaataacatt gaatgtaggg aagtcaagtg gctccttgtt tcgtgttatt ctgagatacg    2460
ttaaccctgg aactgaagca gtatctggcc atataactat ttatccatcc tggggtgctg    2520
ctcaaagcaa agagatcatc ttcctgccga gtaaggagcc agcctttgtc actgtccctg    2580
gaaatggttt tgcagaccca ttttcaatca caccaggaat atgggttgct tgtattaagg    2640
cagaaggagt ccttctggat tacctggtgc tgctccccag ggactactat gaagcctctg    2700
tactgcagct gccagtcaca gaaccatgtg cctacgcagg acctcccaa gaaaattgct    2760 tactctacca gcatttgcca gtgaccagat tccctgtac cctggcttgt gaggccagac    2820
acttcctgct tgatggggag ccaagaccg tggcagtgag gcagcccaca cctgcacacc     2880
ctgtcatggt ggacctcagc gggagagagg tggaattgca tctgcggctg cgcatcccac    2940
aggttggcca ctacgtggtt gtggtcgagt attccacgga ggcagctcag ctgtttgtgg    3000
ttgatgtgaa tgtgaagagc tccgggtctg ttctggcagg ccaggtgaac atttacagct    3060
gcaactacag tgttctctgc cggagtgctg tgattgatca catgagccgc atcgccatgt    3120
atgagctatt ggcagatgca gacattcagc tcaaggaca catggcccga ttccttctgc    3180
atcaagtttg tatcataccct attgaagaat tctcagctga gtatgtgaga ccacaagtcc    3240
actgcattgc cagttatggg cgatttgtca atcaaagtgc cacctgtgtc tccttggccc    3300
atgaaactcc tccaacagca ttaattttgg atgttctaag tggcaggcct ttccctcacc    3360
tgccccagca gtcgtcacct tctgttgatg ttcttcctgg ggtcaccttg aaggcaccgc    3420
agaatcaagt gaccctgaga ggacgtgtac cacacctggg ccgatacgtc tttgtcatcc    3480
```

```
attttttacca agcagcgcac ccgacgtttc ccgcgcaggt gtcggtggat ggcgggtggc    3540
cacgggcagg ctccttccat gcctcttttt gcccccatgt gcttggctgc cgggatcaag    3600
tgattgccga aggccagatt gagtttgaca tctcagagcc tgaagtggcc gcaactgtga    3660
aggttccaga aggaaagtcc ttggttttgg tccgtgttct agtggtgcct gcagaaaact    3720
atgactacca aatacttcac aaaaaatcca tggacaagtc actcgagttt atcaccaatt    3780
gtggaaaaaa cagcttttac cttgaccccc agacagcctc cagattctgt aagaattccg    3840
ccaggtccct ggtggccttt taccacaagg gcgccctgcc ttgtgagtgc caccccactg    3900
gggccaccgg ccctcactgc agccctgagg gtgggcagtg cccatgccag cccaacgtca    3960
tcgggcggca gtgcacccgc tgtgcaacag gccactacgg attcccacgc tgcaagccgt    4020
gcagctgtgg tcggcgcctt tgtgaagaga tgacggggca gtgccgctgc cctccccgca    4080
cggtcaggcc ccagtgtgag gtgtgtgaga cacactcatt cagcttccac cccatggccg    4140
gctgcgaagg ctgcaactgt tccaggaggg gcaccatcga ggctgccatg ccggagtgtg    4200
accgggacag cgggcagtgc agatgcaagc ccagaatcac agggcggcag tgtgaccgat    4260
gtgcttccgg gttttaccgc tttcctgagt gtgttccctg caattgcaac agagatggga    4320
ctgagccagg agtgtgtgac ccagggaccg gggcttgcct ctgcaaggaa aatgtagaag    4380
gcacagagtg taatgtgtgt cgagaaggct cattccattt ggacccagcc aatctcaagg    4440
gttgtaccag ctgtttctgt tttggagtaa ataatcaatg tcacagctca cataagcgaa    4500
ggactaagtt tgtggatatg ctgggctggc acctggagac agcagacaga gtggacatcc    4560
ctgtctcttt caacccaggc agcaacagta tggtggcgga tctccaggag ctgcccgcaa    4620
ccatccacag cgcgtcctgg gtcgcaccca cctcctacct gggggacaag gtttcttcat    4680
atggtggtta cctcacttac caagccaagt cctttggctt gcctggcgac atggttcttc    4740
tggaaaagaa gccggatgta cagctcactg gtcagcacat gtccatcatc tatgaggaga    4800
caaacacccc acggccagac cggctgcatc atggacgagt gcacgtggtc gagggaaact    4860
tcagacatgc cagcagccgt gccccagtgt ctagggagga gctgatgaca gtgctgtcta    4920
gactggcaga tgtgcgcatc caaggcctct acttcacaga gactcaaagg ctcaccctga    4980
gcgaggtggg gctagaggaa gcctctgaca caggaagtgg gcgcatagca cttgctgtgg    5040
aaatctgtgc ctgccccccct gcctacgctg gtgactcttg tcagggttgt agccctggat    5100
actatcggga tcataaaggc ttgtataccg gacggtgtgt tccctgcaat tgcaacggac    5160
attcaaatca atgccaggat ggctcaggca tatgtgttaa ctgtcagcac aacaccgcgg    5220
gagagcactg tgaacgctgc caggagggct actatggcaa cgccgtccac ggatcctgca    5280
gggcctgccc atgtcctcac actaacagct ttgccactgg ctgtgtggtg aatggggag    5340
acgtgcggtg ctcctgcaaa gctgggtaca caggaacaca gtgtgaaagg tgtgcaccgg    5400
gatatttcgg gaatccccag aaattcggag gtagctgcca accatgcagt tgtaacagca    5460
atggccagct gggcagctgt catcccctga ctggagactg cataaaccaa gaacccaaag    5520
atagcagccc tgcagaagaa tgtgatgatt gcgacagctg tgtgatgacc ctcctgaacg    5580
acctggccac catgggcgag cagctccgcc tggtcaagtc tcagctgcag ggcctgagtg    5640
ccagcgcagg gcttctggag cagatgaggc acatggagac ccaggccaag gacctgagga    5700
atcagttgct caactaccgt tctgccattt caaatcatgg atcaaaaata gaaggcctgg    5760
aaagagaact gactgatttg aatcaagaat ttgagacttt gcaagaaaag gctcaagtaa    5820
attccagaaa agcacaaaca ttaaacaaca atgttaatcg ggcaacacaa agcgcaaaag    5880
```

```
aactggatgt gaagattaaa aatgtcatcc ggaatgtgca cattcttta  aagcagatct    5940
ctgggacaga tggagaggga acaacgtgc  cttcaggtga cttttccaga gagtgggctg    6000
aagcccagcg catgatgagg gaactgcgga acaggaactt tggaaagcac ctcagagaag    6060
cagaagctga taaagggag  tcgcagctct tgctgaaccg gataaggacc tggcagaaaa    6120
cccaccaggg ggagaacaat gggcttgcta acagtatccg ggattcttta aatgaatacg    6180
aagccaaact cagtgacctt cgtgctcggc tgcaggaggc agctgcccaa gccaagcagg    6240
caaatggctt gaaccaagaa acgagagag  ctttgggagc cattcagaga caagtgaaag    6300
aaataaattc cctgcagagt gatttcacca agtatctaac cactgcagac tcatctttgt    6360
tgcaaaccaa cattgcgctg cagctgatgg agaaaagcca aaggaatat  gaaaaattag    6420
ctgccagttt aaatgaagca agacaagaac taagtgacaa agtaagagaa ctttccagat    6480
ctgctggcaa acatccctt  gtggaggagg cagaaaagca cgcgcggtcc ttacaagagc    6540
tggcaaagca gctggaagag atcaagagaa acgccagcgg ggatgagctg gtgcgctgtg    6600
ctgtggatgc cgccaccgcc tacgagaaca tcctcaatgc catcaaagcg gccgaggacg    6660
cagccaacag ggctgccagt gcatctgaat ctgccctcca gacagtgata aaggaagatc    6720
tgccaagaaa agctaaaacc ctgagttcca acagtgataa actgttaaat gaagccaaga    6780
tgacacaaaa gaagctaaag caagaagtca gtccagctct caacaaccta cagcaaaccc    6840
tgaatattgt gacagttcag aaagaagtga tagacaccaa tctcacaact ctccgagatg    6900
gtcttcatgg gatacagaga ggtgatattg atgctatgat cagtagtgca aagagcatgg    6960
tcagaaaggc caacgacatc acagatgagg ttctggatgg gctcaacccc atccagacag    7020
atgtggaaag aattaaggac acctatggga ggacacagaa cgaagacttc aaaaaggctc    7080
tgactgatgc agataactcg gtgaataagt taaccaacaa actacctgat ctttggcgca    7140
agattgaaag tatcaaccaa cagctgttgc ccttgggaaa catctctgac aacatggaca    7200
gaatacgaga actaattcag caggccagag atgctgccag taaggttgct gtccccatga    7260
ggttcaatgg taaatctgga gtcgaagtcc gactgccaaa tgacctggaa gatttgaaag    7320
gatatacatc tctgtccttg ttctccaaa  ggcccaactc aagagaaaat ggggtactg    7380
agaatatgtt tgtgatgtac cttggaaata agatgcctc  ccgggactac atcggcatgg    7440
cagttgtgga tggccagctc acctgtgtct acaacctggg ggaccgtgag gctgaactcc    7500
aagtggacca gatcttgacc aagagtgaga ctaaggaggc agttatggat cgggtgaaat    7560
ttcagagaat ttatcagttt gcaaggctta attacaccaa aggagccaca tccagtaaac    7620
cagaaacacc cggagtctat gacatggatg gtagaaatag caatacactc cttaatttgg    7680
atcctgaaaa tgttgtattt tatgttggag gttacccacc tgattttaaa cttcccagtc    7740
gactaagttt ccctccatac aaaggttgta ttgaattaga tgacctcaat gaaaatgttc    7800
tgagcttgta caacttcaaa aaaacattca atctcaacac aactgaagtg agccttgta    7860
gaaggaggaa ggaagagtca gacaaaaatt atttttgaagg tacgggctat gctcgagttc    7920
caactcaacc acatgctccc atcccaacct ttggacagac aattcagacc accgtggata    7980
gaggcttgct gttctttgca gaaaacgggg atcgcttcat atctctaaat atagaagatg    8040
gcaagctcat ggtgagatac aaactgaatt cagagctacc aaaagagaga ggagttggag    8100
acgccataaa caacggcaga gaccattcga ttcagatcaa aattggaaaa ctccaaaagc    8160
gtatgtggat aaatgtggac gttcaaaaca ctataattga tggtgaagta tttgatttca    8220
```

```
gcacatatta tctgggagga attccaattg caatcaggga aagatttaac atttctacgc    8280
ctgctttccg aggctgcatg aaaaatttga agaaaaccag tggtgtcgtt agattgaatg    8340
atactgtggg agtaaccaaa aagtgctcgg aagactggaa gcttgtgcga tctgcctcat    8400
tctccagagg aggacaattg agtttcactg atttgggctt accacctact gaccacctcc    8460
aggcctcatt tggatttcag acctttcaac ccagtggcat attattagat catcagacat    8520
ggacaaggaa cctgcaggtc actctggaag atggttacat tgaattgagc accagcgata    8580
gcggcagccc aattttttaaa tctccacaga cgtatatgga tggtttactg cattatgtat    8640
ctgtaataag cgacaactct ggactacggc ttctcatcga tgaccagctt ctgagaaata    8700
gcaaaaggct aaaacacatt tcaagttccc ggcagtctct gcgtctgggc gggagcaatt    8760
ttgagggttg tattagcaat gttttttgtcc agaggttatc actgagtcct gaagtcctag    8820
atttgaccag taactctctc aagagagatg tgtccctggg aggctgcagt ttaaacaaac    8880
caccttttct aatgttgctt aaaggttcta ccaggtttaa caagaccaag acttttcgta    8940
tcaaccagct gttgcaggac acaccagtgg cctccccaag gagcgtgaag gtgtggcaag    9000
atgcttgctc accacttccc aagacccagg ccaatcatgg agccctccag tttggggaca    9060
ttcccaccag ccacttgcta ttcaagcttc ctcaggagct gctgaaaccc aggtcacagt    9120
tgctgtggga catgcagaca acatcctcca gaggactggg gtttcacacg gcactaagaa    9180
actcctttat ggctctttat cttttcaaaag gacgtctggt cttttgcactg ggacagatg    9240
ggaaaaaatt gaggatcaaa agcaaggaga aatgcaatga tggaaatgg cacacggtgg    9300
tgtttggcca tgatggggaa aaggggcgct tggttgtgga tggactgagg gcccgggagg    9360
gaagtttgcc tggaaactcc accatcagca tcagagcgcc agtttacctg ggatcacctc    9420
catcagggaa accaaagagc ctccccacaa acagctttgt gggatgcctg aagaactttc    9480
agctggattc aaaaccccttg tataccccctt cttcaagctt cggggtgtct tcctgcttgg    9540
gtggtccttt ggagaaaggc atttatttct ctgaagaagg aggtcatgtc gtcttggctc    9600
actctgtatt gttggggcca gaatttaagc ttgttttcag catccgccca agaagtctca    9660
ctgggatcct aatacacatc ggaagtcagc ccgggaagca cttatgtgtt tacctggagg    9720
caggaaaggt cacggcctct atggacagtg gggcaggtgg gacctcaacg tcggtcacac    9780
caaagcagtc tctgtgtgat ggacagtggc actcggtggc agtcaccata aaacaacaca    9840
tcctgcacct ggaactggac acagacagta gctacacagc tggacagatc cccttcccac    9900
ctgccagcac tcaagagcca ctacaccttg gaggtgctcc agccaatttg acgacactga    9960
ggatccctgt gtggaaatca ttctttggct gtctgaggaa tattcatgtc aatcacatcc   10020
ctgtccctgt cactgaagcc ttggaagtcc aggggcctgt cagtctgaat ggttgtcctg   10080
accagtaacc caagcctatt tcacagcaag gaaattcacc ttcaaaagca ctgattaccc   10140
aatgcacctc cctccccagc tcgagatcat tcttcactca ggacacaaac cagacaggtt   10200
taatagcgaa tctaattttg aattctgacc atggatacccc atcactttgg cattcagtgc   10260
tacatgtgta ttttatataa aaatcccatt tcttgaagat aaaaaaattg ttattcaaat   10320
tgttatgcac agaatgtttt tggtaatatt aatttccact aaaaaattaa atgtcttta   10380
agaaacattc ttttccactt gttaaaaaaa ttaaatatat tttaaagcac tttaagaata   10440
tgaaactttc atatatgtta aaggattata atttatgaa ttaaaaaatg cagtgtagtc   10500
cttaaaaaa a                                                         10511
```

<210> SEQ ID NO 4
<211> LENGTH: 3333
<212> TYPE: PRT
<213> ORGANISM: Homo sapiens

<400> SEQUENCE: 4

```
Met Ala Ala Ala Arg Pro Arg Gly Arg Ala Leu Gly Pro Val Leu
 1               5                  10                  15

Pro Pro Thr Pro Leu Leu Leu Val Leu Arg Val Leu Pro Ala Cys
            20                  25                  30

Gly Ala Thr Ala Arg Asp Pro Gly Ala Ala Gly Leu Ser Leu His
            35                  40                  45

Pro Thr Tyr Phe Asn Leu Ala Glu Ala Ala Arg Ile Trp Ala Ala
 50                  55                  60

Thr Cys Gly Glu Arg Gly Pro Glu Gly Gly Arg Pro Gln Pro Glu Leu
 65                  70                  75                  80

Tyr Cys Lys Leu Val Gly Gly Pro Thr Ala Pro Gly Ser Gly His Thr
                    85                  90                  95

Ile Gln Gly Gln Phe Cys Asp Tyr Cys Asn Ser Glu Asp Pro Arg Lys
                    100                 105                 110

Ala His Pro Val Thr Asn Ala Ile Asp Gly Ser Glu Arg Trp Trp Gln
                    115                 120                 125

Ser Pro Pro Leu Ser Ser Gly Thr Gln Tyr Asn Arg Val Asn Leu Thr
            130                 135                 140

Leu Asp Leu Gly Gln Leu Phe His Val Ala Tyr Ile Leu Ile Lys Phe
145                 150                 155                 160

Ala Asn Ser Pro Arg Pro Asp Leu Trp Val Leu Glu Arg Ser Val Asp
                    165                 170                 175

Phe Gly Ser Thr Tyr Ser Pro Trp Gln Tyr Phe Ala His Ser Lys Val
                    180                 185                 190

Asp Cys Leu Lys Glu Phe Gly Arg Glu Ala Asn Met Ala Val Thr Arg
                    195                 200                 205

Asp Asp Asp Val Leu Cys Val Thr Glu Tyr Ser Arg Ile Val Pro Leu
            210                 215                 220

Glu Asn Gly Glu Val Val Val Ser Leu Ile Asn Gly Arg Pro Gly Ala
225                 230                 235                 240

Lys Asn Phe Thr Phe Ser His Thr Leu Arg Glu Phe Thr Lys Ala Thr
                    245                 250                 255

Asn Ile Arg Leu Arg Phe Leu Arg Thr Asn Thr Leu Leu Gly His Leu
                    260                 265                 270

Ile Ser Lys Ala Gln Arg Asp Pro Thr Val Thr Arg Arg Tyr Tyr Tyr
                    275                 280                 285

Ser Ile Lys Asp Ile Ser Ile Gly Gly Gln Cys Val Cys Asn Gly His
            290                 295                 300

Ala Glu Val Cys Asn Ile Asn Asn Pro Glu Lys Leu Phe Arg Cys Glu
305                 310                 315                 320

Cys Gln His His Thr Cys Gly Glu Thr Cys Asp Arg Cys Cys Thr Gly
                    325                 330                 335

Tyr Asn Gln Arg Arg Trp Arg Pro Ala Ala Trp Glu Gln Ser His Glu
                    340                 345                 350

Cys Glu Ala Cys Asn Cys His Gly His Ala Ser Asn Cys Tyr Tyr Asp
                    355                 360                 365

Pro Asp Val Glu Arg Gln Gln Ala Ser Leu Asn Thr Gln Gly Ile Tyr
            370                 375                 380
```

```
Ala Gly Gly Gly Val Cys Ile Asn Cys Gln His Asn Thr Ala Gly Val
385                 390                 395                 400

Asn Cys Glu Gln Cys Ala Lys Gly Tyr Tyr Arg Pro Tyr Gly Val Pro
            405                 410                 415

Val Asp Ala Pro Asp Gly Cys Ile Pro Cys Ser Cys Asp Pro Glu His
            420                 425                 430

Ala Asp Gly Cys Glu Gln Gly Ser Gly Arg Cys His Cys Lys Pro Asn
        435                 440                 445

Phe His Gly Asp Asn Cys Glu Lys Cys Ala Ile Gly Tyr Tyr Asn Phe
        450                 455                 460

Pro Phe Cys Leu Arg Ile Pro Ile Phe Pro Val Ser Thr Pro Ser Ser
465                 470                 475                 480

Glu Asp Pro Val Ala Gly Asp Ile Lys Gly Cys Asp Cys Asn Leu Glu
            485                 490                 495

Gly Val Leu Pro Glu Ile Cys Asp Ala His Gly Arg Cys Leu Cys Arg
            500                 505                 510

Pro Gly Val Glu Gly Pro Arg Cys Asp Thr Cys Arg Ser Gly Phe Tyr
        515                 520                 525

Ser Phe Pro Ile Cys Gln Ala Cys Trp Cys Ser Ala Leu Gly Ser Tyr
        530                 535                 540

Gln Met Pro Cys Ser Ser Val Thr Gly Gln Cys Glu Cys Arg Pro Gly
545                 550                 555                 560

Val Thr Gly Gln Arg Cys Asp Arg Cys Leu Ser Gly Ala Tyr Asp Phe
            565                 570                 575

Pro His Cys Gln Gly Ser Ser Ala Cys Asp Pro Ala Gly Thr Ile
            580                 585                 590

Asn Ser Asn Leu Gly Tyr Cys Gln Cys Lys Leu His Val Glu Gly Pro
        595                 600                 605

Thr Cys Ser Arg Cys Lys Leu Leu Tyr Trp Asn Leu Asp Lys Glu Asn
    610                 615                 620

Pro Ser Gly Cys Ser Glu Cys Lys Cys His Lys Ala Gly Thr Val Ser
625                 630                 635                 640

Gly Thr Gly Glu Cys Arg Gln Gly Asp Gly Asp Cys His Cys Lys Ser
            645                 650                 655

His Val Gly Gly Asp Ser Cys Asp Thr Cys Glu Asp Gly Tyr Phe Ala
            660                 665                 670

Leu Glu Lys Ser Asn Tyr Phe Gly Cys Gln Gly Cys Gln Cys Asp Ile
        675                 680                 685

Gly Gly Ala Leu Ser Ser Met Cys Ser Gly Pro Ser Gly Val Cys Gln
        690                 695                 700

Cys Arg Glu His Val Val Gly Lys Val Cys Gln Arg Pro Glu Asn Asn
705                 710                 715                 720

Tyr Tyr Phe Pro Asp Leu His His Met Lys Tyr Glu Ile Glu Asp Gly
            725                 730                 735

Ser Thr Pro Asn Gly Arg Asp Leu Arg Phe Gly Phe Asp Pro Leu Ala
            740                 745                 750

Phe Pro Glu Phe Ser Trp Arg Gly Tyr Ala Gln Met Thr Ser Val Gln
        755                 760                 765

Asn Asp Val Arg Ile Thr Leu Asn Val Gly Lys Ser Ser Gly Ser Leu
        770                 775                 780

Phe Arg Val Ile Leu Arg Tyr Val Asn Pro Gly Thr Glu Ala Val Ser
785                 790                 795                 800

Gly His Ile Thr Ile Tyr Pro Ser Trp Gly Ala Ala Gln Ser Lys Glu
```

```
                805                 810                 815
Ile Ile Phe Leu Pro Ser Lys Glu Pro Ala Phe Val Thr Val Pro Gly
            820                 825                 830
Asn Gly Phe Ala Asp Pro Phe Ser Ile Thr Pro Gly Ile Trp Val Ala
            835                 840                 845
Cys Ile Lys Ala Glu Gly Val Leu Leu Asp Tyr Leu Val Leu Leu Pro
            850                 855                 860
Arg Asp Tyr Tyr Glu Ala Ser Val Leu Gln Leu Pro Val Thr Glu Pro
865                 870                 875                 880
Cys Ala Tyr Ala Gly Pro Pro Gln Glu Asn Cys Leu Leu Tyr Gln His
            885                 890                 895
Leu Pro Val Thr Arg Phe Pro Cys Thr Leu Ala Cys Glu Ala Arg His
            900                 905                 910
Phe Leu Leu Asp Gly Glu Pro Arg Pro Val Ala Val Arg Gln Pro Thr
            915                 920                 925
Pro Ala His Pro Val Met Val Asp Leu Ser Gly Arg Glu Val Glu Leu
            930                 935                 940
His Leu Arg Leu Arg Ile Pro Gln Val Gly His Tyr Val Val Val Val
945                 950                 955                 960
Glu Tyr Ser Thr Glu Ala Ala Gln Leu Phe Val Asp Val Asn Val
            965                 970                 975
Lys Ser Ser Gly Ser Val Leu Ala Gly Gln Val Asn Ile Tyr Ser Cys
            980                 985                 990
Asn Tyr Ser Val Leu Cys Arg Ser Ala Val Ile Asp His Met Ser Arg
            995                 1000                1005
Ile Ala Met Tyr Glu Leu Leu Ala Asp Ala Asp Ile Gln Leu Lys Gly
            1010                1015                1020
His Met Ala Arg Phe Leu Leu His Gln Val Cys Ile Ile Pro Ile Glu
1025                1030                1035                1040
Glu Phe Ser Ala Glu Tyr Val Arg Pro Gln Val His Cys Ile Ala Ser
            1045                1050                1055
Tyr Gly Arg Phe Val Asn Gln Ser Ala Thr Cys Val Ser Leu Ala His
            1060                1065                1070
Glu Thr Pro Pro Thr Ala Leu Ile Leu Asp Val Leu Ser Gly Arg Pro
            1075                1080                1085
Phe Pro His Leu Pro Gln Gln Ser Ser Pro Ser Val Asp Val Leu Pro
            1090                1095                1100
Gly Val Thr Leu Lys Ala Pro Gln Asn Gln Val Thr Leu Arg Gly Arg
1105                1110                1115                1120
Val Pro His Leu Gly Arg Tyr Val Phe Val Ile His Phe Tyr Gln Ala
            1125                1130                1135
Ala His Pro Thr Phe Pro Ala Gln Val Ser Val Asp Gly Gly Trp Pro
            1140                1145                1150
Arg Ala Gly Ser Phe His Ala Ser Phe Cys Pro His Val Leu Gly Cys
            1155                1160                1165
Arg Asp Gln Val Ile Ala Glu Gly Gln Ile Glu Phe Asp Ile Ser Glu
            1170                1175                1180
Pro Glu Val Ala Ala Thr Val Lys Val Pro Glu Gly Lys Ser Leu Val
1185                1190                1195                1200
Leu Val Arg Val Leu Val Val Pro Ala Glu Asn Tyr Asp Tyr Gln Ile
            1205                1210                1215
Leu His Lys Lys Ser Met Asp Lys Ser Leu Glu Phe Ile Thr Asn Cys
            1220                1225                1230
```

```
Gly Lys Asn Ser Phe Tyr Leu Asp Pro Gln Thr Ala Ser Arg Phe Cys
        1235                1240                1245

Lys Asn Ser Ala Arg Ser Leu Val Ala Phe Tyr His Lys Gly Ala Leu
    1250                1255                1260

Pro Cys Glu Cys His Pro Thr Gly Ala Thr Gly Pro His Cys Ser Pro
1265                1270                1275                1280

Glu Gly Gly Gln Cys Pro Cys Gln Pro Asn Val Ile Gly Arg Gln Cys
            1285                1290                1295

Thr Arg Cys Ala Thr Gly His Tyr Gly Phe Pro Arg Cys Lys Pro Cys
                1300                1305                1310

Ser Cys Gly Arg Arg Leu Cys Glu Glu Met Thr Gly Gln Cys Arg Cys
            1315                1320                1325

Pro Pro Arg Thr Val Arg Pro Gln Cys Glu Val Cys Glu Thr His Ser
        1330                1335                1340

Phe Ser Phe His Pro Met Ala Gly Cys Glu Gly Cys Asn Cys Ser Arg
1345                1350                1355                1360

Arg Gly Thr Ile Glu Ala Ala Met Pro Glu Cys Asp Arg Asp Ser Gly
            1365                1370                1375

Gln Cys Arg Cys Lys Pro Arg Ile Thr Gly Arg Gln Cys Asp Arg Cys
                1380                1385                1390

Ala Ser Gly Phe Tyr Arg Phe Pro Glu Cys Val Pro Cys Asn Cys Asn
            1395                1400                1405

Arg Asp Gly Thr Glu Pro Gly Val Cys Asp Pro Gly Thr Gly Ala Cys
        1410                1415                1420

Leu Cys Lys Glu Asn Val Glu Gly Thr Glu Cys Asn Val Cys Arg Glu
1425                1430                1435                1440

Gly Ser Phe His Leu Asp Pro Ala Asn Leu Lys Gly Cys Thr Ser Cys
            1445                1450                1455

Phe Cys Phe Gly Val Asn Asn Gln Cys His Ser Ser His Lys Arg Arg
            1460                1465                1470

Thr Lys Phe Val Asp Met Leu Gly Trp His Leu Glu Thr Ala Asp Arg
            1475                1480                1485

Val Asp Ile Pro Val Ser Phe Asn Pro Gly Ser Asn Ser Met Val Ala
        1490                1495                1500

Asp Leu Gln Glu Leu Pro Ala Thr Ile His Ser Ala Ser Trp Val Ala
1505                1510                1515                1520

Pro Thr Ser Tyr Leu Gly Asp Lys Val Ser Ser Tyr Gly Gly Tyr Leu
            1525                1530                1535

Thr Tyr Gln Ala Lys Ser Phe Gly Leu Pro Gly Asp Met Val Leu Leu
            1540                1545                1550

Glu Lys Lys Pro Asp Val Gln Leu Thr Gly Gln His Met Ser Ile Ile
        1555                1560                1565

Tyr Glu Glu Thr Asn Thr Pro Arg Pro Asp Arg Leu His His Gly Arg
    1570                1575                1580

Val His Val Val Glu Gly Asn Phe Arg His Ala Ser Ser Arg Ala Pro
1585                1590                1595                1600

Val Ser Arg Glu Glu Leu Met Thr Val Leu Ser Arg Leu Ala Asp Val
            1605                1610                1615

Arg Ile Gln Gly Leu Tyr Phe Thr Glu Thr Gln Arg Leu Thr Leu Ser
        1620                1625                1630

Glu Val Gly Leu Glu Glu Ala Ser Asp Thr Gly Ser Gly Arg Ile Ala
        1635                1640                1645
```

-continued

```
Leu Ala Val Glu Ile Cys Ala Cys Pro Pro Ala Tyr Ala Gly Asp Ser
    1650                1655                1660

Cys Gln Gly Cys Ser Pro Gly Tyr Tyr Arg Asp His Lys Gly Leu Tyr
1665                1670                1675                1680

Thr Gly Arg Cys Val Pro Cys Asn Cys Asn Gly His Ser Asn Gln Cys
                1685                1690                1695

Gln Asp Gly Ser Gly Ile Cys Val Asn Cys Gln His Asn Thr Ala Gly
            1700                1705                1710

Glu His Cys Glu Arg Cys Gln Glu Gly Tyr Tyr Gly Asn Ala Val His
        1715                1720                1725

Gly Ser Cys Arg Ala Cys Pro Cys His Thr Asn Ser Phe Ala Thr
    1730                1735                1740

Gly Cys Val Val Asn Gly Gly Asp Val Arg Cys Ser Cys Lys Ala Gly
1745                1750                1755                1760

Tyr Thr Gly Thr Gln Cys Glu Arg Cys Ala Pro Gly Tyr Phe Gly Asn
                1765                1770                1775

Pro Gln Lys Phe Gly Gly Ser Cys Gln Pro Cys Ser Cys Asn Ser Asn
            1780                1785                1790

Gly Gln Leu Gly Ser Cys His Pro Leu Thr Gly Asp Cys Ile Asn Gln
        1795                1800                1805

Glu Pro Lys Asp Ser Ser Pro Ala Glu Glu Cys Asp Asp Cys Asp Ser
    1810                1815                1820

Cys Val Met Thr Leu Leu Asn Asp Leu Ala Thr Met Gly Glu Gln Leu
1825                1830                1835                1840

Arg Leu Val Lys Ser Gln Leu Gln Gly Leu Ser Ala Ser Ala Gly Leu
                1845                1850                1855

Leu Glu Gln Met Arg His Met Glu Thr Gln Ala Lys Asp Leu Arg Asn
            1860                1865                1870

Gln Leu Leu Asn Tyr Arg Ser Ala Ile Ser Asn His Gly Ser Lys Ile
        1875                1880                1885

Glu Gly Leu Glu Arg Glu Leu Thr Asp Leu Asn Gln Glu Phe Glu Thr
    1890                1895                1900

Leu Gln Glu Lys Ala Gln Val Asn Ser Arg Lys Ala Gln Thr Leu Asn
1905                1910                1915                1920

Asn Asn Val Asn Arg Ala Thr Gln Ser Ala Lys Glu Leu Asp Val Lys
                1925                1930                1935

Ile Lys Asn Val Ile Arg Asn Val His Ile Leu Leu Lys Gln Ile Ser
            1940                1945                1950

Gly Thr Asp Gly Glu Gly Asn Asn Val Pro Ser Gly Asp Phe Ser Arg
        1955                1960                1965

Glu Trp Ala Glu Ala Gln Arg Met Met Arg Glu Leu Arg Asn Arg Asn
    1970                1975                1980

Phe Gly Lys His Leu Arg Glu Ala Glu Ala Asp Lys Arg Glu Ser Gln
1985                1990                1995                2000

Leu Leu Leu Asn Arg Ile Arg Thr Trp Gln Lys Thr His Gln Gly Glu
                2005                2010                2015

Asn Asn Gly Leu Ala Asn Ser Ile Arg Asp Ser Leu Asn Glu Tyr Glu
            2020                2025                2030

Ala Lys Leu Ser Asp Leu Arg Ala Arg Leu Gln Glu Ala Ala Ala Gln
        2035                2040                2045

Ala Lys Gln Ala Asn Gly Leu Asn Gln Glu Asn Glu Arg Ala Leu Gly
    2050                2055                2060

Ala Ile Gln Arg Gln Val Lys Glu Ile Asn Ser Leu Gln Ser Asp Phe
```

```
                2065                2070                2075                2080
Thr Lys Tyr Leu Thr Thr Ala Asp Ser Ser Leu Leu Gln Thr Asn Ile
                2085                2090                2095

Ala Leu Gln Leu Met Glu Lys Ser Gln Lys Glu Tyr Glu Lys Leu Ala
            2100                2105                2110

Ala Ser Leu Asn Glu Ala Arg Gln Glu Leu Ser Asp Lys Val Arg Glu
            2115                2120                2125

Leu Ser Arg Ser Ala Gly Lys Thr Ser Leu Val Glu Glu Ala Glu Lys
            2130                2135                2140

His Ala Arg Ser Leu Gln Glu Leu Ala Lys Gln Leu Glu Glu Ile Lys
2145                2150                2155                2160

Arg Asn Ala Ser Gly Asp Glu Leu Val Arg Cys Ala Val Asp Ala Ala
                2165                2170                2175

Thr Ala Tyr Glu Asn Ile Leu Asn Ala Ile Lys Ala Ala Glu Asp Ala
            2180                2185                2190

Ala Asn Arg Ala Ala Ser Ala Ser Glu Ser Ala Leu Gln Thr Val Ile
            2195                2200                2205

Lys Glu Asp Leu Pro Arg Lys Ala Lys Thr Leu Ser Ser Asn Ser Asp
            2210                2215                2220

Lys Leu Leu Asn Glu Ala Lys Met Thr Gln Lys Lys Leu Lys Gln Glu
2225                2230                2235                2240

Val Ser Pro Ala Leu Asn Asn Leu Gln Gln Thr Leu Asn Ile Val Thr
                2245                2250                2255

Val Gln Lys Glu Val Ile Asp Thr Asn Leu Thr Thr Leu Arg Asp Gly
            2260                2265                2270

Leu His Gly Ile Gln Arg Gly Asp Ile Asp Ala Met Ile Ser Ser Ala
            2275                2280                2285

Lys Ser Met Val Arg Lys Ala Asn Asp Ile Thr Asp Glu Val Leu Asp
            2290                2295                2300

Gly Leu Asn Pro Ile Gln Thr Asp Val Glu Arg Ile Lys Asp Thr Tyr
2305                2310                2315                2320

Gly Arg Thr Gln Asn Glu Asp Phe Lys Lys Ala Leu Thr Asp Ala Asp
                2325                2330                2335

Asn Ser Val Asn Lys Leu Thr Asn Lys Leu Pro Asp Leu Trp Arg Lys
            2340                2345                2350

Ile Glu Ser Ile Asn Gln Gln Leu Leu Pro Leu Gly Asn Ile Ser Asp
            2355                2360                2365

Asn Met Asp Arg Ile Arg Glu Leu Ile Gln Gln Ala Arg Asp Ala Ala
            2370                2375                2380

Ser Lys Val Ala Val Pro Met Arg Phe Asn Gly Lys Ser Gly Val Glu
2385                2390                2395                2400

Val Arg Leu Pro Asn Asp Leu Glu Asp Leu Lys Gly Tyr Thr Ser Leu
                2405                2410                2415

Ser Leu Phe Leu Gln Arg Pro Asn Ser Arg Glu Asn Gly Gly Thr Glu
            2420                2425                2430

Asn Met Phe Val Met Tyr Leu Gly Asn Lys Asp Ala Ser Arg Asp Tyr
            2435                2440                2445

Ile Gly Met Ala Val Val Asp Gly Gln Leu Thr Cys Val Tyr Asn Leu
            2450                2455                2460

Gly Asp Arg Glu Ala Glu Leu Gln Val Asp Gln Ile Leu Thr Lys Ser
2465                2470                2475                2480

Glu Thr Lys Glu Ala Val Met Asp Arg Val Lys Phe Gln Arg Ile Tyr
                2485                2490                2495
```

```
Gln Phe Ala Arg Leu Asn Tyr Thr Lys Gly Ala Thr Ser Ser Lys Pro
            2500                2505                2510

Glu Thr Pro Gly Val Tyr Asp Met Asp Gly Arg Asn Ser Asn Thr Leu
        2515                2520                2525

Leu Asn Leu Asp Pro Glu Asn Val Val Phe Tyr Val Gly Gly Tyr Pro
        2530                2535                2540

Pro Asp Phe Lys Leu Pro Ser Arg Leu Ser Phe Pro Pro Tyr Lys Gly
2545                2550                2555                2560

Cys Ile Glu Leu Asp Asp Leu Asn Glu Asn Val Leu Ser Leu Tyr Asn
            2565                2570                2575

Phe Lys Lys Thr Phe Asn Leu Asn Thr Thr Glu Val Glu Pro Cys Arg
        2580                2585                2590

Arg Arg Lys Glu Glu Ser Asp Lys Asn Tyr Phe Glu Gly Thr Gly Tyr
        2595                2600                2605

Ala Arg Val Pro Thr Gln Pro His Ala Pro Ile Pro Thr Phe Gly Gln
        2610                2615                2620

Thr Ile Gln Thr Thr Val Asp Arg Gly Leu Leu Phe Phe Ala Glu Asn
2625                2630                2635                2640

Gly Asp Arg Phe Ile Ser Leu Asn Ile Glu Asp Gly Lys Leu Met Val
            2645                2650                2655

Arg Tyr Lys Leu Asn Ser Glu Leu Pro Lys Glu Arg Gly Val Gly Asp
        2660                2665                2670

Ala Ile Asn Asn Gly Arg Asp His Ser Ile Gln Ile Lys Ile Gly Lys
        2675                2680                2685

Leu Gln Lys Arg Met Trp Ile Asn Val Asp Val Gln Asn Thr Ile Ile
        2690                2695                2700

Asp Gly Glu Val Phe Asp Phe Ser Thr Tyr Tyr Leu Gly Gly Ile Pro
2705                2710                2715                2720

Ile Ala Ile Arg Glu Arg Phe Asn Ile Ser Thr Pro Ala Phe Arg Gly
            2725                2730                2735

Cys Met Lys Asn Leu Lys Lys Thr Ser Gly Val Val Arg Leu Asn Asp
        2740                2745                2750

Thr Val Gly Val Thr Lys Lys Cys Ser Glu Asp Trp Lys Leu Val Arg
        2755                2760                2765

Ser Ala Ser Phe Ser Arg Gly Gly Gln Leu Ser Phe Thr Asp Leu Gly
        2770                2775                2780

Leu Pro Pro Thr Asp His Leu Gln Ala Ser Phe Gly Phe Gln Thr Phe
2785                2790                2795                2800

Gln Pro Ser Gly Ile Leu Leu Asp His Gln Thr Trp Thr Arg Asn Leu
            2805                2810                2815

Gln Val Thr Leu Glu Asp Gly Tyr Ile Glu Leu Ser Thr Ser Asp Ser
        2820                2825                2830

Gly Ser Pro Ile Phe Lys Ser Pro Gln Thr Tyr Met Asp Gly Leu Leu
        2835                2840                2845

His Tyr Val Ser Val Ile Ser Asp Asn Ser Gly Leu Arg Leu Leu Ile
        2850                2855                2860

Asp Asp Gln Leu Leu Arg Asn Ser Lys Arg Leu Lys His Ile Ser Ser
2865                2870                2875                2880

Ser Arg Gln Ser Leu Arg Leu Gly Gly Ser Asn Phe Glu Gly Cys Ile
            2885                2890                2895

Ser Asn Val Phe Val Gln Arg Leu Ser Leu Ser Pro Glu Val Leu Asp
        2900                2905                2910
```

-continued

```
Leu Thr Ser Asn Ser Leu Lys Arg Asp Val Ser Leu Gly Gly Cys Ser
         2915                2920                2925

Leu Asn Lys Pro Pro Phe Leu Met Leu Leu Lys Gly Ser Thr Arg Phe
         2930                2935            2940

Asn Lys Thr Lys Thr Phe Arg Ile Asn Gln Leu Leu Gln Asp Thr Pro
2945                2950                2955                2960

Val Ala Ser Pro Arg Ser Val Lys Val Trp Gln Asp Ala Cys Ser Pro
             2965                2970                2975

Leu Pro Lys Thr Gln Ala Asn His Gly Ala Leu Gln Phe Gly Asp Ile
             2980                2985                2990

Pro Thr Ser His Leu Leu Phe Lys Leu Pro Gln Glu Leu Leu Lys Pro
             2995                3000                3005

Arg Ser Gln Phe Ala Val Asp Met Gln Thr Thr Ser Ser Arg Gly Leu
         3010                3015                3020

Val Phe His Thr Gly Thr Lys Asn Ser Phe Met Ala Leu Tyr Leu Ser
3025                3030                3035                3040

Lys Gly Arg Leu Val Phe Ala Leu Gly Thr Asp Gly Lys Lys Leu Arg
             3045                3050                3055

Ile Lys Ser Lys Glu Lys Cys Asn Asp Gly Lys Trp His Thr Val Val
             3060                3065                3070

Phe Gly His Asp Gly Glu Lys Gly Arg Leu Val Val Asp Gly Leu Arg
         3075                3080                3085

Ala Arg Glu Gly Ser Leu Pro Gly Asn Ser Thr Ile Ser Ile Arg Ala
         3090                3095                3100

Pro Val Tyr Leu Gly Ser Pro Pro Ser Gly Lys Pro Lys Ser Leu Pro
3105                3110                3115                3120

Thr Asn Ser Phe Val Gly Cys Leu Lys Asn Phe Gln Leu Asp Ser Lys
             3125                3130                3135

Pro Leu Tyr Thr Pro Ser Ser Ser Phe Gly Val Ser Ser Cys Leu Gly
             3140                3145                3150

Gly Pro Leu Glu Lys Gly Ile Tyr Phe Ser Glu Glu Gly Gly His Val
             3155                3160                3165

Val Leu Ala His Ser Val Leu Leu Gly Pro Glu Phe Lys Leu Val Phe
         3170                3175                3180

Ser Ile Arg Pro Arg Ser Leu Thr Gly Ile Leu Ile His Ile Gly Ser
3185                3190                3195                3200

Gln Pro Gly Lys His Leu Cys Val Tyr Leu Glu Ala Gly Lys Val Thr
             3205                3210                3215

Ala Ser Met Asp Ser Gly Ala Gly Gly Thr Ser Thr Ser Val Thr Pro
             3220                3225                3230

Lys Gln Ser Leu Cys Asp Gly Gln Trp His Ser Val Ala Val Thr Ile
             3235                3240                3245

Lys Gln His Ile Leu His Leu Glu Leu Asp Thr Asp Ser Ser Tyr Thr
             3250                3255                3260

Ala Gly Gln Ile Pro Phe Pro Pro Ala Ser Thr Gln Glu Pro Leu His
             3265                3270                3275                3280

Leu Gly Gly Ala Pro Ala Asn Leu Thr Thr Leu Arg Ile Pro Val Trp
             3285                3290                3295

Lys Ser Phe Phe Gly Cys Leu Arg Asn Ile His Val Asn His Ile Pro
             3300                3305                3310

Val Pro Val Thr Glu Ala Leu Glu Val Gln Gly Pro Val Ser Leu Asn
             3315                3320                3325

Gly Cys Pro Asp Gln
```

-continued

3330

<210> SEQ ID NO 5
<211> LENGTH: 5601
<212> TYPE: DNA
<213> ORGANISM: Homo sapiens

<400> SEQUENCE: 5

| | | | | | |
|---|---|---|---|---|---|
| gggatgcctc | cagcagtgag | gcggtcagcc | tgcagcatgg | gatggctgtg | gatctttggg | 60 |
| gcagccctgg | ggcagtgtct | gggctacagt | tcacagcagc | aaagggtgcc | atttcttcag | 120 |
| cctcccggtc | aaagtcaact | gcaagcgagt | tatgtggagt | ttagacccag | ccagggttgt | 180 |
| agccctggat | actatcggga | tcataaaggc | ttgtataccg | gacggtgtgt | tccctgcaat | 240 |
| tgcaacggac | attcaaatca | atgccaggat | ggctcaggca | tatgtgttaa | ctgtcagcac | 300 |
| aacaccgcgg | gagagcactg | tgaacgctgc | caggagggct | actatggcaa | cgccgtccac | 360 |
| ggatcctgca | gggcctgccc | atgtcctcac | actaacagct | tgccactggg | ctgtgtggtg | 420 |
| aatgggggag | acgtgcggtg | ctcctgcaaa | gctgggtaca | caggaacaca | gtgtgaaagg | 480 |
| tgtgcaccgg | atatttcgg | gaatcccag | aaattcggag | gtagctgcca | accatgcagt | 540 |
| tgtaacagca | atggccagct | gggcagctgt | catccctga | ctggagactg | cataaaccaa | 600 |
| gaacccaaag | atagcagccc | tgcagaagaa | tgtgatgatt | cgacagctg | tgtgatgacc | 660 |
| ctcctgaacg | acctggccac | catgggcgag | cagctccgcc | tggtcaagtc | tcagctgcag | 720 |
| ggcctgagtg | ccagcgcagg | gcttctggag | cagatgaggc | acatggagac | ccaggccaag | 780 |
| gacctgagga | atcagttgct | caactaccgt | tctgccattt | caaatcatgg | atcaaaaata | 840 |
| gaaggcctgg | aaagagaact | gactgatttg | aatcaagaat | ttgagacttt | gcaagaaaag | 900 |
| gctcaagtaa | attccagaaa | agcacaaaca | ttaaacaaca | atgttaatcg | ggcaacacaa | 960 |
| agcgcaaaag | aactggatgt | gaagattaaa | aatgtcatcc | ggaatgtgca | cattcttta | 1020 |
| aagcagatct | ctgggacaga | tggagaggga | acaacgtgc | cttcaggtga | cttttccaga | 1080 |
| gagtgggctg | aagcccagcg | catgatgagg | gaactgcgga | caggaacttt | tggaaagcac | 1140 |
| ctcagagaag | cagaagctga | taaaagggag | tcgcagctct | tgctgaaccg | gataaggacc | 1200 |
| tggcagaaaa | cccaccaggg | ggagaacaat | gggcttgcta | acagtatccg | ggattcttta | 1260 |
| aatgaatacg | aagccaaact | cagtgacctt | cgtgctcggc | tgcaggaggc | agctgcccaa | 1320 |
| gccaagcagg | caaatggctt | gaaccaagaa | aacgagagag | ctttgggagc | cattcagaga | 1380 |
| caagtgaaag | aaataaattc | cctgcagagt | gatttcacca | agtatctaac | cactgcagac | 1440 |
| tcatctttgt | tgcaaaccaa | cattgcgctg | cagctgatgg | agaaaagcca | gaaggaatat | 1500 |
| gaaaaattag | ctgccagttt | aaatgaagca | agacaagaac | taagtgacaa | agtaagagaa | 1560 |
| ctttccagat | ctgctggcaa | acatcccctt | gtggaggagg | cagaaaagca | cgcgcggtcc | 1620 |
| ttacaagagc | tggcaaagca | gctggaagag | atcaagaaa | acgccagcgg | ggatgagctg | 1680 |
| gtgcgctgtg | ctgtggatgc | cgccaccgcc | tacgagaaca | tcctcaatgc | catcaaagcg | 1740 |
| gccgaggacg | cagccaacag | ggctgccagt | gcatctgaat | ctgccctcca | gacagtgata | 1800 |
| aaggaagatc | tgccaagaaa | agctaaaacc | ctgagttcca | acagtgataa | actgttaaat | 1860 |
| gaagccaaga | tgcacaaaaa | gaagctaaag | caagaagtca | gtccagctct | caacaaccta | 1920 |
| cagcaaaccc | tgaatattgt | gacagttcag | aaagaagtga | tagacaccaa | tctcacaact | 1980 |
| ctccgagatg | gtcttcatgg | gatacagaga | ggtgatattg | atgctatgat | cagtagtgca | 2040 |
| aagagcatgg | tcagaaaggc | caacgacatc | acagatgagg | ttctggatgg | gctcaaccc | 2100 |

```
atccagacag atgtggaaag aattaaggac acctatggga ggacacagaa cgaagacttc   2160
aaaaaggctc tgactgatgc agataactcg gtgaataagt taaccaacaa actacctgat   2220
ctttggcgca agattgaaag tatcaaccaa cagctgttgc ccttgggaaa catctctgac   2280
aacatggaca gaatacgaga actaattcag caggccagag atgctgccag taaggttgct   2340
gtccccatga ggttcaatgg taaatctgga gtcgaagtcc gactgccaaa tgacctggaa   2400
gatttgaaag gatatacatc tctgtccttg tttctccaaa ggcccaactc aagagaaaat   2460
gggggtactg agaatatgtt tgtgatgtac cttggaaata agatgcctc ccgggactac   2520 atcggcatgg cagttgtgga tggccagctc acctgtgtct acaacctggg ggaccgtgag   2580
gctgaactcc aagtggacca gatcttgacc aagagtgaga ctaaggaggc agttatggat   2640
cgggtgaaat tcagagaat ttatcagttt gcaaggctta attacaccaa aggagccaca   2700
tccagtaaac cagaaacacc cggagtctat gacatggatg gtagaaatag caatacactc   2760
cttaatttgg atcctgaaaa tgttgtattt tatgttggag gttacccacc tgattttaaa   2820
cttcccagtc gactaagttt ccctccatac aaaggttgta ttgaattaga tgacctcaat   2880
gaaaatgttc tgagcttgta caacttcaaa aaaacattca atctcaacac aactgaagtg   2940
gagccttgta aaggaggaa ggaagagtca gacaaaaatt attttgaagg tacgggctat   3000
gctcgagttc caactcaacc acatgctccc atcccaacct ttggacagac aattcagacc   3060
accgtggata gaggcttgct gttctttgca gaaaacgggg atcgcttcat atctctaaat   3120
atagaagatg gcaagctcat ggtgagatac aaactgaatt cagagctacc aaaagagaga   3180
ggagttggag acgccataaa caacggcaga gaccattcga ttcagatcaa aattggaaaa   3240
ctccaaaagc gtatgtggat aaatgtggac gttcaaaaca ctataattga tggtgaagta   3300
tttgatttca gcacatatta tctgggagga attccaattg caatcaggga aagatttaac   3360
atttctacgc ctgctttccg aggctgcatg aaaaatttga agaaaaccag tggtgtcgtt   3420
agattgaatg atactgtggg agtaaccaaa aagtgctcgg aagactggaa gcttgtgcga   3480
tctgcctcat tctccagagg aggacaattg agtttcactg atttgggctt accacctact   3540
gaccacctcc aggcctcatt tggatttcag acctttcaac ccagtggcat attattagat   3600
catcagacat ggacaaggaa cctgcaggtc actctggaag atggttacat tgaattgagc   3660
accagcgata gcggcagccc aatttttaaa tctccacaga cgtatatgga tggtttactg   3720
cattatgtat ctgtaataag cgacaactct ggactacggc ttctcatcga tgaccagctt   3780
ctgagaaata gcaaaaggct aaaacacatt tcaagttccc ggcagtctct gcgtctgggc   3840
gggagcaatt ttgagggttg tattagcaat gttttttgtcc agaggttatc actgagtcct   3900
gaagtcctag atttgaccag taactctctc aagagagatg tgtccctggg aggctgcagt   3960
ttaaacaaac cacctttct aatgttgctt aaaggttcta ccaggtttaa caagaccaag   4020
acttttcgta tcaaccagct gttgcaggac acaccagtgg cctccccaag gagcgtgaag   4080
gtgtggcaag atgcttgctc accacttccc aagacccagg ccaatcatgg agccctccag   4140
tttggggaca ttcccaccag ccacttgcta ttcaagcttc ctcaggagct gctgaaaccc   4200
aggtcacagt ttgctgtgga catgcagaca acatcctcca gaggactggt gtttcacacg   4260
ggcactaaga actcctttat ggctctttat cttttcaaaag gacgtctggt ctttgcactg   4320
gggacagatg ggaaaaaatt gaggatcaaa agcaaggaga aatgcaatga tgggaaatgg   4380
cacacggtgg tgtttggcca tgatgggaa aaggggcgct tggttgtgga tggactgagg   4440
```

-continued

```
gcccgggagg gaagttttgcc tggaaactcc accatcagca tcagagcgcc agtttacctg    4500
ggatcacctc catcagggaa accaaagagc ctccccacaa acagctttgt gggatgcctg    4560
aagaactttc agctggattc aaaacccttg tataccccctt cttcaagctt cggggtgtct    4620
tcctgcttgg gtggtccttt ggagaaaggc atttatttct ctgaagaagg aggtcatgtc    4680
gtcttggctc actctgtatt gttggggcca gaatttaagc ttgttttcag catccgccca    4740
agaagtctca ctgggatcct aatacacatc ggaagtcagc ccgggaagca cttatgtgtt    4800
tacctggagg caggaaaggt cacggcctct atggacagtg gggcaggtgg gacctcaacg    4860
tcggtcacac caaagcagtc tctgtgtgat ggacagtggc actcggtggc agtcaccata    4920
aaacaacaca tcctgcacct ggaactggac acagacagta gctacacagc tggacagatc    4980
cccttcccac ctgccagcac tcaagagcca ctacaccttg gaggtgctcc agccaatttg    5040
acgacactga ggatccctgt gtggaaatca ttctttggct gtctgaggaa tattcatgtc    5100
aatcacatcc ctgtccctgt cactgaagcc ttggaagtcc aggggcctgt cagtctgaat    5160
ggttgtcctg accagtaacc caagcctatt tcacagcaag gaaattcacc ttcaaaagca    5220
ctgattaccc aatgcacctc cctcccccagc tcgagatcat tcttcactca ggacacaaac    5280
cagacaggtt taatagcgaa tctaattttg aattctgacc atggataccc atcactttgg    5340
cattcagtgc tacatgtgta ttttatataa aaatcccatt tcttgaagat aaaaaaattg    5400
ttattcaaat tgttatgcac agaatgtttt tggtaatatt aatttccact aaaaaattaa    5460
atgtctttta agaacattc ttttccactt gttaaaaaaa ttaaatatat tttaaagcac    5520
tttaagaata tgaaactttc atatatgtta aaggattata atttatggaa ttaaaaaatg    5580
cagtgtagtc cttaaaaaaa a                                              5601
```

<210> SEQ ID NO 6
<211> LENGTH: 1724
<212> TYPE: PRT
<213> ORGANISM: Homo sapiens

<400> SEQUENCE: 6

```
Met Pro Pro Ala Val Arg Arg Ser Ala Cys Ser Met Gly Trp Leu Trp
1               5                   10                  15

Ile Phe Gly Ala Ala Leu Gly Gln Cys Leu Gly Tyr Ser Ser Gln Gln
            20                  25                  30

Gln Arg Val Pro Phe Leu Gln Pro Gly Gln Ser Gln Leu Gln Ala
        35                  40                  45

Ser Tyr Val Glu Phe Arg Pro Ser Gln Gly Cys Ser Pro Gly Tyr Tyr
    50                  55                  60

Arg Asp His Lys Gly Leu Tyr Thr Gly Arg Cys Val Pro Cys Asn Cys
65                  70                  75                  80

Asn Gly His Ser Asn Gln Cys Gln Asp Gly Ser Gly Ile Cys Val Asn
                85                  90                  95

Cys Gln His Asn Thr Ala Gly Glu His Cys Glu Arg Cys Gln Glu Gly
            100                 105                 110

Tyr Tyr Gly Asn Ala Val His Gly Ser Cys Arg Ala Cys Pro Cys Pro
        115                 120                 125

His Thr Asn Ser Phe Ala Thr Gly Cys Val Val Asn Gly Gly Asp Val
    130                 135                 140

Arg Cys Ser Cys Lys Ala Gly Tyr Thr Gly Thr Gln Cys Glu Arg Cys
145                 150                 155                 160

Ala Pro Gly Tyr Phe Gly Asn Pro Gln Lys Phe Gly Gly Ser Cys Gln
```

-continued

```
                165                 170                 175
Pro Cys Ser Cys Asn Ser Asn Gly Gln Leu Gly Ser Cys His Pro Leu
            180                 185                 190
Thr Gly Asp Cys Ile Asn Gln Glu Pro Lys Asp Ser Ser Pro Ala Glu
            195                 200                 205
Glu Cys Asp Asp Cys Asp Ser Cys Val Met Thr Leu Leu Asn Asp Leu
            210                 215                 220
Ala Thr Met Gly Glu Gln Leu Arg Leu Val Lys Ser Gln Leu Gln Gly
225                 230                 235                 240
Leu Ser Ala Ser Ala Gly Leu Leu Glu Gln Met Arg His Met Glu Thr
                245                 250                 255
Gln Ala Lys Asp Leu Arg Asn Gln Leu Leu Asn Tyr Arg Ser Ala Ile
            260                 265                 270
Ser Asn His Gly Ser Lys Ile Glu Gly Leu Glu Arg Glu Leu Thr Asp
            275                 280                 285
Leu Asn Gln Glu Phe Glu Thr Leu Gln Glu Lys Ala Gln Val Asn Ser
            290                 295                 300
Arg Lys Ala Gln Thr Leu Asn Asn Asn Val Asn Arg Ala Thr Gln Ser
305                 310                 315                 320
Ala Lys Glu Leu Asp Val Lys Ile Lys Asn Val Ile Arg Asn Val His
                325                 330                 335
Ile Leu Leu Lys Gln Ile Ser Gly Thr Asp Gly Glu Gly Asn Asn Val
            340                 345                 350
Pro Ser Gly Asp Phe Ser Arg Glu Trp Ala Glu Ala Gln Arg Met Met
            355                 360                 365
Arg Glu Leu Arg Asn Arg Asn Phe Gly Lys His Leu Arg Glu Ala Glu
            370                 375                 380
Ala Asp Lys Arg Glu Ser Gln Leu Leu Leu Asn Arg Ile Arg Thr Trp
385                 390                 395                 400
Gln Lys Thr His Gln Gly Glu Asn Asn Gly Leu Ala Asn Ser Ile Arg
                405                 410                 415
Asp Ser Leu Asn Glu Tyr Glu Ala Lys Leu Ser Asp Leu Arg Ala Arg
            420                 425                 430
Leu Gln Glu Ala Ala Gln Ala Lys Gln Ala Asn Gly Leu Asn Gln
            435                 440                 445
Glu Asn Glu Arg Ala Leu Gly Ala Ile Gln Arg Gln Val Lys Glu Ile
            450                 455                 460
Asn Ser Leu Gln Ser Asp Phe Thr Lys Tyr Leu Thr Thr Ala Asp Ser
465                 470                 475                 480
Ser Leu Leu Gln Thr Asn Ile Ala Leu Gln Leu Met Glu Lys Ser Gln
                485                 490                 495
Lys Glu Tyr Glu Lys Leu Ala Ala Ser Leu Asn Glu Ala Arg Gln Glu
            500                 505                 510
Leu Ser Asp Lys Val Arg Glu Leu Ser Arg Ser Ala Gly Lys Thr Ser
            515                 520                 525
Leu Val Glu Glu Ala Glu Lys His Ala Arg Ser Leu Gln Glu Leu Ala
            530                 535                 540
Lys Gln Leu Glu Glu Ile Lys Arg Asn Ala Ser Gly Asp Glu Leu Val
545                 550                 555                 560
Arg Cys Ala Val Asp Ala Ala Thr Ala Tyr Glu Asn Ile Leu Asn Ala
                565                 570                 575
Ile Lys Ala Ala Glu Asp Ala Ala Asn Arg Ala Ala Ser Ala Ser Glu
            580                 585                 590
```

-continued

```
Ser Ala Leu Gln Thr Val Ile Lys Glu Asp Leu Pro Arg Lys Ala Lys
            595                 600                 605

Thr Leu Ser Ser Asn Ser Asp Lys Leu Leu Asn Glu Ala Lys Met Thr
        610                 615                 620

Gln Lys Lys Leu Lys Gln Glu Val Ser Pro Ala Leu Asn Asn Leu Gln
625                 630                 635                 640

Gln Thr Leu Asn Ile Val Thr Val Gln Lys Glu Val Ile Asp Thr Asn
                645                 650                 655

Leu Thr Thr Leu Arg Asp Gly Leu His Gly Ile Gln Arg Gly Asp Ile
            660                 665                 670

Asp Ala Met Ile Ser Ser Ala Lys Ser Met Val Arg Lys Ala Asn Asp
        675                 680                 685

Ile Thr Asp Glu Val Leu Asp Gly Leu Asn Pro Ile Gln Thr Asp Val
690                 695                 700

Glu Arg Ile Lys Asp Thr Tyr Gly Arg Thr Gln Asn Glu Asp Phe Lys
705                 710                 715                 720

Lys Ala Leu Thr Asp Ala Asp Asn Ser Val Asn Lys Leu Thr Asn Lys
                725                 730                 735

Leu Pro Asp Leu Trp Arg Lys Ile Glu Ser Ile Asn Gln Gln Leu Leu
            740                 745                 750

Pro Leu Gly Asn Ile Ser Asp Asn Met Asp Arg Ile Arg Glu Leu Ile
        755                 760                 765

Gln Gln Ala Arg Asp Ala Ala Ser Lys Val Ala Val Pro Met Arg Phe
770                 775                 780

Asn Gly Lys Ser Gly Val Glu Val Arg Leu Pro Asn Asp Leu Glu Asp
785                 790                 795                 800

Leu Lys Gly Tyr Thr Ser Leu Ser Leu Phe Leu Gln Arg Pro Asn Ser
                805                 810                 815

Arg Glu Asn Gly Gly Thr Glu Asn Met Phe Val Met Tyr Leu Gly Asn
            820                 825                 830

Lys Asp Ala Ser Arg Asp Tyr Ile Gly Met Ala Val Val Asp Gly Gln
        835                 840                 845

Leu Thr Cys Val Tyr Asn Leu Gly Asp Arg Glu Ala Glu Leu Gln Val
850                 855                 860

Asp Gln Ile Leu Thr Lys Ser Glu Thr Lys Glu Ala Val Met Asp Arg
865                 870                 875                 880

Val Lys Phe Gln Arg Ile Tyr Gln Phe Ala Arg Leu Asn Tyr Thr Lys
                885                 890                 895

Gly Ala Thr Ser Ser Lys Pro Glu Thr Pro Gly Val Tyr Asp Met Asp
            900                 905                 910

Gly Arg Asn Ser Asn Thr Leu Leu Asn Leu Asp Pro Glu Asn Val Val
        915                 920                 925

Phe Tyr Val Gly Gly Tyr Pro Pro Asp Phe Lys Leu Pro Ser Arg Leu
930                 935                 940

Ser Phe Pro Pro Tyr Lys Gly Cys Ile Glu Leu Asp Asp Leu Asn Glu
945                 950                 955                 960

Asn Val Leu Ser Leu Tyr Asn Phe Lys Lys Thr Phe Asn Leu Asn Thr
                965                 970                 975

Thr Glu Val Glu Pro Cys Arg Arg Lys Glu Ser Asp Lys Asn
            980                 985                 990

Tyr Phe Glu Gly Thr Gly Tyr Ala Arg Val Pro Thr Gln Pro His Ala
        995                 1000                1005
```

```
Pro Ile Pro Thr Phe Gly Gln Thr Ile Gln Thr Val Asp Arg Gly
    1010                1015                1020

Leu Leu Phe Phe Ala Glu Asn Gly Asp Arg Phe Ile Ser Leu Asn Ile
1025                1030                1035                1040

Glu Asp Gly Lys Leu Met Val Arg Tyr Lys Leu Asn Ser Glu Leu Pro
                1045                1050                1055

Lys Glu Arg Gly Val Gly Asp Ala Ile Asn Asn Gly Arg Asp His Ser
            1060                1065                1070

Ile Gln Ile Lys Ile Gly Lys Leu Gln Lys Arg Met Trp Ile Asn Val
            1075                1080                1085

Asp Val Gln Asn Thr Ile Ile Asp Gly Glu Val Phe Asp Phe Ser Thr
        1090                1095                1100

Tyr Tyr Leu Gly Gly Ile Pro Ile Ala Ile Arg Glu Arg Phe Asn Ile
1105                1110                1115                1120

Ser Thr Pro Ala Phe Arg Gly Cys Met Lys Asn Leu Lys Lys Thr Ser
                1125                1130                1135

Gly Val Val Arg Leu Asn Asp Thr Val Gly Val Thr Lys Lys Cys Ser
            1140                1145                1150

Glu Asp Trp Lys Leu Val Arg Ser Ala Ser Phe Ser Arg Gly Gly Gln
        1155                1160                1165

Leu Ser Phe Thr Asp Leu Gly Leu Pro Pro Thr Asp His Leu Gln Ala
1170                1175                1180

Ser Phe Gly Phe Gln Thr Phe Gln Pro Ser Gly Ile Leu Leu Asp His
1185                1190                1195                1200

Gln Thr Trp Thr Arg Asn Leu Gln Val Thr Leu Glu Asp Gly Tyr Ile
            1205                1210                1215

Glu Leu Ser Thr Ser Asp Ser Gly Ser Pro Ile Phe Lys Ser Pro Gln
        1220                1225                1230

Thr Tyr Met Asp Gly Leu Leu His Tyr Val Ser Val Ile Ser Asp Asn
            1235                1240                1245

Ser Gly Leu Arg Leu Leu Ile Asp Asp Gln Leu Leu Arg Asn Ser Lys
    1250                1255                1260

Arg Leu Lys His Ile Ser Ser Ser Arg Gln Ser Leu Arg Leu Gly Gly
1265                1270                1275                1280

Ser Asn Phe Glu Gly Cys Ile Ser Asn Val Phe Val Gln Arg Leu Ser
            1285                1290                1295

Leu Ser Pro Glu Val Leu Asp Leu Thr Ser Asn Ser Leu Lys Arg Asp
        1300                1305                1310

Val Ser Leu Gly Gly Cys Ser Leu Asn Lys Pro Pro Phe Leu Met Leu
    1315                1320                1325

Leu Lys Gly Ser Thr Arg Phe Asn Lys Thr Lys Thr Phe Arg Ile Asn
    1330                1335                1340

Gln Leu Leu Gln Asp Thr Pro Val Ala Ser Pro Arg Ser Val Lys Val
1345                1350                1355                1360

Trp Gln Asp Ala Cys Ser Pro Leu Pro Lys Thr Gln Ala Asn His Gly
            1365                1370                1375

Ala Leu Gln Phe Gly Asp Ile Pro Thr Ser His Leu Leu Phe Lys Leu
        1380                1385                1390

Pro Gln Glu Leu Leu Lys Pro Arg Ser Gln Phe Ala Val Asp Met Gln
            1395                1400                1405

Thr Thr Ser Ser Arg Gly Leu Val Phe His Thr Gly Thr Lys Asn Ser
    1410                1415                1420

Phe Met Ala Leu Tyr Leu Ser Lys Gly Arg Leu Val Phe Ala Leu Gly
```

-continued

```
1425                1430                1435                1440
Thr Asp Gly Lys Lys Leu Arg Ile Lys Ser Lys Glu Lys Cys Asn Asp
            1445                1450                1455
Gly Lys Trp His Thr Val Val Phe Gly His Asp Gly Glu Lys Gly Arg
        1460                1465                1470
Leu Val Val Asp Gly Leu Arg Ala Arg Glu Gly Ser Leu Pro Gly Asn
    1475                1480                1485
Ser Thr Ile Ser Ile Arg Ala Pro Val Tyr Leu Gly Ser Pro Pro Ser
    1490                1495                1500
Gly Lys Pro Lys Ser Leu Pro Thr Asn Ser Phe Val Gly Cys Leu Lys
1505                1510                1515                1520
Asn Phe Gln Leu Asp Ser Lys Pro Leu Tyr Thr Pro Ser Ser Ser Phe
            1525                1530                1535
Gly Val Ser Ser Cys Leu Gly Gly Pro Leu Glu Lys Gly Ile Tyr Phe
            1540                1545                1550
Ser Glu Glu Gly Gly His Val Leu Ala His Ser Val Leu Leu Gly
        1555                1560                1565
Pro Glu Phe Lys Leu Val Phe Ser Ile Arg Pro Arg Ser Leu Thr Gly
    1570                1575                1580
Ile Leu Ile His Ile Gly Ser Gln Pro Gly Lys His Leu Cys Val Tyr
1585                1590                1595                1600
Leu Glu Ala Gly Lys Val Thr Ala Ser Met Asp Ser Gly Ala Gly Gly
            1605                1610                1615
Thr Ser Thr Ser Val Thr Pro Lys Gln Ser Leu Cys Asp Gly Gln Trp
        1620                1625                1630
His Ser Val Ala Val Thr Ile Lys Gln His Ile Leu His Leu Glu Leu
    1635                1640                1645
Asp Thr Asp Ser Ser Tyr Thr Ala Gly Gln Ile Pro Phe Pro Pro Ala
    1650                1655                1660
Ser Thr Gln Glu Pro Leu His Leu Gly Gly Ala Pro Ala Asn Leu Thr
1665                1670                1675                1680
Thr Leu Arg Ile Pro Val Trp Lys Ser Phe Phe Gly Cys Leu Arg Asn
            1685                1690                1695
Ile His Val Asn His Ile Pro Val Pro Val Thr Glu Ala Leu Glu Val
            1700                1705                1710
Gln Gly Pro Val Ser Leu Asn Gly Cys Pro Asp Gln
        1715                1720

<210> SEQ ID NO 7
<211> LENGTH: 5264
<212> TYPE: DNA
<213> ORGANISM: Rattus norvegicus

<400> SEQUENCE: 7
gtataagagg aagaacacaa aggtttgcag cagccaggca gaacaccaag ggatcaagat      60
gccgcctaca gtgaggtggt cagcctggtg cacaggatgg ctgtggatct ttggggcagc     120
tctgggccag tgcctggggt atggctcaga gcagcaaagg gtagcatttc ttcagcatcc     180
agggcaaaac catctgcaag caagttatat ggagcttaga cccagccagg gctgtcgccc     240
aggatactat cgagacatca aaagcttccc tgcgggaagg tctgttccct gcaattgcaa     300
cggacattca atagatgcc aagacggctc gggagtgtgc attaactgtc agcacaacac     360
agctggggag cactgtgagc gttgcaagag gggttactat ggaagcgcca tccatggatc     420
ctgcagggtt tgcccctgtc ctcacaccaa cagctttgcc actggctgtg ctgtggatgg     480
```

```
aggagctgtg aggtgtgcct gcaaacccgg atacacagga gcacagtgtg agaggtgtgc    540
accaggatat tttgggaacc cccagaaatt tggaggtagc tgccaaccat gcaattgcaa    600
cagtaatggc cagtttggca cttgtgatcc cctaactgga gactgtgtaa gccaagaacc    660
caaagatggc agccctgcag aagaatgtga tgactgtgac agctgtgtga tgactctcct    720
aaatgacttg gtccccatgg gtgaggaact cgccctggtg aaatcaaaac ttcaggggct    780
gagtgtgaac actggttctc tggaacagat ccggcatgtg agatgcagg ccaaggacct    840
gaggaaccag ctgcttggct tccgttccgc catctccagt cacgggtccc aaatggacgg    900
cctggaaaaa gaactcagtc atttgtacca ggaattcgaa actttgcaag aaaaggcgca    960
ggtcaattcc agaaaagcac aaacattata taacaacatc gatacgacaa tccaaaacgc   1020
caaagagttg gacatgaaga ttaaaaacat acttacgaat gtgcacattc tcctgaagca   1080
gatcgctcgg ccaggtggag aaggaatgga cttgccggtg ggcgactggt ccagggagtc   1140
ggcggaagct cagcgcatgt tgcgggagct gcgaggccga gactttaaaa agcacctcca   1200
agaagcagag gcccagaaaa tggaagccca gctcttactg aaccgaatca ggacctggct   1260
ggaatcccac caggtggaga caatggact gctaaagaat attcgggatt cattaaatga   1320
ttatgaagcc aaacttcagg acctgcgttc cgtgcttcag gaggcggcag cccagggaaa   1380
gcaggctaca ggcctcaacc acgaaaatga gggggtccta ggagccatcc agagacaaat   1440
gaaggaaatg gattccctga gaagtacct caccgagcac ctggccacag cagacgcttc   1500
cctgctgcaa accaacagtc tactgcagcg gatggacacg agccagaagg agtatgaaag   1560
cttagctgct gctttaaacg gagcaagaca ggaactgaat gaccaagtgc gggaactctc   1620
cagatccgga ggcaaagcac ccctggtggc tgaggccgag aagcacgctc agtctttaca   1680
ggagctggca aagcagctgg aagagataaa gagaaacacc agtggggatg agtcggtgcg   1740
ctgtgtcgtg gacgctgcca ctgcctatga gagcatcctc aacgccatcc gagcagcaga   1800
ggatgcagcc ggcaaggccg acagtgcctc agagtccgcc ttccagacag tgataaagga   1860
agatcttccg agaagagcca aaaccctgag ttctgacagc gaggaactgt taaacgaggc   1920
caagatgaca cggaaaaggc tacagcaaga atcaatcca gctctcaaca gcctacagca   1980
aaccctgaag actgtatcag ttcagaagga cctgctagat gccaatgtca ctgctgtccg   2040
taatgacctt cgtgggatcc agagaggtga tattgacagt gtggtgagtg agcgaagag    2100
catggtcagg aaagccaatg gataacgag cgaggtcctg gacgggctca gccccatcca   2160
gacggatttg ggaaggatta aggacagcta cgggagcaca cggcatgagg acttcaacaa   2220
agctctgatt gacgccaata actcagtaaa gaaattaacc aagaagttgc ctgatctttt   2280
tgtcaagatt gaaagcatca atcaacagtt gctgcccctg gaaacatct ctgacaatgt    2340
agaccgaatc cgagagctca ttacgcaggc cagagatgct gcgaacaagg ttgcaattcc   2400
catgaggttc aatggtaaat ctggtgttga agtccgtctg ccaaatgacc tagaagactt   2460
gaagggatac acgtctctgt ctttgttcct ccaaagacca gacttaagag agaatggagg   2520
cactgaggac atgtttgtaa tgtaccttgg aaacaaggat gcctccaagg actacatcgg   2580
catggcggtt gtagatggcc agctgacgtg tgtctacaac ctgggggacc gagaagctga   2640
agttcagatc gatcaggtcc tgacggagag tgagtctcag gaggcagtta tggaccgggt   2700
gaagttccag agaatatatc aatttgccaa gcttaattac accaaagaag ccacgtccaa   2760
taaacccaaa gctcccgcgg tctacgacct ggagggtggc agtagcaaca cgctccttaa   2820
```

```
tttggatccc gaggacgctg tgttttatgt cggaggttac ccaccggatt ttgaacttcc    2880
tagcagactg cggttccctc catacaaagg ctgtatcgaa ctagatgacc tcaatgaaaa    2940
cgttctaagc ttgtacaatt tcaagacaac tttcaatctc aacaccacgg aggtggagcc    3000
ttgtaggagg agaaaggaag agtcagacaa aaattacttt gaaggtacag gctatgctcg    3060
catccctact caaccaaatg ctccctttccc aaacttcata cagaccatcc agactactgt   3120
ggacagaggt ttactgttct tcgcagaaaa ccaggataac ttcatatctc tgaacataga    3180
agatggcaat ctcatggtga gatacaaact aaattcagag ccacccaaag agaagggaat    3240
tcgagacacc atcaacgatg ggaaagatca ttcgatctta atcacaattg gaaaactaca    3300
aaaacgcatg tggataaatg tgaacgaacg cagtgtacga atcgaagggg aaatatttga    3360
tttcagcaca tattatttgg gcggaattcc aattgcaatc agagaaaggt ttaacatctc    3420
aacgcctgct ttccaaggct gcatgaagaa tctgaagaaa accagtgggg ttgtcaggtt    3480
gaatgatact gtgggtgtaa ccaagaagtg ctcagaagac tggaagcttg tgcgaaccgc    3540
ctcgttctcc agaggagggc agatgagctt tacaaacttg gacgtgccct cgactgaccg    3600
cttccagctc tcctttgggt ttcagacctt tcaacccagt ggcacactgc tcaatcatca    3660
gacgcggaca agcagcctgc tggtcaccct ggaagatggg cacattgagt tgagcactag    3720
ggacagcaac atcccaattt tcaagtctcc agggacctac atggacggtt tactgcatca    3780
tgtatctgta ataagtgaca cctcaggtct ccgccttctc atcgatgacc aggtcctgag    3840
aaggaaccag aggcttccta gcttctctaa cgcccagcag tcgctccgcc ttggaggagg    3900
tcatttcgag ggttgtatca gcaatgtttt agtccaaagg ttttcacaga gtccagaagt    3960
cctggatctg gccagtaaat ctaccaagaa ggatgcatcc ctaggaggct gcagtttaaa    4020
caagccacct tttcttatgt tgtttaaaag tcccaagaga tttaacaagg gccggatttt    4080
caatgttaat cagctgatgc aagatgcacc tcaggccaca aggagcacag aggcttggca    4140
agatgggagg tcctgcctac cacctctgaa caccaaggcc tctcacagag ccctgcagtt    4200
tggagacagc cccaccagcc acttgctact caagcttccc caggaactgc tgaaacctag    4260
gtcacagttt tctttagaca tacagacaac ttcccccaaa ggactggtgt tttacgcagg    4320
caccaaggac tccttcctgg ctctttatgt cgcagatggc cgtgttgtct ttgctttggg    4380
ggcaggaggg aagaaactga gactcaggag caaggagaga taccatgacg ggaagtggca    4440
cacggtggtg ttcggactaa atggaggaaa ggcacgcctg gttgtggatg gctaagggc     4500
ccaggaaggc agtttgcctg gaaattctac catcagcccc agagaacagg tttacctagg    4560
gttgccgcta tcaagaaagc caaagagcct acccccagcac agttttgtgg ggtgcctgag   4620
agatttccag ttgaactcga aacccctgga ttctccttct gcgaggtttg gggtatctcc    4680
ctgcttgggt ggctctttag agaaaggcat ttatttctcc caaggaggag gccatgtgat    4740
cctagccaat tctgtgtcct tggggccaga gcttaagctc actttcagca ttcgcccacg    4800
gagtctcact ggggtcttaa tacacgtcgg aagtcaatct ggacagcgct aagtgtgta    4860
catggaggca ggaaaggtca aacctctgt gagcagtgat gcaggaggaa gtgtgacatc     4920
aattacaccg aagcagtctc tgtgtgatgg acagtggcac tcggtggcag tctccattaa    4980
acagcgcatc ctgcatctag aactggatac agacagtagc tacacagtcg caccactttc    5040
cttctcacca aacagcaccc gagggtcact gcacgtcgga ggtgtcccag acaaattgaa    5100
aatgcttaca ctccctgtgt ggaactcatt ttttggctgt ctgaagaata ttcaagtcaa    5160
ccatgtccct gtccccatca cagaagccac agaagtccaa ggttctgtca gcctgaatgg    5220
```
ctgccctgac cactaaccct acacagcaag attcacctttt ggag 5264

<210> SEQ ID NO 8
<211> LENGTH: 1725
<212> TYPE: PRT
<213> ORGANISM: Rattus norvegicus

<400> SEQUENCE: 8

Met Pro Pro Thr Val Arg Trp Ser Ala Trp Cys Thr Gly Trp Leu Trp
1               5                   10                  15

Ile Phe Gly Ala Ala Leu Gly Gln Cys Leu Gly Tyr Gly Ser Glu Gln
            20                  25                  30

Gln Arg Val Ala Phe Leu Gln His Pro Gly Gln Asn His Leu Gln Ala
        35                  40                  45

Ser Tyr Met Glu Leu Arg Pro Ser Gln Gly Cys Arg Pro Gly Tyr Tyr
    50                  55                  60

Arg Asp Ile Lys Ser Phe Pro Ala Gly Arg Ser Val Pro Cys Asn Cys
65                  70                  75                  80

Asn Gly His Ser Asn Arg Cys Gln Asp Gly Ser Gly Val Cys Ile Asn
                85                  90                  95

Cys Gln His Asn Thr Ala Gly Glu His Cys Glu Arg Cys Lys Arg Gly
            100                 105                 110

Tyr Tyr Gly Ser Ala Ile His Gly Ser Cys Arg Val Cys Pro Cys Pro
        115                 120                 125

His Thr Asn Ser Phe Ala Thr Gly Cys Ala Val Asp Gly Gly Ala Val
    130                 135                 140

Arg Cys Ala Cys Lys Pro Gly Tyr Thr Gly Ala Gln Cys Glu Arg Cys
145                 150                 155                 160

Ala Pro Gly Tyr Phe Gly Asn Pro Gln Lys Phe Gly Gly Ser Cys Gln
                165                 170                 175

Pro Cys Asn Cys Asn Ser Asn Gly Gln Phe Gly Thr Cys Asp Pro Leu
            180                 185                 190

Thr Gly Asp Cys Val Ser Gln Glu Pro Lys Asp Gly Ser Pro Ala Glu
        195                 200                 205

Glu Cys Asp Asp Cys Asp Ser Cys Val Met Thr Leu Leu Asn Asp Leu
    210                 215                 220

Val Pro Met Gly Glu Glu Leu Ala Leu Val Lys Ser Lys Leu Gln Gly
225                 230                 235                 240

Leu Ser Val Asn Thr Gly Ser Leu Glu Gln Ile Arg His Val Glu Met
                245                 250                 255

Gln Ala Lys Asp Leu Arg Asn Gln Leu Leu Gly Phe Arg Ser Ala Ile
            260                 265                 270

Ser Ser His Gly Ser Gln Met Asp Gly Leu Glu Lys Glu Leu Ser His
        275                 280                 285

Leu Tyr Gln Glu Phe Glu Thr Leu Gln Glu Lys Ala Gln Val Asn Ser
    290                 295                 300

Arg Lys Ala Gln Thr Leu Tyr Asn Asn Ile Asp Thr Thr Ile Gln Asn
305                 310                 315                 320

Ala Lys Glu Leu Asp Met Lys Ile Lys Asn Ile Leu Thr Asn Val His
                325                 330                 335

Ile Leu Leu Lys Gln Ile Ala Arg Pro Gly Gly Glu Gly Met Asp Leu
            340                 345                 350

Pro Val Gly Asp Trp Ser Arg Glu Ser Ala Glu Ala Gln Arg Met Leu
        355                 360                 365

```
Arg Glu Leu Arg Gly Arg Asp Phe Lys Lys His Leu Gln Glu Ala Glu
    370                 375                 380

Ala Gln Lys Met Glu Ala Gln Leu Leu Leu Asn Arg Ile Arg Thr Trp
385                 390                 395                 400

Leu Glu Ser His Gln Val Glu Asn Asn Gly Leu Leu Lys Asn Ile Arg
                405                 410                 415

Asp Ser Leu Asn Asp Tyr Glu Ala Lys Leu Gln Asp Leu Arg Ser Val
            420                 425                 430

Leu Gln Glu Ala Ala Ala Gln Gly Lys Gln Ala Thr Gly Leu Asn His
        435                 440                 445

Glu Asn Glu Gly Val Leu Gly Ala Ile Gln Arg Gln Met Lys Glu Met
    450                 455                 460

Asp Ser Leu Lys Lys Tyr Leu Thr Glu His Leu Ala Thr Ala Asp Ala
465                 470                 475                 480

Ser Leu Leu Gln Thr Asn Ser Leu Leu Gln Arg Met Asp Thr Ser Gln
                485                 490                 495

Lys Glu Tyr Glu Ser Leu Ala Ala Ala Leu Asn Gly Ala Arg Gln Glu
            500                 505                 510

Leu Asn Asp Gln Val Arg Glu Leu Ser Arg Ser Gly Lys Ala Pro
        515                 520                 525

Leu Val Ala Glu Ala Glu Lys His Ala Gln Ser Leu Gln Glu Leu Ala
    530                 535                 540

Lys Gln Leu Glu Glu Ile Lys Arg Asn Thr Ser Gly Asp Glu Ser Val
545                 550                 555                 560

Arg Cys Val Val Asp Ala Ala Thr Ala Tyr Glu Ser Ile Leu Asn Ala
                565                 570                 575

Ile Arg Ala Ala Glu Asp Ala Ala Gly Lys Ala Asp Ser Ala Ser Glu
            580                 585                 590

Ser Ala Phe Gln Thr Val Ile Lys Glu Asp Leu Pro Arg Arg Ala Lys
        595                 600                 605

Thr Leu Ser Ser Asp Ser Glu Glu Leu Leu Asn Glu Ala Lys Met Thr
    610                 615                 620

Arg Lys Arg Leu Gln Gln Glu Ile Asn Pro Ala Leu Asn Ser Leu Gln
625                 630                 635                 640

Gln Thr Leu Lys Thr Val Ser Val Gln Lys Asp Leu Leu Asp Ala Asn
                645                 650                 655

Val Thr Ala Val Arg Asn Asp Leu Arg Gly Ile Gln Arg Gly Asp Ile
            660                 665                 670

Asp Ser Val Val Ser Gly Ala Lys Ser Met Val Arg Lys Ala Asn Gly
        675                 680                 685

Ile Thr Ser Glu Val Leu Asp Gly Leu Ser Pro Ile Gln Thr Asp Leu
    690                 695                 700

Gly Arg Ile Lys Asp Ser Tyr Gly Ser Thr Arg His Glu Asp Phe Asn
705                 710                 715                 720

Lys Ala Leu Ile Asp Ala Asn Asn Ser Val Lys Leu Thr Lys Lys
                725                 730                 735

Leu Pro Asp Leu Phe Val Lys Ile Glu Ser Ile Asn Gln Gln Leu Leu
            740                 745                 750

Pro Leu Gly Asn Ile Ser Asp Asn Val Asp Arg Ile Arg Glu Leu Ile
        755                 760                 765

Thr Gln Ala Arg Asp Ala Ala Asn Lys Val Ala Ile Pro Met Arg Phe
    770                 775                 780
```

-continued

```
Asn Gly Lys Ser Gly Val Glu Val Arg Leu Pro Asn Asp Leu Glu Asp
785                 790                 795                 800

Leu Lys Gly Tyr Thr Ser Leu Ser Leu Phe Leu Gln Arg Pro Asp Leu
            805                 810                 815

Arg Glu Asn Gly Gly Thr Glu Asp Met Phe Val Met Tyr Leu Gly Asn
            820                 825                 830

Lys Asp Ala Ser Lys Asp Tyr Ile Gly Met Ala Val Val Asp Gly Gln
            835                 840                 845

Leu Thr Cys Val Tyr Asn Leu Gly Asp Arg Glu Ala Glu Val Gln Ile
    850                 855                 860

Asp Gln Val Leu Thr Glu Ser Glu Ser Gln Glu Ala Val Met Asp Arg
865                 870                 875                 880

Val Lys Phe Gln Arg Ile Tyr Gln Phe Ala Lys Leu Asn Tyr Thr Lys
            885                 890                 895

Glu Ala Thr Ser Asn Lys Pro Lys Ala Pro Ala Val Tyr Asp Leu Glu
            900                 905                 910

Gly Gly Ser Ser Asn Thr Leu Leu Asn Leu Asp Pro Glu Asp Ala Val
            915                 920                 925

Phe Tyr Val Gly Gly Tyr Pro Pro Asp Phe Glu Leu Pro Ser Arg Leu
    930                 935                 940

Arg Phe Pro Pro Tyr Lys Gly Cys Ile Glu Leu Asp Asp Leu Asn Glu
945                 950                 955                 960

Asn Val Leu Ser Leu Tyr Asn Phe Lys Thr Thr Phe Asn Leu Asn Thr
            965                 970                 975

Thr Glu Val Glu Pro Cys Arg Arg Lys Glu Ser Asp Lys Asn
            980                 985                 990

Tyr Phe Glu Gly Thr Gly Tyr Ala Arg Ile Pro Thr Gln Pro Asn Ala
            995                 1000                1005

Pro Phe Pro Asn Phe Ile Gln Thr Ile Gln Thr Thr Val Asp Arg Gly
    1010                1015                1020

Leu Leu Phe Phe Ala Glu Asn Gln Asp Asn Phe Ile Ser Leu Asn Ile
1025                1030                1035                1040

Glu Asp Gly Asn Leu Met Val Arg Tyr Lys Leu Asn Ser Glu Pro Pro
            1045                1050                1055

Lys Glu Lys Gly Ile Arg Asp Thr Ile Asn Asp Gly Lys Asp His Ser
            1060                1065                1070

Ile Leu Ile Thr Ile Gly Lys Leu Gln Lys Arg Met Trp Ile Asn Val
            1075                1080                1085

Asn Glu Arg Ser Val Arg Ile Glu Gly Glu Ile Phe Asp Phe Ser Thr
            1090                1095                1100

Tyr Tyr Leu Gly Gly Ile Pro Ile Ala Ile Arg Glu Arg Phe Asn Ile
1105                1110                1115                1120

Ser Thr Pro Ala Phe Gln Gly Cys Met Lys Asn Leu Lys Lys Thr Ser
            1125                1130                1135

Gly Val Val Arg Leu Asn Asp Thr Val Gly Val Thr Lys Lys Cys Ser
            1140                1145                1150

Glu Asp Trp Lys Leu Val Arg Thr Ala Ser Phe Ser Arg Gly Gly Gln
            1155                1160                1165

Met Ser Phe Thr Asn Leu Asp Val Pro Ser Thr Asp Arg Phe Gln Leu
    1170                1175                1180

Ser Phe Gly Phe Gln Thr Phe Gln Pro Ser Gly Thr Leu Leu Asn His
1185                1190                1195                1200

Gln Thr Arg Thr Ser Ser Leu Leu Val Thr Leu Glu Asp Gly His Ile
```

-continued

```
                1205                1210                1215
Glu Leu Ser Thr Arg Asp Ser Asn Ile Pro Ile Phe Lys Ser Pro Gly
            1220                1225                1230

Thr Tyr Met Asp Gly Leu Leu His His Val Ser Val Ile Ser Asp Thr
            1235                1240                1245

Ser Gly Leu Arg Leu Leu Ile Asp Asp Gln Val Leu Arg Arg Asn Gln
            1250                1255                1260

Arg Leu Pro Ser Phe Ser Asn Ala Gln Gln Ser Leu Arg Leu Gly Gly
1265                1270                1275                1280

Gly His Phe Glu Gly Cys Ile Ser Asn Val Leu Val Gln Arg Phe Ser
            1285                1290                1295

Gln Ser Pro Glu Val Leu Asp Leu Ala Ser Lys Ser Thr Lys Lys Asp
            1300                1305                1310

Ala Ser Leu Gly Gly Cys Ser Leu Asn Lys Pro Pro Phe Leu Met Leu
            1315                1320                1325

Phe Lys Ser Pro Lys Arg Phe Asn Lys Gly Arg Ile Phe Asn Val Asn
            1330                1335                1340

Gln Leu Met Gln Asp Ala Pro Gln Ala Thr Arg Ser Thr Glu Ala Trp
1345                1350                1355                1360

Gln Asp Gly Arg Ser Cys Leu Pro Pro Leu Asn Thr Lys Ala Ser His
            1365                1370                1375

Arg Ala Leu Gln Phe Gly Asp Ser Pro Thr Ser His Leu Leu Leu Lys
            1380                1385                1390

Leu Pro Gln Glu Leu Leu Lys Pro Arg Ser Gln Phe Ser Leu Asp Ile
            1395                1400                1405

Gln Thr Thr Ser Pro Lys Gly Leu Val Phe Tyr Ala Gly Thr Lys Asp
            1410                1415                1420

Ser Phe Leu Ala Leu Tyr Val Ala Asp Gly Arg Val Val Phe Ala Leu
1425                1430                1435                1440

Gly Ala Gly Gly Lys Lys Leu Arg Leu Arg Ser Lys Glu Arg Tyr His
            1445                1450                1455

Asp Gly Lys Trp His Thr Val Val Phe Gly Leu Asn Gly Gly Lys Ala
            1460                1465                1470

Arg Leu Val Val Asp Gly Leu Arg Ala Gln Glu Gly Ser Leu Pro Gly
            1475                1480                1485

Asn Ser Thr Ile Ser Pro Arg Glu Gln Val Tyr Leu Gly Leu Pro Leu
            1490                1495                1500

Ser Arg Lys Pro Lys Ser Leu Pro Gln His Ser Phe Val Gly Cys Leu
1505                1510                1515                1520

Arg Asp Phe Gln Leu Asn Ser Lys Pro Leu Asp Ser Pro Ser Ala Arg
            1525                1530                1535

Phe Gly Val Ser Pro Cys Leu Gly Gly Ser Leu Glu Lys Gly Ile Tyr
            1540                1545                1550

Phe Ser Gln Gly Gly His Val Ile Leu Ala Asn Ser Val Ser Leu
            1555                1560                1565

Gly Pro Glu Leu Lys Leu Thr Phe Ser Ile Arg Pro Arg Ser Leu Thr
            1570                1575                1580

Gly Val Leu Ile His Val Gly Ser Gln Ser Gly Gln Arg Leu Ser Val
1585                1590                1595                1600

Tyr Met Glu Ala Gly Lys Val Thr Thr Ser Val Ser Ser Asp Ala Gly
            1605                1610                1615

Gly Ser Val Thr Ser Ile Thr Pro Lys Gln Ser Leu Cys Asp Gly Gln
            1620                1625                1630
```

```
Trp His Ser Val Ala Val Ser Ile Lys Gln Arg Ile Leu His Leu Glu
        1635                1640                1645
Leu Asp Thr Asp Ser Ser Tyr Thr Val Ala Pro Leu Ser Phe Ser Pro
    1650                1655                1660
Asn Ser Thr Arg Gly Ser Leu His Val Gly Gly Val Pro Asp Lys Leu
1665                1670                1675                1680
Lys Met Leu Thr Leu Pro Val Trp Asn Ser Phe Phe Gly Cys Leu Lys
            1685                1690                1695
Asn Ile Gln Val Asn His Val Pro Val Pro Ile Thr Glu Ala Thr Glu
        1700                1705                1710
Val Gln Gly Ser Val Ser Leu Asn Gly Cys Pro Asp His
        1715                1720                1725

<210> SEQ ID NO 9
<211> LENGTH: 7323
<212> TYPE: DNA
<213> ORGANISM: Mus musculus

<400> SEQUENCE: 9
atgtcagagg gcatttgctg ccgagctggc gcactgtgca agagtggaca gcaagtttcc      60
actgtggtgg tggtagatcc accaaaccat gccagtggaa tgagaactga atgcagccca     120
ccagagcacg tgcacacgtg cattaaggaa cctcagaatc agctcttcca tgtggcttat     180
atcttaatca aatttgcaaa ctctccccgc cctgatcttt ggatcctgga agatctgta      240
gactttggaa gcacctactc accatggcag tattttgctc attctagaag agattgtgta     300
gaacagtttg gcaagaagc aaacatggca attacccagg cgaccagat gctctgtgtc      360
acggagtatt cccgtatcgt gcctctggaa atggcgaga ttgttgtatc cttgataaat      420
ggtcgtccag gtgcaaaaaa gtttgctttc tctgacactc tgagggagtt tactaaggca     480
acaaacatcc gcttgcggtt tctgcgaacc aacacccctcc tcgggcatct tatttccaag    540
gcagagcgag accccactgt cacgcgccgg tattattgca tggaagctga tgatgctctg     600
ttctctgtcc tgcagtatta ttacagcata aggatatca gtgttggtgg gcggtgtgtt     660
tgcaacggcc atgcggaggc gtgcagtgct gacaaccctg aaaagcagtt ccgatgcgaa     720
tgccagcacc atacctgtgg agacacgtgt aaccgctgct gtgcaggtta caatcagagg     780
cgctggcagc ctgctggtca ggagcagcac aatgagtgtg aagcctgcaa ctgccatggg     840
catgctgtgg actgctacta tgacccagac gtggagcacc agcaggcgag cttgaacagc     900
aaaggcgtct acgcaggtgg aggggtctgc atcaactgtc agcacaacac tgcaggcgtg     960
aactgtgaaa agtgtgcgaa gggttacttc cggccccatg gagttccggt ggatgcactg    1020
catggatgca tcccttgcag ctgtgaccca gaacgcgcag atgactgtga ccagggctca    1080
ggccactgcc attgtaagcc aaatttctcc ggagactact gtgagacgtg tgcagatggg    1140
tactataatt ttccatttg cttgagaatt ccagtctttc ccaactacac tccaagtcca    1200
gaagatccag tggctggcaa tataaaaggc aaggatccag ggactctaga cccaccagtc    1260
atagcaaatg gggcatatct tggagcttca agactagagc aaggagccac aggccagggc    1320
agccctgctg agagggtcac ccacaccaac tcatggctga gttcctcaat gcctatgctc    1380
caggttaggg ctgccatcca tgaggctaag tgttactctc tgtgtttctg tatgtatgtt    1440
gagcacagtg ggactgtacc acctgctctg gggtcaggtt atacagggga ctctgagcct    1500
aaaacaggaa cccaggcaaa aagggggtgt gactgtaact tggaaggtgt tctcccagag    1560
```

```
atatgtgacg atcgtggcag gtgcctgtgc cgccctgggg ttgagggtcc ccagtgtgac    1620
tcctgccgct cgggctccta ttcatttccc atatgccaag cttgccagtg ttcgacgatt    1680
ggatcctatc cagtgccctg tgacccgggg aatggccagt gtgactgcct gcctggaatt    1740
accgggaggc agtgtgacag gtgtctctcg ggagcctatg actttccata ctgccaaggt    1800
aaggaagccg gcagcatgtt ggaggctcgg tcctcatctg agtgggtgca gctgacctct    1860
tggagaagcc tgggttattg tcagtgcaag cagcatgttg caagtcctac atgtagtgtc    1920
tgcaaaccat tatattggaa tctggccaaa gaaaaccccc gtggatgctc agagtgccag    1980
tgccatgaag cagggacatt gagtggaatt ggagagtgtg ggcaggagga cggtgactgt    2040
agctgcaaag cccatgtaac tggtgatgcc tgcgacacct gtgaagatgg gttttttctct    2100 ttggagaaga gcaattactt tggctgtcaa gggtgtcagt gtgacattgg tggagcactc    2160
accaccatgt gtagtgggcc ctcgggagta tgccagtgca gagagcacgt ggaggggaaa    2220
cagtgccaga ggcctgaaaa taactactac ttcccggatt tgcaccacat gaagtatgag    2280
gtcgaagatg gcactggacc taatggaaga aacctgcggt ttggatttga tcccctggta    2340
ttccctgagt ttagctggag aggatatgct ccaatgacct cagtccaggt atatatgagt    2400
gagtgtgtgt gtcctctaca ctgcatgtta ttttgggta cttttcagaa tgaagtaagg    2460
gtgagattgt ctgtgaggca gtccagcctc tccttgttcc gcatcgttct gagatacatc    2520
agtcctggaa cggaagccat atccggccga atcactcttt actcatcgca gggagattcg    2580
gatgctttgc aaagcagaaa aatcaccttt cccccgagta aagagccagc ctttgtcaca    2640
gtccctggga atggctttgc aggcccattc tccatcacac ctgggacgtg gattgcttgc    2700
atccaggtgg aaggagtcct tctggactac ctggtgctgc ttcccaggga ctactatgaa    2760
gcattcaccc tgcaagtgcc agtcacagag ccatgtgccc acacaggatc tccccaggac    2820
aactgtttgc tttaccagca tttaccactg actgcattct cctgtaccct ggcttgtgag    2880
gccagacact tcctgctgga tggagagctg agacccttgg caatgaggca gcccacaccc    2940
acacacccag ccatggtgga cctcagcggg agagaggtag aactgcagct tcgtctgcgg    3000
gtcccacagg ttggccacta cgtggtcctg ctggagtatg ccacggaggt ggagcagctt    3060
tttgtggtgg acgtgaatct gaagagctca gggtctgcct tggcaggcca ggtgaacata    3120
tacagctgca agtacagcat cccgtgcagg agtgtggtga ttgacagcct gagtcgcacg    3180
gctgtacatg agctgttggc agatgcagac attcagctca aggcgcacat ggcccatttc    3240
cttttgtatc acatttgtat tataccagct gaagaattct caactgaata tttgagacct    3300
caagtccact gcattgccag ctacaggcag catgctaatc caagtgcttc ctgtgtctcc    3360
ctggcccatg aaactcctcc aacagcctca attttggatg ctacaagtag ggccttttc    3420 tctgccctac ctcatgagcc ttcctctcct gcagatggag ttactctgaa ggcaccacag    3480
agtcaagtga ccctgaaagg actcatacca cacctgggcc gacacgtctt tgtcatccat    3540
ttttatcaag cagagcaccc agggtttccc actgaggtga ttgtgaatgg aggaagacag    3600
tggtcaggtt ccttccttgc ctccttctgt cccactttac ttggctgccg ggaccaggtg    3660
atctctgatg gccaagtgga gtttgacatc tctgaagcag aggtagctgt gacagtgaag    3720
attccagatg gaaagtcctt aacattggtc cgggttctag tggtacctgc agagaattac    3780
gactaccaaa ttcttcacaa aacaacagtg gacaagtcct ccgagttcat cagcagttgt    3840
ggaggagaca gcttttatat tgatcccag gcagcctctg gattctgtaa gaattctgca    3900
aggtccctgg tagccttta ccataacggt gccataccct gtgagtgcga ccctgctggg    3960
```

```
actgccggcc accactgtag tcctgagggt gggcagtgcc cttgccggcc caatgtcatc    4020
gggaggcagt gcagccgctg tgcgacaggc tactatggat tcccatactg caagccttgt    4080
aattgtggca gacgcctttg tgaagaggtg acagggaagt gtctctgccc accccacaca    4140
gtcaggcctc agtgtgaggt ctgtgagatg aattccttca actttcaccc tgtggctggc    4200
tgtgacgtct gcaactgctc caggaagggc accattgagg cggccgtctc tgagtgtgac    4260
agggacagcg gcagtgcag gtgcaagcct agagtcacag ggcagcagtg tgacaagtgt    4320
gctcctggct tctaccagtt ccctgagtgt gtcccctgca gctgtaacag agatgggact    4380
gagcccagcg tatgtgaccc agagactggg gcttgcatgt gcaaggaaaa tgtagagggc    4440
ccccaatgtc aactgtgtcg agaaggatca ttctacctgg acccaacaaa cccaaagggt    4500
tgtaccaagt gcttctgttt tggagtgaat actgactgtc agagttcgca taagcaacga    4560
gctaagtttg tagacatgat gggctggcgt ctggagacag cagatggagt tgatgtccct    4620
gtgtccttca accctggcag caacagcatg gtggcagatc tgcaggagct gccaccctca    4680
gttcacagtg catcctgggt ggcacctcca tcctacctag gtgataaggt atcatcgtac    4740
ggcggctacc tcacctacca cgccaagtcc tttggcttac ctggagatat ggttcttctg    4800
ggaaagcagc cagatgtgca gctcactggt caacacatgt ccctcatcca taaggaaccc    4860
agcgacccac ggccagacag gctgcatcac ggaagagtgc aagtgattga gggaaacttc    4920
agacacgaag gcagcagtgc cccagtgtcc cggaggagc tgatgactgt gctgtccaga    4980
ctggaaagac tccacatccg gggcctccat ttcaccgaga cacagcggct caccttgggt    5040
gaggtagggc tggaggaggc ctctgacacg ggaagcggac ccagggctca tcttgtggag    5100
atgtgtgcct gccccctga ctacacaggt gactcatgcc agggttgtcg ccctggatac    5160
tattgggaca caaaagctt acctgtagga aggtgtgttc cctgcaattg caacggacat    5220
tcaaatagat gccaggatgg ctccgggata tgcattaact gtcagcacaa cacagctggg    5280
gagcactgtg agcgttgcca agcaggtcac tatggaaatg ccatccacgg atcttgtagg    5340 gtctgccccct gccctcatac caacagtttt gccaccggct gtgctgtgga tggtggagct    5400
gtgaggtgtg cctgcaaacc cggatacaca ggaacacagt gtgagaggtg tgcaccagga    5460
tattttggga acccccagaa atttggaggt agctgccagc catgcaattg taacagcaat    5520
ggccagttag gtccttgcga ccccctaact ggagactgtg taaaccaaga acccaaagat    5580
ggcagccctg cagaagaatg tgatgactgc gacagctgtg tgatgacgct cttaaatgac    5640
ttggcctcca tgggtgagga actccgcctg gtgaagtcaa agctgcaggg gctgagtgtg    5700
agcacgggtc tctgaaca gatccggcac atggagacgc aggccaagga cctgaggaac    5760
cagctgcttg gcttccgttc tgccacctca agtcatgggt ccaaaatgga tgacctggaa    5820
aaagagctga gtcatttgaa ccgggaattt gaaactctgc agaaaaggc acaggtcaat    5880 tccagaaaag cacaaacatt atataacaac attgatcaga caatccaaag tgccaaagaa    5940
ctggacatga agattaaaaa catcgttcag aatgtgcaca ttctcctgaa gcagatggcg    6000
aggccaggtg gagaaggcac ggacttgcca gtgggtgact ggtccaggga gctggccgaa    6060
gctcaacgca tgatgcgaga cctgcgaagc cgagacttta aaagcacct ccaagaagca    6120 gaggccgaga aaatggaagc ccagctctta ctgcaccgga tcaggacctg gctggaatcc    6180
caccaggtgg agaacaacgg actgctaaag aatattcggg actccttaaa tgattatgaa    6240
gacaaacttc aggacctacg ttccatcctc caggaggcag ctgcccaggc aaagcaggcc    6300
```

-continued

```
actggcatca accatgaaaa tgaggggtt ctcggagcca tccagagaca aatgaaagaa    6360
atggattccc tgaagaatga cttcaccaag tacctggcca cagccgactc ttccctgctg    6420
cagaccaaca atctactgca gcagatggac aaaagccaga aggaatatga agcttagct    6480 gctgctttaa atggagcaag acaggaactg agtgacagag tgcgagaact gtccagatcg    6540
ggtggcaaag caccgctggt ggtggaggca gagaagcatg cacagtcttt acaggagctg    6600
gcaaagcagc tggaagagat aaagagaaac accagcgggg atgagctggt gcgttgtgct    6660
gtggatgctg ccacggccta tgagaacatc tcaatgcca tcagagcagc agaggatgca    6720
gccagcaagg ccaccagtgc ctccaagtct gccttccaaa cagtgataaa ggaagacctt    6780
ccaaaaagag ctaagaccct gagttctgac agcgaggaac tgttaaatga agccaagatg    6840
acacagaaaa ggctacagca agtcagtcca gctctcaaca gcctacaaca aaccctgaag    6900
actgtatcag ttcagaagga cctgctagat gccaacctca ctgttgcccg tgatgatctt    6960
catgggatac agagaggtga tatcgacagt gtggtgatcg gtgcaaagag catggtcagg    7020
gaagccaacg gaataacaag cgaggtcctg gacgggctca accccatcca gacagatttg    7080
ggaaggatta aggacagcta tgagagcgca cggcgtgaag acttcagcaa ggctctggtc    7140
gatgccaata actcagtaaa gaaattaacc aggaagttgc ctgatctttt tatcaagatt    7200
gaaagtatca accaacagtt gctgcccctg gggaacatct ctgacaatgt ggaccgaatc    7260
cgagaactca ttcagcaggc cagagatgct gcaaacaagg tgggtattcc catttggctc    7320
tag                                                                  7323
```

<210> SEQ ID NO 10
<211> LENGTH: 2440
<212> TYPE: PRT
<213> ORGANISM: Mus musculus

<400> SEQUENCE: 10

```
Met Ser Glu Gly Ile Cys Cys Arg Ala Gly Ala Leu Cys Lys Ser Gly
  1               5                  10                  15

Gln Gln Val Ser Thr Val Val Val Asp Pro Pro Asn His Ala Ser
             20                  25                  30

Gly Met Arg Thr Glu Cys Ser Pro Pro Glu His Val His Thr Cys Ile
         35                  40                  45

Lys Glu Pro Gln Asn Gln Leu Phe His Val Ala Tyr Ile Leu Ile Lys
     50                  55                  60

Phe Ala Asn Ser Pro Arg Pro Asp Leu Trp Ile Leu Glu Arg Ser Val
 65                  70                  75                  80

Asp Phe Gly Ser Thr Tyr Ser Pro Trp Gln Tyr Phe Ala His Ser Arg
                 85                  90                  95

Arg Asp Cys Val Glu Gln Phe Gly Gln Glu Ala Asn Met Ala Ile Thr
            100                 105                 110

Gln Asp Gln Met Leu Cys Val Thr Glu Tyr Ser Arg Ile Val Pro
        115                 120                 125

Leu Glu Asn Gly Glu Ile Val Val Ser Leu Ile Asn Gly Arg Pro Gly
    130                 135                 140

Ala Lys Lys Phe Ala Phe Ser Asp Thr Leu Arg Glu Phe Thr Lys Ala
145                 150                 155                 160

Thr Asn Ile Arg Leu Arg Phe Leu Arg Thr Asn Thr Leu Leu Gly His
                165                 170                 175

Leu Ile Ser Lys Ala Glu Arg Asp Pro Thr Val Thr Arg Arg Tyr Tyr
            180                 185                 190
```

-continued

```
Cys Met Glu Ala Asp Asp Ala Leu Phe Ser Val Leu Gln Tyr Tyr Tyr
            195                 200                 205
Ser Ile Lys Asp Ile Ser Val Gly Gly Arg Cys Val Cys Asn Gly His
        210                 215                 220
Ala Glu Ala Cys Ser Ala Asp Asn Pro Glu Lys Gln Phe Arg Cys Glu
225                 230                 235                 240
Cys Gln His His Thr Cys Gly Asp Thr Cys Asn Arg Cys Cys Ala Gly
                245                 250                 255
Tyr Asn Gln Arg Arg Trp Gln Pro Ala Gly Gln Glu Gln His Asn Glu
            260                 265                 270
Cys Glu Ala Cys Asn Cys His Gly His Ala Val Asp Cys Tyr Tyr Asp
        275                 280                 285
Pro Asp Val Glu His Gln Gln Ala Ser Leu Asn Ser Lys Gly Val Tyr
290                 295                 300
Ala Gly Gly Val Cys Ile Asn Cys Gln His Asn Thr Ala Gly Val
305                 310                 315                 320
Asn Cys Glu Lys Cys Ala Lys Gly Tyr Phe Arg Pro His Gly Val Pro
            325                 330                 335
Val Asp Ala Leu His Gly Cys Ile Pro Cys Ser Cys Asp Pro Glu Arg
        340                 345                 350
Ala Asp Asp Cys Asp Gln Gly Ser Gly His Cys His Cys Lys Pro Asn
            355                 360                 365
Phe Ser Gly Asp Tyr Cys Glu Thr Cys Ala Asp Gly Tyr Tyr Asn Phe
370                 375                 380
Pro Phe Cys Leu Arg Ile Pro Val Phe Pro Asn Tyr Thr Pro Ser Pro
385                 390                 395                 400
Glu Asp Pro Val Ala Gly Asn Ile Lys Gly Lys Asp Pro Gly Thr Leu
            405                 410                 415
Asp Pro Pro Val Ile Ala Asn Gly Ala Tyr Leu Gly Ala Ser Arg Leu
        420                 425                 430
Glu Gln Gly Ala Thr Gly Gln Gly Ser Pro Ala Glu Arg Val Thr His
            435                 440                 445
Thr Asn Ser Trp Leu Ser Ser Ser Met Pro Met Leu Gln Val Arg Ala
450                 455                 460
Ala Ile His Glu Ala Lys Cys Tyr Ser Leu Cys Phe Cys Met Tyr Val
465                 470                 475                 480
Glu His Ser Gly Thr Val Pro Pro Ala Leu Gly Ser Gly Tyr Thr Gly
            485                 490                 495
Asp Ser Glu Pro Lys Thr Gly Thr Gln Ala Lys Arg Gly Cys Asp Cys
        500                 505                 510
Asn Leu Glu Gly Val Leu Pro Glu Ile Cys Asp Asp Arg Gly Arg Cys
            515                 520                 525
Leu Cys Arg Pro Gly Val Glu Gly Pro Gln Cys Asp Ser Cys Arg Ser
        530                 535                 540
Gly Ser Tyr Ser Phe Pro Ile Cys Gln Ala Cys Gln Cys Ser Thr Ile
545                 550                 555                 560
Gly Ser Tyr Pro Val Pro Cys Asp Pro Gly Asn Gly Gln Cys Asp Cys
            565                 570                 575
Leu Pro Gly Ile Thr Gly Arg Gln Cys Asp Arg Cys Leu Ser Gly Ala
        580                 585                 590
Tyr Asp Phe Pro Tyr Cys Gln Gly Lys Glu Ala Gly Ser Met Leu Glu
            595                 600                 605
```

-continued

```
Ala Arg Ser Ser Ser Glu Trp Val Gln Leu Thr Ser Trp Arg Ser Leu
    610                 615                 620
Gly Tyr Cys Gln Cys Lys Gln His Val Ala Ser Pro Thr Cys Ser Val
625                 630                 635                 640
Cys Lys Pro Leu Tyr Trp Asn Leu Ala Lys Glu Asn Pro Arg Gly Cys
                645                 650                 655
Ser Glu Cys Gln Cys His Glu Ala Gly Thr Leu Ser Gly Ile Gly Glu
                660                 665                 670
Cys Gly Gln Glu Asp Gly Asp Cys Ser Cys Lys Ala His Val Thr Gly
                675                 680                 685
Asp Ala Cys Asp Thr Cys Glu Asp Gly Phe Phe Ser Leu Glu Lys Ser
    690                 695                 700
Asn Tyr Phe Gly Cys Gln Gly Cys Gln Cys Asp Ile Gly Gly Ala Leu
705                 710                 715                 720
Thr Thr Met Cys Ser Gly Pro Ser Gly Val Cys Gln Cys Arg Glu His
                725                 730                 735
Val Glu Gly Lys Gln Cys Gln Arg Pro Glu Asn Asn Tyr Tyr Phe Pro
                740                 745                 750
Asp Leu His His Met Lys Tyr Glu Val Glu Asp Gly Thr Gly Pro Asn
                755                 760                 765
Gly Arg Asn Leu Arg Phe Gly Phe Asp Pro Leu Val Phe Pro Glu Phe
    770                 775                 780
Ser Trp Arg Gly Tyr Ala Pro Met Thr Ser Val Gln Val Tyr Met Ser
785                 790                 795                 800
Glu Cys Val Cys Pro Leu His Cys Met Leu Phe Trp Gly Thr Phe Gln
                805                 810                 815
Asn Glu Val Arg Val Arg Leu Ser Val Arg Gln Ser Ser Leu Ser Leu
                820                 825                 830
Phe Arg Ile Val Leu Arg Tyr Ile Ser Pro Gly Thr Glu Ala Ile Ser
    835                 840                 845
Gly Arg Ile Thr Leu Tyr Ser Ser Gln Gly Asp Ser Asp Ala Leu Gln
850                 855                 860
Ser Arg Lys Ile Thr Phe Pro Pro Ser Lys Glu Pro Ala Phe Val Thr
865                 870                 875                 880
Val Pro Gly Asn Gly Phe Ala Gly Pro Phe Ser Ile Thr Pro Gly Thr
                885                 890                 895
Trp Ile Ala Cys Ile Gln Val Glu Gly Val Leu Leu Asp Tyr Leu Val
                900                 905                 910
Leu Leu Pro Arg Asp Tyr Tyr Glu Ala Phe Thr Leu Gln Val Pro Val
    915                 920                 925
Thr Glu Pro Cys Ala His Thr Gly Ser Pro Gln Asp Asn Cys Leu Leu
    930                 935                 940
Tyr Gln His Leu Pro Leu Thr Ala Phe Ser Cys Thr Leu Ala Cys Glu
945                 950                 955                 960
Ala Arg His Phe Leu Leu Asp Gly Glu Leu Arg Pro Leu Ala Met Arg
                965                 970                 975
Gln Pro Thr Pro Thr His Pro Ala Met Val Asp Leu Ser Gly Arg Glu
                980                 985                 990
Val Glu Leu Gln Leu Arg Leu Arg Val Pro Gln Val Gly His Tyr Val
                995                1000                1005
Val Leu Leu Glu Tyr Ala Thr Glu Val Glu Gln Leu Phe Val Val Asp
    1010                1015                1020
Val Asn Leu Lys Ser Ser Gly Ser Ala Leu Ala Gly Gln Val Asn Ile
```

-continued

```
              1025                1030                1035                1040
Tyr Ser Cys Lys Tyr Ser Ile Pro Cys Arg Ser Val Val Ile Asp Ser
                1045                1050                1055
Leu Ser Arg Thr Ala Val His Glu Leu Leu Ala Asp Ala Asp Ile Gln
                1060                1065                1070
Leu Lys Ala His Met Ala His Phe Leu Leu Tyr His Ile Cys Ile Ile
                1075                1080                1085
Pro Ala Glu Glu Phe Ser Thr Glu Tyr Leu Arg Pro Gln Val His Cys
                1090                1095                1100
Ile Ala Ser Tyr Arg Gln His Ala Asn Pro Ser Ala Ser Cys Val Ser
1105                1110                1115                1120
Leu Ala His Glu Thr Pro Pro Thr Ala Ser Ile Leu Asp Ala Thr Ser
                1125                1130                1135
Arg Gly Leu Phe Ser Ala Leu Pro His Glu Pro Ser Ser Pro Ala Asp
                1140                1145                1150
Gly Val Thr Leu Lys Ala Pro Gln Ser Gln Val Thr Leu Lys Gly Leu
                1155                1160                1165
Ile Pro His Leu Gly Arg His Val Phe Val Ile His Phe Tyr Gln Ala
                1170                1175                1180
Glu His Pro Gly Phe Pro Thr Glu Val Ile Val Asn Gly Gly Arg Gln
1185                1190                1195                1200
Trp Ser Gly Ser Phe Leu Ala Ser Phe Cys Pro His Leu Leu Gly Cys
                1205                1210                1215
Arg Asp Gln Val Ile Ser Asp Gly Gln Val Glu Phe Asp Ile Ser Glu
                1220                1225                1230
Ala Glu Val Ala Val Thr Val Lys Ile Pro Asp Gly Lys Ser Leu Thr
                1235                1240                1245
Leu Val Arg Val Leu Val Val Pro Ala Glu Asn Tyr Asp Tyr Gln Ile
                1250                1255                1260
Leu His Lys Thr Thr Val Asp Lys Ser Ser Glu Phe Ile Ser Ser Cys
1265                1270                1275                1280
Gly Gly Asp Ser Phe Tyr Ile Asp Pro Gln Ala Ala Ser Gly Phe Cys
                1285                1290                1295
Lys Asn Ser Ala Arg Ser Leu Val Ala Phe Tyr His Asn Gly Ala Ile
                1300                1305                1310
Pro Cys Glu Cys Asp Pro Ala Gly Thr Ala Gly His His Cys Ser Pro
                1315                1320                1325
Glu Gly Gly Gln Cys Pro Cys Arg Pro Asn Val Ile Gly Arg Gln Cys
                1330                1335                1340
Ser Arg Cys Ala Thr Gly Tyr Tyr Gly Phe Pro Tyr Cys Lys Pro Cys
1345                1350                1355                1360
Asn Cys Gly Arg Arg Leu Cys Glu Glu Val Thr Gly Lys Cys Leu Cys
                1365                1370                1375
Pro Pro His Thr Val Arg Pro Gln Cys Glu Val Cys Glu Met Asn Ser
                1380                1385                1390
Phe Asn Phe His Pro Val Ala Gly Cys Asp Val Cys Asn Cys Ser Arg
                1395                1400                1405
Lys Gly Thr Ile Glu Ala Ala Val Ser Glu Cys Asp Arg Asp Ser Gly
                1410                1415                1420
Gln Cys Arg Cys Lys Pro Arg Val Thr Gly Gln Gln Cys Asp Lys Cys
1425                1430                1435                1440
Ala Pro Gly Phe Tyr Gln Phe Pro Glu Cys Val Pro Cys Ser Cys Asn
                1445                1450                1455
```

-continued

```
Arg Asp Gly Thr Glu Pro Ser Val Cys Asp Pro Glu Thr Gly Ala Cys
            1460                1465                1470

Met Cys Lys Glu Asn Val Glu Gly Pro Gln Cys Gln Leu Cys Arg Glu
        1475                1480                1485

Gly Ser Phe Tyr Leu Asp Pro Thr Asn Pro Lys Gly Cys Thr Lys Cys
        1490                1495                1500

Phe Cys Phe Gly Val Asn Thr Asp Cys Gln Ser Ser His Lys Gln Arg
1505                1510                1515                1520

Ala Lys Phe Val Asp Met Met Gly Trp Arg Leu Glu Thr Ala Asp Gly
            1525                1530                1535

Val Asp Val Pro Val Ser Phe Asn Pro Gly Ser Asn Ser Met Val Ala
            1540                1545                1550

Asp Leu Gln Glu Leu Pro Pro Ser Val His Ser Ala Ser Trp Val Ala
            1555                1560                1565

Pro Pro Ser Tyr Leu Gly Asp Lys Val Ser Ser Tyr Gly Gly Tyr Leu
            1570                1575                1580

Thr Tyr His Ala Lys Ser Phe Gly Leu Pro Gly Asp Met Val Leu Leu
1585                1590                1595                1600

Gly Lys Gln Pro Asp Val Gln Leu Thr Gly Gln His Met Ser Leu Ile
            1605                1610                1615

His Lys Glu Pro Ser Asp Pro Arg Pro Asp Arg Leu His His Gly Arg
            1620                1625                1630

Val Gln Val Ile Glu Gly Asn Phe Arg His Glu Gly Ser Ser Ala Pro
            1635                1640                1645

Val Ser Arg Glu Glu Leu Met Thr Val Leu Ser Arg Leu Glu Arg Leu
            1650                1655                1660

His Ile Arg Gly Leu His Phe Thr Glu Thr Gln Arg Leu Thr Leu Gly
1665                1670                1675                1680

Glu Val Gly Leu Glu Glu Ala Ser Asp Thr Gly Ser Gly Pro Arg Ala
            1685                1690                1695

His Leu Val Glu Met Cys Ala Cys Pro Pro Asp Tyr Thr Gly Asp Ser
            1700                1705                1710

Cys Gln Gly Cys Arg Pro Gly Tyr Tyr Trp Asp Asn Lys Ser Leu Pro
            1715                1720                1725

Val Gly Arg Cys Val Pro Cys Asn Cys Asn Gly His Ser Asn Arg Cys
            1730                1735                1740

Gln Asp Gly Ser Gly Ile Cys Ile Asn Cys Gln His Asn Thr Ala Gly
1745                1750                1755                1760

Glu His Cys Glu Arg Cys Gln Ala Gly His Tyr Gly Asn Ala Ile His
            1765                1770                1775

Gly Ser Cys Arg Val Cys Pro Cys Pro His Thr Asn Ser Phe Ala Thr
            1780                1785                1790

Gly Cys Ala Val Asp Gly Gly Ala Val Arg Cys Ala Cys Lys Pro Gly
            1795                1800                1805

Tyr Thr Gly Thr Gln Cys Glu Arg Cys Ala Pro Gly Tyr Phe Gly Asn
            1810                1815                1820

Pro Gln Lys Phe Gly Gly Ser Cys Gln Pro Cys Asn Cys Asn Ser Asn
1825                1830                1835                1840

Gly Gln Leu Gly Pro Cys Asp Pro Leu Thr Gly Asp Cys Val Asn Gln
            1845                1850                1855

Glu Pro Lys Asp Gly Ser Pro Ala Glu Glu Cys Asp Asp Cys Asp Ser
            1860                1865                1870
```

```
Cys Val Met Thr Leu Leu Asn Asp Leu Ala Ser Met Gly Glu Glu Leu
        1875                1880                1885

Arg Leu Val Lys Ser Lys Leu Gln Gly Leu Ser Val Ser Thr Gly Ala
        1890                1895                1900

Leu Glu Gln Ile Arg His Met Glu Thr Gln Ala Lys Asp Leu Arg Asn
1905                1910                1915                1920

Gln Leu Leu Gly Phe Arg Ser Ala Thr Ser Ser His Gly Ser Lys Met
            1925                1930                1935

Asp Asp Leu Glu Lys Glu Leu Ser His Leu Asn Arg Glu Phe Glu Thr
                1940                1945                1950

Leu Gln Glu Lys Ala Gln Val Asn Ser Arg Lys Ala Gln Thr Leu Tyr
            1955                1960                1965

Asn Asn Ile Asp Gln Thr Ile Gln Ser Ala Lys Glu Leu Asp Met Lys
        1970                1975                1980

Ile Lys Asn Ile Val Gln Asn Val His Ile Leu Leu Lys Gln Met Ala
1985                1990                1995                2000

Arg Pro Gly Gly Glu Gly Thr Asp Leu Pro Val Gly Asp Trp Ser Arg
                2005                2010                2015

Glu Leu Ala Glu Ala Gln Arg Met Met Arg Asp Leu Arg Ser Arg Asp
            2020                2025                2030

Phe Lys Lys His Leu Gln Glu Ala Glu Ala Glu Lys Met Glu Ala Gln
            2035                2040                2045

Leu Leu Leu His Arg Ile Arg Thr Trp Leu Glu Ser His Gln Val Glu
        2050                2055                2060

Asn Asn Gly Leu Leu Lys Asn Ile Arg Asp Ser Leu Asn Asp Tyr Glu
2065                2070                2075                2080

Asp Lys Leu Gln Asp Leu Arg Ser Ile Leu Gln Glu Ala Ala Ala Gln
            2085                2090                2095

Ala Lys Gln Ala Thr Gly Ile Asn His Glu Asn Glu Gly Val Leu Gly
            2100                2105                2110

Ala Ile Gln Arg Gln Met Lys Glu Met Asp Ser Leu Lys Asn Asp Phe
        2115                2120                2125

Thr Lys Tyr Leu Ala Thr Ala Asp Ser Ser Leu Leu Gln Thr Asn Asn
        2130                2135                2140

Leu Leu Gln Gln Met Asp Lys Ser Gln Lys Glu Tyr Glu Ser Leu Ala
2145                2150                2155                2160

Ala Ala Leu Asn Gly Ala Arg Gln Glu Leu Ser Asp Arg Val Arg Glu
            2165                2170                2175

Leu Ser Arg Ser Gly Gly Lys Ala Pro Leu Val Val Glu Ala Glu Lys
        2180                2185                2190

His Ala Gln Ser Leu Gln Glu Leu Ala Lys Gln Leu Glu Glu Ile Lys
        2195                2200                2205

Arg Asn Thr Ser Gly Asp Glu Leu Val Arg Cys Ala Val Asp Ala Ala
        2210                2215                2220

Thr Ala Tyr Glu Asn Ile Leu Asn Ala Ile Arg Ala Ala Glu Asp Ala
2225                2230                2235                2240

Ala Ser Lys Ala Thr Ser Ala Ser Lys Ser Ala Phe Gln Thr Val Ile
            2245                2250                2255

Lys Glu Asp Leu Pro Lys Arg Ala Lys Thr Leu Ser Ser Asp Ser Glu
            2260                2265                2270

Glu Leu Leu Asn Glu Ala Lys Met Thr Gln Lys Arg Leu Gln Gln Val
        2275                2280                2285

Ser Pro Ala Leu Asn Ser Leu Gln Gln Thr Leu Lys Thr Val Ser Val
```

```
                2290                2295                2300
Gln Lys Asp Leu Leu Asp Ala Asn Leu Thr Val Ala Arg Asp Leu
2305                2310                2315                2320

His Gly Ile Gln Arg Gly Asp Ile Asp Ser Val Val Ile Gly Ala Lys
                2325                2330                2335

Ser Met Val Arg Glu Ala Asn Gly Ile Thr Ser Glu Val Leu Asp Gly
            2340                2345                2350

Leu Asn Pro Ile Gln Thr Asp Leu Gly Arg Ile Lys Asp Ser Tyr Glu
            2355                2360                2365

Ser Ala Arg Arg Glu Asp Phe Ser Lys Ala Leu Val Asp Ala Asn Asn
    2370                2375                2380

Ser Val Lys Lys Leu Thr Arg Lys Leu Pro Asp Leu Phe Ile Lys Ile
2385                2390                2395                2400

Glu Ser Ile Asn Gln Gln Leu Leu Pro Leu Gly Asn Ile Ser Asp Asn
            2405                2410                2415

Val Asp Arg Ile Arg Glu Leu Ile Gln Gln Ala Arg Asp Ala Ala Asn
            2420                2425                2430

Lys Val Gly Ile Pro Ile Trp Leu
        2435                2440

<210> SEQ ID NO 11
<211> LENGTH: 360
<212> TYPE: PRT
<213> ORGANISM: Homo sapiens

<400> SEQUENCE: 11

Cys Ser Pro Leu Pro Lys Thr Gln Ala Asn His Gly Ala Leu Gln Phe
1               5                   10                  15

Gly Asp Ile Pro Thr Ser His Leu Leu Phe Lys Leu Pro Gln Glu Leu
            20                  25                  30

Leu Lys Pro Arg Ser Gln Phe Ala Val Asp Met Gln Thr Thr Ser Ser
        35                  40                  45

Arg Gly Leu Val Phe His Thr Gly Thr Lys Asn Ser Phe Met Ala Leu
    50                  55                  60

Tyr Leu Ser Lys Gly Arg Leu Val Phe Ala Leu Gly Thr Asp Gly Lys
65                  70                  75                  80

Lys Leu Arg Ile Lys Ser Lys Glu Lys Cys Asn Asp Gly Lys Trp His
                85                  90                  95

Thr Val Val Phe Gly His Asp Gly Glu Lys Gly Arg Leu Val Val Asp
            100                 105                 110

Gly Leu Arg Ala Arg Glu Gly Ser Leu Pro Gly Asn Ser Thr Ile Ser
        115                 120                 125

Ile Arg Ala Pro Val Tyr Leu Gly Ser Pro Pro Ser Gly Lys Pro Lys
    130                 135                 140

Ser Leu Pro Thr Asn Ser Phe Val Gly Cys Leu Lys Asn Phe Gln Leu
145                 150                 155                 160

Asp Ser Lys Pro Leu Tyr Thr Pro Ser Ser Phe Gly Val Ser Ser
                165                 170                 175

Cys Leu Gly Gly Pro Leu Glu Lys Gly Ile Tyr Phe Ser Glu Glu Gly
            180                 185                 190

Gly His Val Val Leu Ala His Ser Val Leu Leu Gly Pro Glu Phe Lys
        195                 200                 205

Leu Val Phe Ser Ile Arg Pro Arg Ser Leu Thr Gly Ile Leu Ile His
    210                 215                 220
```

```
Ile Gly Ser Gln Pro Gly Lys His Leu Cys Val Tyr Leu Glu Ala Gly
225                 230                 235                 240

Lys Val Thr Ala Ser Met Asp Ser Gly Ala Gly Thr Ser Thr Ser
                245                 250                 255

Val Thr Pro Lys Gln Ser Leu Cys Asp Gly Gln Trp His Ser Val Ala
                260                 265                 270

Val Thr Ile Lys Gln His Ile Leu His Leu Glu Leu Asp Thr Asp Ser
            275                 280                 285

Ser Tyr Thr Ala Gly Gln Ile Pro Phe Pro Pro Ala Ser Thr Gln Glu
        290                 295                 300

Pro Leu His Leu Gly Ala Pro Ala Asn Leu Thr Thr Leu Arg Ile
305                 310                 315                 320

Pro Val Trp Lys Ser Phe Phe Gly Cys Leu Arg Asn Ile His Val Asn
                325                 330                 335

His Ile Pro Val Pro Val Thr Glu Ala Leu Glu Val Gln Gly Pro Val
            340                 345                 350

Ser Leu Asn Gly Cys Pro Asp Gln
        355                 360

<210> SEQ ID NO 12
<211> LENGTH: 1371
<212> TYPE: DNA
<213> ORGANISM: Homo sapiens

<400> SEQUENCE: 12
tgctcaccac ttcccaagac ccaggccaat catggagccc tccagtttgg ggacattccc      60
accagccact tgctattcaa gcttcctcag gagctgctga aacccaggtc acagtttgct     120
gtggacatgc agacaacatc ctccagagga ctggtgtttc acgggcac taagaactcc      180 tttatggctc tttatctttc aaaaggacgt ctggtctttg cactggggac agatgggaaa     240
aaattgagga tcaaaagcaa ggagaaatgc aatgatggga atggcacac ggtggtgttt      300 ggccatgatg gggaaaaggg gcgcttggtt gtggatggac tgagggcccg ggagggaagt     360
ttgcctggaa actccaccat cagcatcaga gcgccagttt acctgggatc acctccatca     420
gggaaaccaa agagcctccc cacaaacagc tttgtgggat gcctgaagaa ctttcagctg     480
gattcaaaac ccttgtatac ccttcttca agcttcgggg tgtcttcctg cttgggtggt     540
cctttggaga aaggcattta tttctctgaa gaaggaggtc atgtcgtctt ggctcactct     600
gtattgttgg ggccagaatt taagcttgtt ttcagcatcc gcccaagaag tctcactggg     660
atcctaatac acatcggaag tcagcccggg aagcacttat gtgtttacct ggaggcagga     720
aaggtcacgg cctctatgga cagtggggca ggtgggacct caacgtcggt cacaccaaag     780
cagtctctgt gtgatggaca gtggcactcg gtggcagtca ccataaaaca acacatcctg     840
cacctggaac tggacacaga cagtagctac acagctggac agatccccctt cccacctgcc     900 agcactcaag agccactaca ccttggaggt gctccagcca atttgacgac actgaggatc     960
cctgtgtgga aatcattctt tggctgtctg aggaatattc atgtcaatca catccctgtc    1020
cctgtcactg aagccttgga agtccagggg cctgtcagtc tgaatggttg tcctgaccag    1080
taacccaagc ctatttcaca gcaaggaaat tcaccttcaa aagcactgat tacccaatgc    1140
acctccctcc ccagctcgag atcattcttc aattaggaca caaaccagac aggtttaata    1200
gcgaatctaa ttttgaattc tgaccatgga tacccatcac tttggcattc agtgctacat    1260
gtgtatttta tataaaaatc ccatttcttg aagataaaaa aattgttatt caaattgtta    1320
```

-continued tgcacagaat gttttttggta atattaattt ccactaaaaa attaaatgtc t         1371

<210> SEQ ID NO 13
<211> LENGTH: 184
<212> TYPE: PRT
<213> ORGANISM: Homo sapiens

<400> SEQUENCE: 13

Cys Leu Gly Gly Pro Leu Glu Lys Gly Ile Tyr Phe Ser Glu Glu Gly
1               5                   10                  15

Gly His Val Val Leu Ala His Ser Val Leu Leu Gly Pro Glu Phe Lys
            20                  25                  30

Leu Val Phe Ser Ile Arg Pro Arg Ser Leu Thr Gly Ile Leu Ile His
        35                  40                  45

Ile Gly Ser Gln Pro Gly Lys His Leu Cys Val Tyr Leu Glu Ala Gly
    50                  55                  60

Lys Val Thr Ala Ser Met Asp Ser Gly Ala Gly Gly Thr Ser Thr Ser
65                  70                  75                  80

Val Thr Pro Lys Gln Ser Leu Cys Asp Gly Gln Trp His Ser Val Ala
                85                  90                  95

Val Thr Ile Lys Gln His Ile Leu His Leu Glu Leu Asp Thr Asp Ser
            100                 105                 110

Ser Tyr Thr Ala Gly Gln Ile Pro Phe Pro Pro Ala Ser Thr Gln Glu
        115                 120                 125

Pro Leu His Leu Gly Gly Ala Pro Ala Asn Leu Thr Thr Leu Arg Ile
    130                 135                 140

Pro Val Trp Lys Ser Phe Phe Gly Cys Leu Arg Asn Ile His Val Asn
145                 150                 155                 160

His Ile Pro Val Pro Val Thr Glu Ala Leu Glu Val Gln Gly Pro Val
                165                 170                 175

Ser Leu Asn Gly Cys Pro Asp Gln
            180

<210> SEQ ID NO 14
<211> LENGTH: 843
<212> TYPE: DNA
<213> ORGANISM: Homo sapiens

<400> SEQUENCE: 14
tgcttgggtg gtcctttgga gaaaggcatt tatttctctg aagaaggagg tcatgtcgtc     60
ttggctcact ctgtattgtt ggggccagaa tttaagcttg ttttcagcat ccgcccaaga    120
agtctcactg ggatcctaat acacatcgga agtcagcccg ggaagcactt atgtgtttac    180
ctggaggcag gaaaggtcac ggcctctatg gacagtgggg caggtgggac ctcaacgtcg    240
gtcacaccaa agcagtctct gtgtgatgga cagtggcact cggtggcagt caccataaaa    300
caacacatcc tgcacctgga actggacaca gacagtagcc acacagctgg acagatcccc    360
ttcccacctg ccagcactca agagccacta ccccttggag gtgctccagc caatttgacg    420
acactgagga tccctgtgtg gaaatcattc tttggctgtc tgaggaatat tcatgtcaat    480
cacatccctg tccctgtcac tgaagccttg gaagtccagg ggcctgtcag tctgaatggt    540
tgtcctgacc agtaacccaa gcctatttca gcaaggaa attcaccttc aaaagcactg    600
attacccaat gcacctccct ccccagctcg agatcattct tcaattagga cacaaaccag    660
acaggtttaa tagcgaatct aattttgaat tctgaccatg gatacccatc actttggcat    720
tcagtgctac atgtgtattt tatataaaaa tcccatttct tgaagataaa aaaattgtta    780
ttcaaattgt tatgcacaga atgtttttgg taatattaat ttccactaaa aaattaaatg    840
tct                                                                  843

<210> SEQ ID NO 15
<211> LENGTH: 11
<212> TYPE: PRT
<213> ORGANISM: Homo sapiens

<400> SEQUENCE: 15

Pro Leu Pro Lys Thr Gln Ala Asn His Gly Ala
 1               5                  10

<210> SEQ ID NO 16
<211> LENGTH: 31
<212> TYPE: DNA
<213> ORGANISM: Homo sapiens

<400> SEQUENCE: 16
cacttcccaa gacccaggcc aatcatggag c                                    31

<210> SEQ ID NO 17
<211> LENGTH: 16
<212> TYPE: PRT
<213> ORGANISM: Homo sapiens

<400> SEQUENCE: 17

Ser His Leu Leu Phe Lys Leu Pro Gln Glu Leu Leu Lys Pro Arg Ser
 1               5                  10                  15

<210> SEQ ID NO 18
<211> LENGTH: 47
<212> TYPE: DNA
<213> ORGANISM: Homo sapiens

<400> SEQUENCE: 18
gccacttgct attcaagctt cctcaggagc tgctgaaacc caggtca                   47

<210> SEQ ID NO 19
<211> LENGTH: 131
<212> TYPE: PRT
<213> ORGANISM: Homo sapiens

<400> SEQUENCE: 19

Thr Ser Ser Arg Gly Leu Val Phe His Thr Gly Thr Lys Asn Ser Phe
 1               5                  10                  15

Met Ala Leu Tyr Leu Ser Lys Gly Arg Leu Val Phe Ala Leu Gly Thr
                20                  25                  30

Asp Gly Lys Lys Leu Arg Ile Lys Ser Lys Glu Lys Cys Asn Asp Gly
            35                  40                  45

Lys Trp His Thr Val Val Phe Gly His Asp Gly Glu Lys Gly Arg Leu
        50                  55                  60

Val Val Asp Gly Leu Arg Ala Arg Glu Gly Ser Leu Pro Gly Asn Ser
65                  70                  75                  80

Thr Ile Ser Ile Arg Ala Pro Val Tyr Leu Gly Ser Pro Pro Ser Gly
                85                  90                  95

Lys Pro Lys Ser Leu Pro Thr Asn Ser Phe Val Gly Cys Leu Lys Asn
            100                 105                 110

Phe Gln Leu Asp Ser Lys Pro Leu Tyr Thr Pro Ser Ser Ser Phe Gly
        115                 120                 125

Val Ser Ser
    130

<210> SEQ ID NO 20
<211> LENGTH: 398
<212> TYPE: DNA
<213> ORGANISM: Homo sapiens

<400> SEQUENCE: 20

```
gacaacatcc tccagaggac tggtgtttca cacgggcact aagaactcct ttatggctct      60
ttatctttca aaaggacgtc tggtctttgc actggggaca gatgggaaaa aattgaggat     120
caaaagcaag gagaaatgca atgatgggaa atggcacacg gtggtgtttg ccatgatgg      180
ggaaaagggg cgcttggttg tggatggact gagggcccgg gagggaagtt tgcctggaaa     240
ctccaccatc agcatcagag cgccagttta cctgggatca cctccatcag ggaaaccaaa     300
gagcctcccc acaaacagct tgtgggatg cctgaagaac tttcagctgg attcaaaacc      360
cttgtatacc ccttcttcaa gcttcggggt gtcttcct                             398
```

<210> SEQ ID NO 21
<211> LENGTH: 315
<212> TYPE: PRT
<213> ORGANISM: Homo sapiens

<400> SEQUENCE: 21

Thr Ser Ser Arg Gly Leu Val Phe His Thr Gly Thr Lys Asn Ser Phe
1               5                   10                  15

Met Ala Leu Tyr Leu Ser Lys Gly Arg Leu Val Phe Ala Leu Gly Thr
            20                  25                  30

Asp Gly Lys Lys Leu Arg Ile Lys Ser Lys Glu Lys Cys Asn Asp Gly
        35                  40                  45

Lys Trp His Thr Val Val Phe Gly His Asp Gly Glu Lys Gly Arg Leu
    50                  55                  60

Val Val Asp Gly Leu Arg Ala Arg Glu Gly Ser Leu Pro Gly Asn Ser
65                  70                  75                  80

Thr Ile Ser Ile Arg Ala Pro Val Tyr Leu Gly Ser Pro Pro Ser Gly
                85                  90                  95

Lys Pro Lys Ser Leu Pro Thr Asn Ser Phe Val Gly Cys Leu Lys Asn
            100                 105                 110

Phe Gln Leu Asp Ser Lys Pro Leu Tyr Thr Pro Ser Ser Ser Phe Gly
        115                 120                 125

Val Ser Ser Cys Leu Gly Gly Pro Leu Glu Lys Gly Ile Tyr Phe Ser
    130                 135                 140

Glu Glu Gly Gly His Val Val Leu Ala His Ser Val Leu Leu Gly Pro
145                 150                 155                 160

Glu Phe Lys Leu Val Phe Ser Ile Arg Pro Arg Ser Leu Thr Gly Ile
                165                 170                 175

Leu Ile His Ile Gly Ser Gln Pro Gly Lys His Leu Cys Val Tyr Leu
            180                 185                 190

Glu Ala Gly Lys Val Thr Ala Ser Met Asp Ser Gly Ala Gly Gly Thr
        195                 200                 205

Ser Thr Ser Val Thr Pro Lys Gln Ser Leu Cys Asp Gly Gln Trp His
    210                 215                 220

Ser Val Ala Val Thr Ile Lys Gln His Ile Leu His Leu Glu Leu Asp
225                 230                 235                 240

Thr Asp Ser Ser Tyr Thr Ala Gly Gln Ile Pro Phe Pro Pro Ala Ser

```
                    245                 250                 255
Thr Gln Glu Pro Leu His Leu Gly Gly Ala Pro Ala Asn Leu Thr Thr
        260                 265                 270

Leu Arg Ile Pro Val Trp Lys Ser Phe Phe Gly Cys Leu Arg Asn Ile
            275                 280                 285

His Val Asn His Ile Pro Val Pro Val Thr Glu Ala Leu Glu Val Gln
        290                 295                 300

Gly Pro Val Ser Leu Asn Gly Cys Pro Asp Gln
305                 310                 315

<210> SEQ ID NO 22
<211> LENGTH: 935
<212> TYPE: DNA
<213> ORGANISM: Homo sapiens

<400> SEQUENCE: 22
catcctccag aggactggtg tttcacacgg gcactaagaa ctcctttatg gctctttatc      60
tttcaaaagg acgtctggtc tttgcactgg ggacagatgg gaaaaaattg aggatcaaaa    120
gcaaggagaa atgcaatgat gggaaatggc acacggtggt gtttggccat gatggggaaa    180
aggggcgctt ggttgtggat ggactgaggg cccgggaggg aagtttgcct ggaaactcca    240
ccatcagcat cagagcgcca gtttacctgg gatcacctcc atcagggaaa ccaagagcc     300 tccccacaaa cagctttgtg ggatgcctga agaactttca gctggattca aaacccttgt    360
ataccccttc ttcaagcttc ggggtgtctt cctgcttggg tggtcctttg agaaaggca    420 tttatttctc tgaagaagga ggtcatgtcg tcttggctca ctctgtattg ttggggccag    480
aatttaagct tgtttttcagc atccgcccaa gaagtctcac tgggatccta atacacatcg    540
gaagtcagcc cgggaagcac ttatgtgttt acctggaggc aggaaaggtc acggcctcta    600
tggacagtgg ggcaggtggg acctcaacgt cggtcacacc aaagcagtct ctgtgtgatg    660
gacagtggca ctcggtggca gtcaccataa acaacacat cctgcacctg gaactggaca    720
cagacagtag ctacacagct ggacagatcc ccttcccacc tgccagcact caagagccac    780
tacaccttgg aggtgctcca gccaatttga cgacactgag gatccctgtg tggaaatcat    840
tctttggctg tctgaggaat attcatgtca atcacatccc tgtccctgtc actgaagcct    900
tggaagtcca ggggcctgtc agtctgaatg gttgt                                935

<210> SEQ ID NO 23
<211> LENGTH: 154
<212> TYPE: PRT
<213> ORGANISM: Homo sapiens

<400> SEQUENCE: 23

Phe Lys Leu Val Phe Ser Ile Arg Pro Arg Ser Leu Thr Gly Ile Leu
1               5                   10                  15

Ile His Ile Gly Ser Gln Pro Gly Lys His Leu Cys Val Tyr Leu Glu
            20                  25                  30

Ala Gly Lys Val Thr Ala Ser Met Asp Ser Gly Ala Gly Gly Thr Ser
        35                  40                  45

Thr Ser Val Thr Pro Lys Gln Ser Leu Cys Asp Gly Gln Trp His Ser
    50                  55                  60

Val Ala Val Thr Ile Lys Gln His Ile Leu His Leu Glu Leu Asp Thr
65                  70                  75                  80

Asp Ser Ser Tyr Thr Ala Gly Gln Ile Pro Phe Pro Pro Ala Ser Thr
                85                  90                  95
```

```
Gln Glu Pro Leu His Leu Gly Gly Ala Pro Ala Asn Leu Thr Thr Leu
            100                 105                 110

Arg Ile Pro Val Trp Lys Ser Phe Phe Gly Cys Leu Arg Asn Ile His
        115                 120                 125

Val Asn His Ile Pro Val Pro Val Thr Glu Ala Leu Glu Val Gln Gly
    130                 135                 140

Pro Val Ser Leu Asn Gly Cys Pro Asp Gln
145                 150

<210> SEQ ID NO 24
<211> LENGTH: 462
<212> TYPE: DNA
<213> ORGANISM: Homo sapiens

<400> SEQUENCE: 24
ttaagcttgt tttcagcatc cgcccaagaa gtctcactgg gatcctaata cacatcggaa     60
gtcagcccgg gaagcactta tgtgtttacc tggaggcagg aaaggtcacg gcctctatgg    120
acagtggggc aggtgggacc tcaacgtcgg tcacaccaaa gcagtctctg tgtgatggac    180
agtggcactc ggtggcagtc accataaaac aacacatcct gcacctggaa ctggacacag    240
acagtagcta cacagctgga cagatcccct tcccacctgc cagcactcaa gagccactac    300
accttggagg tgctccagcc aatttgacga cactgaggat ccctgtgtgg aaatcattct    360
ttggctgtct gaggaatatt catgtcaatc acatccctgt ccctgtcact gaagccttgg    420
aagtccaggg gcctgtcagt ctgaatggtt gtcctgacca gt                       462

<210> SEQ ID NO 25
<211> LENGTH: 27
<212> TYPE: DNA
<213> ORGANISM: Artificial Sequence
<220> FEATURE:
<223> OTHER INFORMATION: WT and delta-G45 cDNA Forward Primer

<400> SEQUENCE: 25
aaaaaagcta gcatgggttg gcttata                                         27

<210> SEQ ID NO 26
<211> LENGTH: 80
<212> TYPE: DNA
<213> ORGANISM: Artificial Sequence
<220> FEATURE:
<223> OTHER INFORMATION: alpha-3WT cDNA Reverse Primer

<400> SEQUENCE: 26
cccccccggc ccgcggccgc ttacaggtcc tcctcgctaa tcaattttg ctcctggtca      60 ggacaaccat tcagactgac                                                 80

<210> SEQ ID NO 27
<211> LENGTH: 80
<212> TYPE: DNA
<213> ORGANISM: Artificial Sequence
<220> FEATURE:
<223> OTHER INFORMATION: Delta-G45 Reverse Primer

<400> SEQUENCE: 27
aaaaaaccag gtttaacaag accaagactt ttcgtatcaa cctgctgttg ctggccacac     60
cagtggcctc ccctaggagc                                                 80

<210> SEQ ID NO 28
```

```
<211> LENGTH: 22
<212> TYPE: DNA
<213> ORGANISM: Artificial Sequence
<220> FEATURE:
<223> OTHER INFORMATION: G45 Forward Primer

<400> SEQUENCE: 28
ttatgctagc ggacacacca gt                                              22

<210> SEQ ID NO 29
<211> LENGTH: 24
<212> TYPE: DNA
<213> ORGANISM: Artificial Sequence
<220> FEATURE:
<223> OTHER INFORMATION: G45 Reverse Primer

<400> SEQUENCE: 29
tattctcgag ttactggtca ggac                                            24
```